US007897736B2

(12) United States Patent
Reed et al.

(10) Patent No.: US 7,897,736 B2
(45) Date of Patent: Mar. 1, 2011

(54) FLUORESCENT QUENCHING DETECTING REAGENTS AND METHODS

(75) Inventors: Michael W. Reed, Lake Forest Park, WA (US); Eugeny Alexander Lukhtanov, Bothell, WA (US); Alexander A. Gall, Woodinville, WA (US); Robert O. Dempcy, Kirkland, WA (US); Nicolaas M. J. Vermeulen, Woodinville, WA (US)

(73) Assignee: Elitech Holding B.V. (NL)

( * ) Notice: Subject to any disclaimer, the term of this patent is extended or adjusted under 35 U.S.C. 154(b) by 0 days.

(21) Appl. No.: 12/683,326

(22) Filed: Jan. 6, 2010

(65) Prior Publication Data
US 2010/0174058 A1 Jul. 8, 2010

Related U.S. Application Data

(63) Continuation of application No. 10/113,445, filed on Mar. 29, 2002, now abandoned, which is a continuation of application No. 09/876,830, filed on Jun. 6, 2001, now Pat. No. 6,790,945, which is a continuation-in-part of application No. 09/457,616, filed on Dec. 8, 1999, now Pat. No. 6,727,356.

(51) Int. Cl.
C07G 3/00 (2006.01)
C07H 21/00 (2006.01)
C07H 21/02 (2006.01)
C07H 19/04 (2006.01)
C12Q 1/68 (2006.01)

(52) U.S. Cl. .................. 536/4.1; 536/25.3; 536/26.6; 536/23.1; 435/6

(58) Field of Classification Search .................. 536/4.1, 536/23.1, 25.3, 26.6; 435/6
See application file for complete search history.

(56) References Cited

U.S. PATENT DOCUMENTS

| 2,264,303 | A | 12/1941 | Dickey |
| 3,407,189 | A | 10/1968 | Merian |
| 4,358,535 | A | 11/1982 | Falkow et al. |
| 4,868,105 | A | 9/1989 | Urdea et al. |
| 4,954,630 | A | 9/1990 | Klein et al. |
| 5,124,246 | A | 6/1992 | Urdea et al. |
| 5,210,015 | A | 5/1993 | Gelfand et al. |
| 5,272,259 | A | 12/1993 | Claussen et al. |
| 5,304,645 | A | 4/1994 | Klein et al. |
| 5,328,824 | A | 7/1994 | Ward |
| 5,451,463 | A | 9/1995 | Nelson et al. |
| 5,455,157 | A | 10/1995 | Hinzpeter et al. |
| 5,492,806 | A | 2/1996 | Drmanac et al. |
| 5,502,177 | A | 3/1996 | Matteucci et al. |
| 5,512,667 | A | 4/1996 | Reed et al. |
| 5,525,464 | A | 6/1996 | Drmanac et al. |
| 5,556,752 | A | 9/1996 | Lockhart et al. |
| 5,696,251 | A | 12/1997 | Arnold, Jr. et al. |
| 5,801,155 | A | 9/1998 | Kutyavin et al. |
| 5,824,796 | A | 10/1998 | Petrie et al. |
| 5,830,653 | A | 11/1998 | Froehler et al. |
| 5,846,726 | A | 12/1998 | Nadeau |
| 5,876,930 | A | 3/1999 | Livak et al. |
| 5,942,610 | A | 8/1999 | Nelson et al. |
| 5,952,202 | A | 9/1999 | Aoyagi et al. |
| 6,007,992 | A | 12/1999 | Lin et al. |
| 6,028,183 | A | 2/2000 | Lin et al. |
| 6,114,518 | A | 9/2000 | Pitner et al. |
| 6,117,986 | A | 9/2000 | Nardone et al. |
| 6,312,894 | B1 | 11/2001 | Hedgpeth et al. |
| 6,323,337 | B1 | 11/2001 | Singer et al. |
| 6,399,392 | B1 | 6/2002 | Haugland et al. |
| 6,416,953 | B1 | 7/2002 | Heller |
| 6,448,407 | B1 | 9/2002 | Lee et al. |
| 6,465,175 | B2 | 10/2002 | Horn et al. |
| 6,465,644 | B1 | 10/2002 | Yan et al. |
| 6,485,901 | B1 | 11/2002 | Gildea et al. |
| 6,531,581 | B1 | 3/2003 | Nardone et al. |

FOREIGN PATENT DOCUMENTS

| GB | 1 394 368 | 5/1975 |
| GB | 1 533 121 | 11/1978 |
| WO | WO 90/14353 | 11/1990 |
| WO | WO 92/10588 | 6/1992 |
| WO | WO 96/17957 | 6/1996 |
| WO | WO 97/29154 | 8/1997 |
| WO | WO 97/39008 | 10/1997 |
| WO | WO 99/40226 | 8/1999 |
| WO | WO 99/51621 | 10/1999 |
| WO | WO 99/64431 | 12/1999 |
| WO | WO 00/06711 | 2/2000 |
| WO | WO 00/70685 | 11/2000 |

OTHER PUBLICATIONS

Dawson, "The Structure and Properties of Disperse Dyes in Polyester Coloration," *JSDC*, vol. 99, Jul./Aug. 1983, pp. 183-191.

(Continued)

*Primary Examiner*—Jezia Riley
(74) *Attorney, Agent, or Firm*—Jackson Walker L.L.P.; Sara K. Borrelli

(57) ABSTRACT

Oligonucleotide probes containing two labels are provided and are useful in hybridization assays. The probes can also contain a minor groove binding group.

17 Claims, 5 Drawing Sheets

OTHER PUBLICATIONS

Lee et al., "Seven-Color, Homogeneous Detection of Six PCR Products," *Bio Techniques*, vol. 27, No. 2, 1999 (4 pgs.).
Milesi, "Synthesis of Oligonucleotide Conjugates in Anhydrous Dimethylsulfoxide," *Methods in Enzymology*, Nov. 1999 (8 pgs.).
Asanuma et al., "Photo-Responsive Oligonucleotides Carrying Azobenzene in the Side-Chains," *Tetrahedron Letters*, vol. 39, 1998, pp. 9015-9018.
Young et al., Quantitative Analysis of Solution Hybridisation, (Edited by Hames and Higgins), *IRL Press*, 1985, pp. 47-111.
Sokol et al., "Real Time Detection of DNA-RNA Hybridization in Living Cells," *Proc. Nat'l. Acad. Sci.*, vol. 95, Sep. 1998, pp. 11538-11543.
Heesemann, "Studies on Monolayers. 2. Designed Monolayer Assemblies of Mixed Films of Surface-Active Azo Dyes," *Journal of the American Chemical Society*, vol. 102, No. 7, Mar. 26, 1980, pp. 2176-2167.
Sabnis et al., "Synthesis and Application of 5-Arylazothiophene Derivatives," *The Chemical Society of Japan, Bull. Chem. Soc. Jpn.*, vol. 64, No. 12, pp. 3768-3770.
Sijm et al., "Aqueous Solubility, Octanol Solubility, and Octanol/Water Partition Coefficient of Nine Hydrophobic Dyes," *Environmental Toxicology and Chemistry*, Vo. 18, No. 6, 1999, pp. 1109-1117.
Weaver et al., "Heterocyclic Diazo Components," *Dyes and Pigments*, vol. 3, 1982, pp. 81-121.
Keil et al., "Preparation and UV/Vis Spectroscopic Characterization of N,N-Disubstituted 2-Amino-5-arylazoselenazoles and Some of Their Carbocyclic and Heterocyclic Analogues," *J. Prakt. Chem.*, 2000, vol. 342, No. 2, pp. 169-174.
Lyttle et al., "Alternataives to FRET: Design of Fluoroescence-Quenched Oligonucleotide Probes with Extremely High Signal/Noise Ratios," BIOSIS Database, Accession, No. 2001:519181. See also Poster Session from *12th International Genome Sequencing and Analysis Conferrence*, Miami Beach, Florida, Sep. 12-15, 2000 (1 pg.).
Hirshberg et al., "Crystal Structure of Phosphate Binding Protein Labeled with a Coumarin Fluorophore, a Probe for Inorganic Phosphate," *Biochemistry*, 1998, vol. 37, pp. 10381-10385.
Uhlmann et al., "PNA: Sysnthetic Polyamide Nucleic Acids with Unusual Binding Properties," *Angew. Chem. Int. Ed.*, 1998, vol. 37, pp. 2796-2823.
Mayfield et al., "Enhancing Solid Phase Synthesis by a Noncovalent Protection Strategy-Efficient Coupling of Rhodamine to Resin-Bound Peptide Nucleic Acids," *Bioorganic & Medicinal Chemistry Letters*, vol. 9, 1999, pp. 1419-1422.
Seela et al., "Duplex Stability of Pyrazolo[3,4-d]Pyrimidine DNA with Bulky 7-Substituents or Lipophilic Side Chains," XIII International Round Table, Nucleosides, Nucleotides and Their Biological Applications, Montpellier, France, Sep. 6-10, 1998, Poster 279 (1 pg.).
Bolli et al., "Watson-Crick Base-Pairing Properties of Bicyclo-DNA," *Nucleic Acids Research*, 1996, vol. 24, No. 23, pp. 4665-4672.
Huang et al., "X-Ray and $^1$H NMR Studies of the Conformational Equilibria of 2-Z-3-Phenyl-1,3,2-Oxazaphosphorinanes. Steric and Stereoelectronic Influences on the Unexpected Axial Preferences of $Me_2N$ and MeNH Substituents on Three-Coordinate Phosphorus," *J. Org. Chem.*, 1993, vol. 58, pp. 6235-6246.
Boger et al., "Studies on the Total Synthesis of CC-1065: Preparation of a Synthetic, Simplified 3-Carbamoyl-1,2-dihydro-3$H$ -Pyrrolo[3,2-e]Indole Dimer/Trimer/Tetramer (CDPI Dimer/Trimer/Tetramer) and Development of Methodology for PDE-I Dimer Methyl Ester Formation," *J. Org. Chem.*, 1987, vol. 52, pp. 1521-1530.
Wittwer et al., "The LightCycler™: A Microvolume Multisample Fluorimeter with Rapid Temperature Control," *BioTechniques*, vol. 22, No. 1, 1997, pp. 176-181.
Holland et al., "Detection of Specific Polymerase Chain Reaction Product by Utilizing the 5' → 3' Exonuclease Activity of *Thermus aquaticus* DNA Polymerase," *Proc. Natl. Acad. Sci. USA*, vol. 88, Aug. 1991, pp. 7276-7280.

Baker et al., "Fluorescent Reagents. Acyl Chlorides and Acyl Hydrazides." *J. Chem. Soc.*, 1950, pp. 170-173.
Forchiassin et al., "An Efficient Snythesis of Trans-Hexahydrochroman-7-One," *J. Heterocyclic Chem.*, vol. 20, 1983, pp. 493-494.
Seela et al., "Synthesis of Oligonucleotides Containing Pyrazolo[3,4-d]-Pyrimidines: The Influence of 7-Substituted 8-Aza-7-Deazaadenines on the Duplex Structure and Stability," *J. Chem. Soc., Perkin Trans.*, vol. 1, 1999, pp. 479-488.
Cardullo et al., "Detection of Nucleic Acid Hybridization by Nonradiative Fluorescence Resonance Energy Transfer," *Proc. Natl. Acad. Sci. USA*, vol. 85, Dec. 1988, pp. 8790-8794.
Nielsen et al., "Sequence-Selective Recognition of DNA by Strand Displacement with a Thymine-Substituted Polyamide," *Science*, vol. 254, 1991, pp. 1497-1500.
Demidov et al., "Kinetics and Mechanism of Polyamide ("Peptide") Nucleic Acid Binding to Duplex DNA," *Proc. Natl. Acad. Sci. USA*, vol. 92, Mar. 1995, p. 2637-2641.
Ibrahim et al., "The Potential of 5' Nuclease PCR for Detecting a Single-Base Polymorphism in Orthopoxvirus," *Molecular and Cellular Probes*, 1997, vol. 11, pp. 143-147.
Matayoshi et al., "Novel Fluorogenic Substrates for Assaying Retroviral Proteases by Resonance Energy Transfer," *Science*, vol. 247, 1990, pp. 954-958.
Wiegant et al., "Multiple and Sensitive Fluorescence in Situ Hybridization with Rhodamine-, Fluorescein-, and Coumarin-Labeled DNAs," *Cytogenet Cell Genet*, vol. 63, 1993, pp. 73-76.
Eisen et al., "DNA Arrays for Analysis of Gene Expression," *Methods in Enzymology*, vol. 303, 1999, pp. 179-205.
Tyagi et al., "Multicolor Molecular Beacons for Allele Discrimination," *Nature Biotechnology*, vol. 16, Jan. 1998, pp. 49-53.
Nazarenko et al., "A Closed Tube Format for Amplification and Detection of DNA Based on Energy Transfer," *Nucleic Acids Research*, vol. 25, No. 12, 1997, pp. 2516-2521.
Lee et al., "Allelic Discrimination by Nick-Translation PCR with Fluorogenic Probes," *Nucleic Acids Research*, vol. 21, No. 16, 1993, pp. 3761-3766.
Livak et al., "Oligonucleotides with Fluorescent Dyes at Opposite Ends Provide a Quenched Probe System Useful for Detecting PCR Product and Nucleic Acid Hybridization," *PCR Methods and Applications*, 1995, pp. 357-362.
Rothman et al., "A New Generation of Fluorescent Chemosensors Demonstrate Improved Analyte Detection Sensitivity and Photobleaching Resistance," *Biorganic & Medicinal Chemistry Letters*, vol. 9, 1999, pp. 509-512.
Cantor et al., "Oligonucleotide Interactions. III. Circular Dichroism Studies of the Conformation of Deoxyoligonucleotides," *Biopolymers*, vol. 9, 1970, pp. 1059-1077.
Gamper, Jr. et al., "Modulation of $C^m$/T, G/A, and G/T Triplex Stability by Conjugate Groups in the Prescence and Absence of KCl," *Biochemistry*, vol. 36, No. 48, 1997, pp. 14816-14826.
Du et al., "PhotochemCAD††: A Computer-Aided Design and Research Tool in Photochemistry," *Photochemistry and Photobiology*, vol. 68, No. 2, 1998, pp. 141-142.
Freifelder, "Physical Biochemistry—Applications to Biochemistry and Molecular Biology," Second Edition, *W.H. Freeman and Company*, New York, 1976/1982, pp. 700-712.
Sambrook, "Molecular Cloning, A Laboratory Manual," Second Edition, *Cold Spring Harbor Laboratory Press*, 1989, pp. 11.45-11.57.
Van Ness et al., "The Use of Oligodeoxynucleotide Probes in Chaotrope-Based Hybridization Solutions," *Nucleic Acids Research*, vol. 19, No. 19, 1991, pp. 5143-5151.
Innis et al. (eds), "PCR Protocols, A Guide to Methods and Applications," *Academic Press*, 1990, pp. 1-27.
Haugland, "Handbook of Fluorescent Probes and Research Chemicals," Sixth Edition, Eugene, Oregon, 1996, pp. 235-236.
Bickett et al., A High Throughput Fluorogenic Substrate for Stromelysin (MMP-3) *Annals New York Academy of Sciences*, vol. 732, 1994, pp. 351-355.
Whitcombe et al., "Detection of PCR Products Using Self-Probing Amplicons and Fluorescence," *Nature Biotechnology*, vol. 17, Aug. 1999, pp. 804-807.
"Nonistopic DNA Probe Techniques," *Academic Press, Inc.*, San Diego, 1992, pp. 311-352.

Mayfield et al., "Automated Synthesis of Peptide Nucleic Acids and Peptide Nucleic Acid-Peptide Conjugates," *Anal. Biochem.*, vol. 268, 1999, pp. 401-404.

Gamper et al., "Facile Preparation of Nuclease Resistant 3' Modified Oligodeoxynucleotides," *Nucleic Acids Research*, vol. 21, No. 1, 1993, pp. 145-150.

Lukhatanov et al., "Direct, Solid Phase Assembly of Dihydropyrroloindole Peptides with Conjugated Oligonucleotides," *Bioconjugate Chemistry*, vol. 7, No. 5, 1996, pp. 564-567.

White et al., "A Continuous Fluorometric Assay for Leukotriene $D_4$ Hydrolase," *Analytical Biochemistry*, vol. 268, 1999, pp. 245-251.

Petrie et al., "An Improved CPG Support for the Synthesis of 3'-Amine-Tailed Oligonucleotides," *Bioconjugate Chemistry*, vol. 3, 1992, pp. 85-87.

Reed et al., "Acridine- and Cholesterol-Derivatized Solid Supports for Improved Synthesis of 3'-Modified Oligonucleotides," *Bioconjugate Chemistry*, vol. 2, 1991, pp. 217-225.

Pon et al., "Hydroquinone-O, O -Diacetic Acid ('Q-Linker') as a Replacement for Succinyl and Oxalyl Linker Arms in Solid Phase Oligonucleotide Synthesis," *Nucleic Acids Research*, vol. 25, No. 18, 1997, pp. 3629-3635.

Li et al., "Design, Synthesis, and Spectroscopic Properties of Peptide-Bridged Fluorescence Energy-Transfer Cassettes," *Bioconjugate Chem.*, vol. 10, 1999, pp. 241-245.

Hawthorne et al., "Evaluation of Some Fluorogenic Substrates for Continuous Assay of Aminopeptidase P," *Analytical Biochemistry*, vol. 253, 1997, pp. 13-17.

Wittwer et al., "Continuous Fluorescence Monitoring of Rapid Cycle DNA Amplification," *BioTechniques*, vol. 22, No. 1, 1997, pp. 130-138.

FLUORESCENT QUENCHING DETECTING REAGENTS AND METHODS

This application is a divisional application and claims the benefit of U.S. patent application Ser. No. 11/338,866, entitled "Fluorescent Quenching Detection Reagents and Methods," filed Jan. 23, 2006, which is expressly incorporated herein by reference in its entirety.

BACKGROUND OF THE INVENTION

1. Field of the Invention

The invention relates to oligonucleotide-quencher-fluorescent-dye conjugates having improved characteristics, and to reagents suitable for incorporating novel quencher and fluorescent dye moieties into oligonucleotides. The invention also relates to the use of oligonucleotide-quencher-fluorescent-dye conjugates in detection methods for nucleic acid targets.

2. Description of the Related Art

Synthetic oligonucleotides have been used for years as sequence specific probes for complementary DNA and RNA targets. These methods have broad application in forensics, molecular biology and medical diagnostics since they allow the identification and quantitation of specific nucleic acid targets. Early uses of DNA probes relied on radioactivity (typically $^{32}P$) as the label, while recent methods use reporter molecules which include chemiluminescent and fluorescent groups. Improved instrumentation has allowed the sensitivity of these spectroscopic methods to approach or surpass the radiolabeled methods. Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_0$) is described as the distance between the donor and acceptor molecules where the energy transfer is 50% efficient. Other mechanisms of fluorescence quenching are also known, such as, collisional and charge transfer quenching.

Typically detection methods based on FRET are designed in such a way that the donor fluorophore and acceptor molecules are in close proximity so that quenching of the donor fluorescence is efficient. During the assay, the donor and acceptor molecules are separated such that fluorescence occurs. FRET-based detection assays have been developed in the fields of nucleic acid hybridization and enzymology. Several forms of the FRET hybridization assays are reviewed (Nonisotopic DNA Probe Techniques, Academic Press, Inc., San Diego 1992, pp. 311-352). Quenching can also occur through non-FRET mechanisms, such as collisional quenching (see, Wei et al., *Anal. Chem.* 66:1500-1506 (1994)).

Since its discovery, the polymerase chain reaction (PCR) has revolutionized molecular biology. This technique allows amplification of specific DNA sequences, thus allowing DNA probe assays to be executed from a single DNA target copy. PCR-based diagnostic assays have initially not been used routinely, in part due to problems with sample handling and possible contamination with non-source DNA. Recently, new homogeneous fluorescent-based DNA assays have been described which can detect the progress of PCR as it occurs ("real-time" PCR detection) using spectrofluorometric temperature cyclers. Two popular assay formats use DNA probes which become fluorescent as DNA amplification occurs (fluorogenic probes).

The first format for "real-time" PCR uses DNA probes known as "molecular beacons" (Tyagi et al., Nat. Biotech., 16; 49-53 (1998)). Molecular beacons have a hairpin structure wherein the quencher dye and reporter dye are in intimate contact with each other at the end of the stem of the hairpin. Upon hybridization with a complementary sequence, the loop of the hairpin structure becomes double stranded and forces the quencher and reporter dye apart, thus generating a fluorescent signal. Tyagi et al, reported use of the non-fluorescent quencher dyes including the dabcyl (4-{[4-(dimethylamino) phenyl]diazenyl}benzoyl moiety, absorbance max=453 nm) used in combination with fluorescent reporter dyes of widely varying emission wavelength (475-615 nm). At the time this was surprising since FRET requires significant overlap of the absorption spectrum of the quencher and of the emission spectrum of the reporter. In case of a dabcyl moiety containing (hereinafter "dabcyl") quencher and some fluorescent dyes, the spectral overlap was extremely low, yet quenching efficiency was high. Therefore it was proposed that the mechanism of quenching for the hairpin form of the beacons was not FRET, but collisional quenching. In fact, the UV spectra of the quencher changes in the hairpin form of the beacon, providing evidence of the molecular contact and thus of collisional quenching. A related detection method uses hairpin primers as the fluorogenic probe (Nazarenko et al., *Nucl. Acid Res.* 25:2516-2521 (1997)).

The second format for "real-time" PCR uses DNA probes which are referred to as "5'-nuclease probes" (Lee et al., Nucl. Acid Res., 21: 3761-3766 (1993)). These fluorogenic probes are typically prepared with the quencher at the 3' terminus of a single DNA strand and the fluorophore at the 5' terminus. During each PCR cycle, the 5'-nuclease activity of Taq DNA polymerase cleaves the DNA strand, thereby separating the fluorophore from the quencher and releasing the fluorescent signal. The 5'-nuclease assay requires that the probe be hybridized to the template strand during the primer extension step (60-65° C.). They also disclose the simultaneous "real-time" detection of more than one polynucleotide sequence in the same assay, using more than one fluorophore/quencher pair. The 5'-nuclease PCR assay is depicted in FIG. 1

Initially it was believed that 5'-nuclease probes had to be prepared with the quencher (usually tetramethylrhodamine (TAMRA)) positioned at an internal nucleotide in close proximity to the 5'-fluorophore (usually fluorescein (FAM) or tetrachlorofluorescein (TET)) to get efficient FRET. Later it was found that this is not necessary, and the quencher and the fluorophore can be located at the 3' and 5' end of the ODN, respectively. It has been proposed that the random coil structures formed by these fluorogenic probes in solution allow a 3'-quencher dye to pass within the Forster radius of the 5'-fluorophore during the excited state of the molecule.

A number of donor/acceptor pairs have previously been described, important to the present invention is dabcyl that is used for instance as a quencher of dansyl sulphonamide in chemosensors (Rothman & Still (1999) Med. Chem. Lett. 22:509-512).

Surprisingly, there have been no published reports on the use of dabcyl in 5'-nuclease probes or other FRET probes that use long wavelength fluorophores. As mentioned above, dabcyl was used in the beacon-type probes but this is a different quenching mechanism wherein the dabcyl and fluorophore are in intimate contact (collisional quenching). Dabcyl was used in fluorogenic peptides as a quencher for the fluorophore EDANS (5-[(2-aminoethyl)amino]naphthalene-1-sulfonic acid) which emits at short (490 nm, blue) wavelength (Matayoshi et al. Science 247: 954-958 (1990)). EDANS also has a lower extinction coefficient than dabcyl so it is not surprising that fluorescent quenching was efficient. It was found for the first time in the present invention that dabcyl can be used to quench fluorescein in a FRET type mechanism.

In addition to the 5'-nuclease PCR assay, other formats have been developed that use the FRET mechanism. For example, single-stranded signal primers have been modified by linkage to two dyes to form a donor/acceptor dye pair in such a way that fluorescence of the first dye is quenched by the second dye. This signal primer contains a restriction site (U.S. Pat. No. 5,846,726) that allows the appropriate restriction enzyme to nick the primer when hybridized to a target. This cleavage separates the two dyes and a change in fluorescence is observed due to a decrease in quenching. Non-nucleotide linking reagents to couple oligonucleotides to ligands have also been described (U.S. Pat. No. 5,696,251).

FRET systems also have applications in enzymology. Protease cleavable substrates have been developed where donor/acceptor dye pairs are designed into the substrate. Enzymatic cleavage of the substrate separates the donor/acceptor pair and a change in fluorescence is observed due to a decrease in quenching. Cleavable donor/acceptor substrates have been developed for chymotrypsin (Li et al. Bioconj. Chem., 10: 241-245 (1999)), aminopeptidase P (Hawthorne et al., Anal. Biochem., 253: 13-17 (1997)), stromelysin (Bickett et al., Ann. N.Y. Acad. Sci., 732: 351-355 (1994)) and leukotriene $D_4$ hydrolase (White et al., Anal. Biochem., 268: 245-251 (1999)). A chemosensor was described where binding of the ligand separates the donor/acceptor pair (Rothman et al., Biorg. Med. Chem. Lett., 9:509-512 (1999)).

U.S. Pat. No. 5,801,155 discloses that oligonucleotides (ODNs) having a covalently attached minor groove binder (MGB) are more sequence specific for their complementary targets than unmodified oligonucleotides. In addition the MGB-ODNs show substantial increase in hybrid stability with complementary DNA target strands when compared to unmodified oligonucleotides, allowing hybridization with shorter oligonucleotides.

Reagents for fluorescent labeling of oligonucleotides are critical for efficient application of the FRET assays described above. Other applications such as DNA micro arrays also use fluorescently labeled DNA probes or primers, and there is a need for improved reagents which facilitate synthesis of fluorescent DNA. In general, phosphoramidite reagents and solid supports are widely used on ODN synthesis. However, there are few commercially available phosphoramidite reagents for introducing fluorescent groups into ODNs.

Linker groups to attach different ligand groups to ODNs play an important role in the synthesis of oligonucleotide conjugates. A method for the synthesis of 3'-aminohexyl-tailed oligonucleotides (Petrie et al., Bioconj. Chem., 3:85-87 (1992)), the use of a trifunctional trans-4-hydroxy-L-prolinol group (Reed et al., Bioconjug. Chem., 2:217-225 (1991)), diglycolic acid (Pon et al., Nucl. Acids. Res., 25:3629-3635 (1997)), 1,3-diol reagents (U.S. Pat. Nos. 5,942,610 and 5,451,463) and a non-nucleotide trifunctional reagent (U.S. Pat. No. 5,696,251) have been reported.

Resorufin and coumarin derivatives have been extensively used as enzyme substrates to differentiate isozymes of cytochrome P450 (Haugland et al., Handbook of Fluorescent Probes and Research Chemicals, Six Edition, Eugene, Oreg., of the Several Views, pp. 235-236. 1996.). Reactive resorufin analogs have been disclosed in U.S. Pat. No. 5,304,645. Activated esters of coumarin derivatives are also known in the art (Hirshberg et al., Biochem., 37:10391-5 (1998)). Coumarin-labeled dUTP incorporated in probes were used for in situ hybridizations (Wiegant et al., Cytogenet. Cell Genet., 63:73-76 (1993)). Phosphoramidites to introduce labels into oligonucleotides have been described in U.S. Pat. Nos. 5,328,824 and 5,824,796.

Many current hybridization applications, require more than one reporter molecule. In addition although reporter fluorophores are available to be used in reporter/quencher pairs, most suffer from having some undesirable characteristics, e.g., mixtures are difficult to separate, they are positively charged or difficult to synthesize, unstable during oligonucleotide synthesis or having overlapping emission wavelengths with other desirable reporters.

The present invention provides reagents for oligonucleotide probes that address these unfavorable characteristics and overcome some or all of the difficulties.

BRIEF SUMMARY OF THE INVENTION

In one aspect, the present invention provides an oligonucleotide probe having the formula:

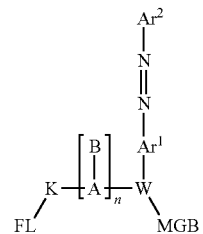

wherein $Ar^1$ and $Ar^2$ each independently represent a substituted or unsubstituted aryl group; MOB is a minor groove binding group; FL is a fluorescent group having an emission maxima in the region from about 400 to about 900 nm; K is a cyclic or acyclic linking group having from 1 to 30 backbone atoms selected from C, N, O, S and P; W is a linking group having from 3 to 100 backbone atoms selected from C, N, O, S, Si and P which is cyclic, acyclic, aromatic or a combination thereof; $[A-B]_n$ is a natural or modified oligonucleotide having from 4 to 100 bases; and the subscript n is an integer of from 4 to 100.

In one group of embodiments, $Ar^1$ is a substituted or unsubstituted aryl group selected from the group consisting of phenyl, naphthyl, 2-benzothiazolyl, 3-benzoisothiazolyl and 2-thiazolyl. In another group of embodiments, $Ar^2$ bears from one to three substituents selected from nitro, cyano, halo, —C(O)R$^1$, —C(O)NR$^1$R$^2$, —SO$_2$R$^1$, —SO$_2$F and —SO$_2$NR$^1$R$^2$, wherein each R$^1$ and R$^2$ is independently H, ($C_1$-$C_6$)alkyl or hydroxy($C_1$-$C_6$)alkyl. In still other embodiments, the group —Ar$^1$—N═N—Ar$^2$ is a quencher moiety having the formula:

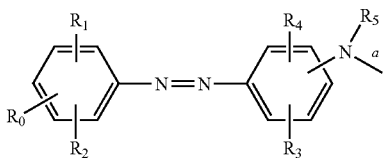

wherein $R_0$, $R_1$, $R_2$, $R_3$ and $R_4$ are independently selected from H, halogen, $NO_2$, $SO_3R$, $SO_2N(R)_2$, C(O)OR, C(O)N$(R)_2$, CN, CNS, OR, OC(O)R, SR, $CF_3$, NHC(O)R, $N(R)_2$ and $N[R]_3$ wherein each R is independently selected from H, $(C_1-C_8)$alkyl, aryl (and heteroaryl), or a blocking group compatible with oligonucleotide synthesis; and $R_5$ is —H or $(C_1-C_8)$alkyl, and the quencher moiety is attached to the linker through the valence bond designated "a". In still other embodiments, the group W—$Ar^1$—N=N—$Ar^2$ is a quencher moiety-linking group combination having a formula selected from Q-1, Q-2 and Q-3:

Q-1

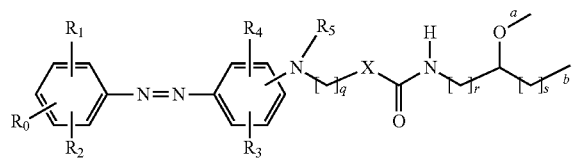

Q-2

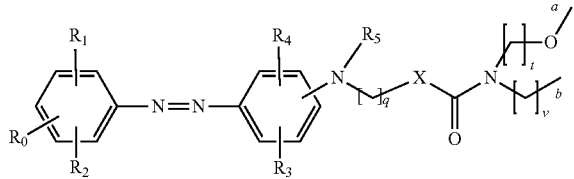

Q-3

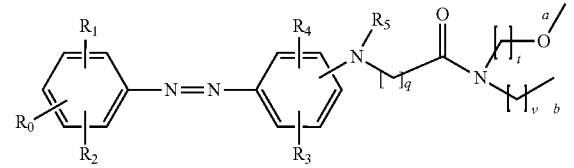

wherein q, r, s, t and v are each independently an integer of from 1 to 20; X is —O—, —$OCH_2$— or —$CH_2$—; and the conjugated quencher and linker moiety is attached to the $[A-B]_n$ portion through one of the valence bonds designated a or b; and is attached to the minor groove binder portion through the other of valence bonds designated a or b.

In still other embodiments, the oligonucleotide probe has a fluorophore, FL selected from the group of FL-1, Fl-2 and Fl-3:

FL-1

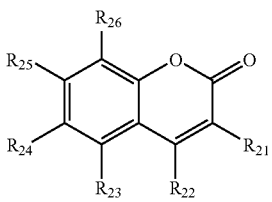

FL-2

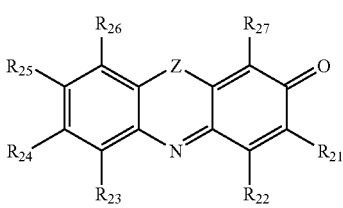

FL-3

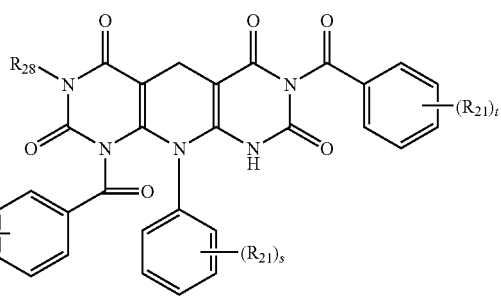

wherein $R_{21}$, $R_{22}$, $R_{23}$, $R_{24}$, $R_{25}$, $R_{26}$ and $R_{27}$ are each substituents independently selected from H, halogen, $NO_2$, $SO_3R$, $SO_2N(R)_2$, C(O)OR, C(O)N$(R)_2$, CN, CNS, OR, OC(O)R, SR, $CF_3$, NHC(O)R, $N(R)_2$ and $N[R]_3$ wherein each R is independently selected from the group consisting of H, $(C_1-C_8)$alkyl, aryl (and heteroaryl), or a blocking group compatible with oligonucleotide synthesis, and optionally two adjacent groups from $R_{21}$ through $R_{26}$ are combined to form a five- or six-membered ring having from zero to three heteroatoms as ring member, with the proviso that at least one of $R_{21}$ through $R_{27}$ is a bond that attaches said fluorophore to said linking group K; and $R_{28}$ is a member selected from the group consisting of H and $(C_1-C_8)$alkyl.

In still other embodiments, the oligonucleotide probes of the invention comprise a minor groove binder (MGB) that is selected from analogs of one of the following: CC1065, Hoechst 33258, DAPI, lexitropsins, distamycin, netropsin, berenil (and related diarylamidines), duocarmycin, pentamidine, 4,6-diamino-2-phenylindole, and pyrrolo[2,1-c][1,4]benzodiazepines.

In preferred embodiments, the probes have attached novel quencher structures (described below), paired with a covalently attached fluorescent moiety. The resulting FL-ODN-Q conjugate will preferably include a minor groove binder (MGB) that improves the binding and discrimination characteristics of the resulting FL-ODN-Q-MGB conjugate. These conjugates find particular utility in diagnostic assays such as the TaqMan® PCR assay for single nucleotide polymorphisms (and the like) where allele-specific discrimination not only requires probes with different fluorescent reporter molecules but efficient quenchers. The quenchers used in the FL-ODN-Q-MGB conjugates are preferably those that provide a broad quenching wavelength range. Additionally, the novel reporter labeling reagents used to prepare these conjugates are those that have distinctive emission wavelengths for improved multicolor analysis.

In one application of the principles summarized above, fluorogenic probes are prepared using a universal "3'-hexanol" solid support (available in accordance with Gamper et al. Nucleic Acids Res., 21:145-150 (1993), where a quencher phosphoramidite of the invention is added at the first coupling step (3'-end) of the ODN sequence and a fluorophore (FL) is attached at the final coupling step, yielding 5'-FL-ODN-Q-hexanol conjugate probes.

In another aspect, the present invention provides a quencher reagents having the formula:

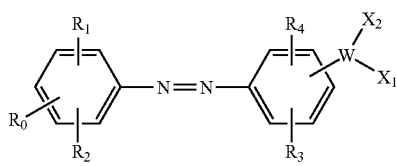

wherein W is a linking group having from 3 to 100 main chain atoms selected from C, N, O, S, P and Si and can be acyclic, cyclic or aromatic or combinations thereof; $X_1$ is H, ($C_1$-$C_{12}$) alkyl, aryl, heteroaryl, protected or unprotected functional group (e.g., a hydroxy, amino or carboxylic acid or ester that optionally is protected with a suitable protecting group as are known to those of skill in the art); $X_2$ is any phosphorus coupling moiety used in oligonucleotide synthesis, for example, a phosphoramidite of the formula O—P(N(iPr)$_2$) (OCH$_2$CH$_2$CN), or alternatively, a linking group attached to a solid support of the formula O—C(=O)Z-solid support wherein Z is 1 to 30 main chain atoms in length wherein the main chain atoms are selected from C, N, O, P, and S, and Z can include acyclic, cyclic or aromatic groups or combinations thereof; and $R_0$, $R_1$, $R_2$, $R_3$ and $R_4$ are independently selected from the group consisting of H, halogen, NO$_2$, SO$_3$R, SO$_2$N(R)$_2$, C(O)OR, C(O)N(R)$_2$, CN, CNS, OR, OC(O)R, SR, CF$_3$, NHC(O)R, N(R)$_2$ or N[R]$_3$ wherein each R is independently H, ($C_1$-$C_8$)alkyl, aryl (and heteroaryl), or a cleavable linking group that is attached to a solid support, or a blocking group compatible with oligonucleotide synthesis and optionally, two of $R_0$, $R_1$ and $R_2$ are combined to form a five- or six-membered ring having from zero to three heteroatoms as ring members; and optionally $R_3$ and $R_4$ are combined to form a five- or six-membered ring having from zero to three heteroatoms as ring members. For those embodiments in which $R_3$ and $R_4$ are combined to form a fused ring system, the linking group W can be attached to either the phenyl ring (as indicated above) or to the ring formed by $R_3$ and $R_4$. Additionally, for those embodiments herein, where two alkyl groups are attached to a nitrogen atom, forming a dialkylamino substituent, the alkyl groups can be the same or different. Preferably, the quencher-phosphoramidite reagent has a formula selected from formulas designated PA-1, PA-2 and PA-3

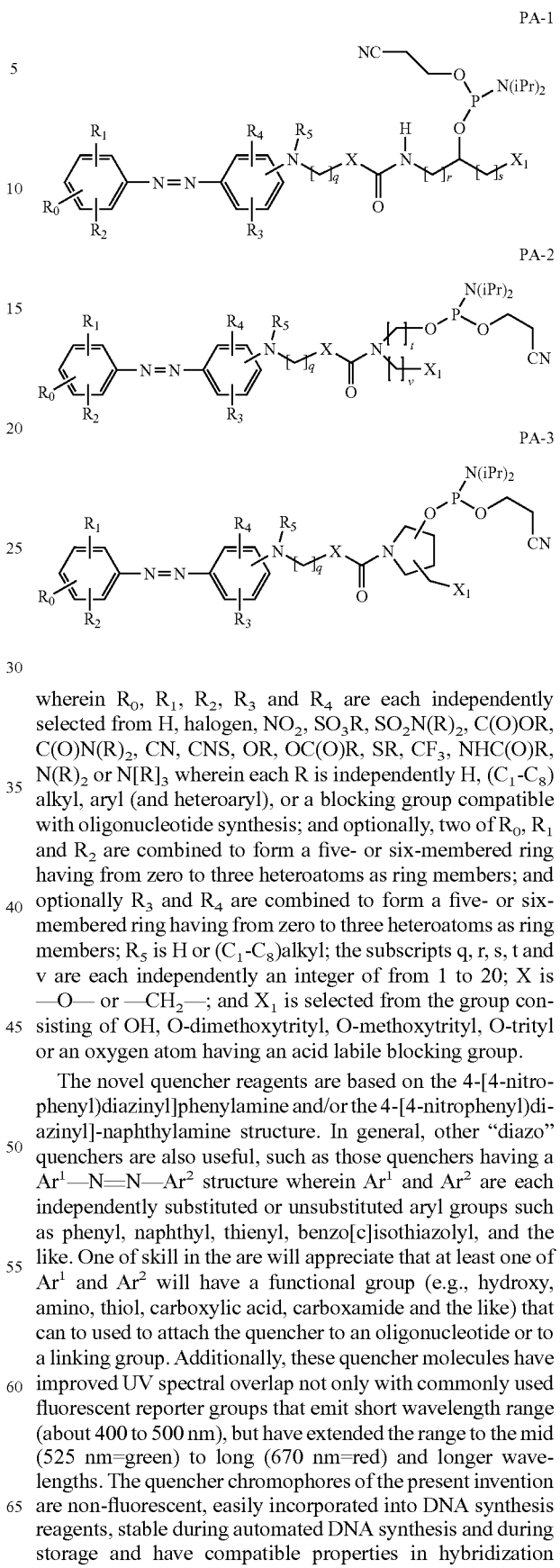

wherein $R_0$, $R_1$, $R_2$, $R_3$ and $R_4$ are each independently selected from H, halogen, NO$_2$, SO$_3$R, SO$_2$N(R)$_2$, C(O)OR, C(O)N(R)$_2$, CN, CNS, OR, OC(O)R, SR, CF$_3$, NHC(O)R, N(R)$_2$ or N[R]$_3$ wherein each R is independently H, ($C_1$-$C_8$) alkyl, aryl (and heteroaryl), or a blocking group compatible with oligonucleotide synthesis; and optionally, two of $R_0$, $R_1$ and $R_2$ are combined to form a five- or six-membered ring having from zero to three heteroatoms as ring members; and optionally $R_3$ and $R_4$ are combined to form a five- or six-membered ring having from zero to three heteroatoms as ring members; $R_5$ is H or ($C_1$-$C_8$)alkyl; the subscripts q, r, s, t and v are each independently an integer of from 1 to 20; X is —O— or —CH$_2$—; and $X_1$ is selected from the group consisting of OH, O-dimethoxytrityl, O-methoxytrityl, O-trityl or an oxygen atom having an acid labile blocking group.

The novel quencher reagents are based on the 4-[4-nitrophenyl)diazinyl]phenylamine and/or the 4-[4-nitrophenyl)diazinyl]-naphthylamine structure. In general, other "diazo" quenchers are also useful, such as those quenchers having a Ar$^1$—N=N—Ar$^2$ structure wherein Ar$^1$ and Ar$^2$ are each independently substituted or unsubstituted aryl groups such as phenyl, naphthyl, thienyl, benzo[c]isothiazolyl, and the like. One of skill in the are will appreciate that at least one of Ar$^1$ and Ar$^2$ will have a functional group (e.g., hydroxy, amino, thiol, carboxylic acid, carboxamide and the like) that can to used to attach the quencher to an oligonucleotide or to a linking group. Additionally, these quencher molecules have improved UV spectral overlap not only with commonly used fluorescent reporter groups that emit short wavelength range (about 400 to 500 nm), but have extended the range to the mid (525 nm=green) to long (670 nm=red) and longer wavelengths. The quencher chromophores of the present invention are non-fluorescent, easily incorporated into DNA synthesis reagents, stable during automated DNA synthesis and during storage and have compatible properties in hybridization assays. Moreover, improved signal to noise ratios are observed with the fluorescent reporter dyes over a more extended wavelength range.

Accordingly, the present invention offers considerable advantages over the use of dabcyl (Nazerenko et al, Nucl. Acids Res., 25:2516-21 (1997)) as a quenching dye.

In another aspect, the "diazo" quenchers above (based on the 4-[4-nitrophenyl)diazinyl]phenylamine and/or the 4-[4-nitrophenyl)diazinyl]-naphthylamine structure, or related structures) are modified with linking groups (or "linkers") that allow not only their easy incorporation into fluorogenic DNA probes during automated DNA synthesis, but also to modulate the wavelength and ability to quench. In a related aspect, phosphoramidite derivatives of these quenchers are provided and are useful for introducing the quencher moieties into oligonucleotides during automated synthesis, or for attaching the quencher moieties to amino-tailed oligonucleotides.

In another related aspect, the novel quencher molecules are introduced into oligonucleotides using pyrazolo[5,4-d]pyrimidine and pyrimidines phosphoramidites containing the quenchers attached at the 3'- and 5'-positions, respectively.

In yet another aspect, the present invention provides a fluorophore-phosphoramidite reagent having the formula:

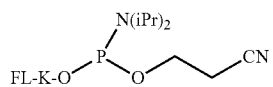

wherein K is a bifunctional linking group; and FL is a fluorophore selected from:

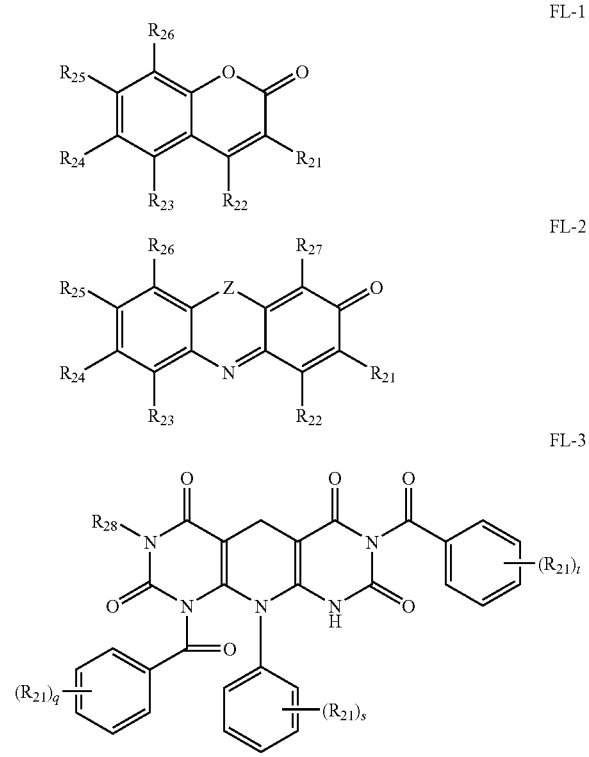

wherein $R_{21}$, $R_{22}$, $R_{23}$, $R_{24}$, $R_{25}$, $R_{26}$ and $R_{27}$ are each substituents independently selected from H, halogen, $NO_2$, $SO_3R$, $SO_2N(R)_2$, $C(O)OR$, $C(O)N(R)_2$, CN, CNS, OR, OC(O)R, SR, $CF_3$, NHC(O)R, $N(R)_2$ and $N[R]_3$ wherein each R is independently selected from H, $(C_1$-$C_8)$alkyl, aryl (and heteroaryl), or a blocking group compatible with oligonucleotide synthesis, and optionally two adjacent groups from $R_{21}$ through $R_{26}$ are combined to form a five- or six-membered ring having from zero to three heteroatoms as ring member, with the proviso that at least one of $R_{21}$ through $R_{27}$ is a bond that attaches said fluorophore to said linking group K; the subscripts q, s and t are integers of from 0 to 5; and $R_{28}$ is selected from H and $(C_1$-$C_8)$alkyl. These fluorescent reagents are compatible with DNA synthesis and are synthesized or selected and converted into phosphoramidite reagents suitable for incorporation onto ODNs. Specifically, violet fluorescent dyes based on the 10-phenyl-1,3,5,7,9,10-hexahydro-pyrimidino[5',4'-5,6]pyridino[2,3-d]pyrimidine-2,4,6,8-tetraone (PPT) structure; red fluorescent dyes based on 7-hydroxyphenoxazin-3-one (resorufin); and blue fluorescent dyes based on the structure of coumarin are incorporated into phosphoramidite reagents, and can be used in preparing compositions provided herein. These fluorescent dyes have excellent properties for multicolor fluorescent analysis in combination with other dyes (e.g., fluorescein). These reagents are useful in a variety of analytical methods that use either direct detection of fluorescence or FRET and related detection formats. In a related aspect of the invention the PPT-, coumarin- and resorufin-based fluorophores (fluorescent dyes) are converted into novel reagents suitable for "post-oligonucleotide-synthesis" covalent attachment at the 5'-end of ODNs. In another aspect, the new fluorescent dyes are incorporated into oligonucleotides using pyrazolo[5,4-d] pyrimidine and pyrimidine phosphoramidites which contain the fluorophores attached at the 3- and 5-positions, respectively.

In still another aspect, the present invention provides a method for hybridizing nucleic acids comprising:

a) incubating a first oligonucleotide with an oligonucleotide probe; and b) identifying a hybridized nucleic acid;

wherein the oligonucleotide probe is a probe as described above. Preferably, the oligonucleotide probe comprises a fluorophore selected from FL-1, FL-2 and FL-3. In one group of embodiments, the method further comprises the step of altering the spatial relationship between the fluorophore and quencher portions of the oligonucleotide probe. In particular, the altering can be a result of hybridization. In other embodiments, the method further comprises releasing the fluorophore from the oligonucleotide probe subsequent to hybridization.

In still other aspects, methods for synthesizing and attaching the novel quenchers to ODN-fluorophore conjugates, with and without a 3'- or 5'-minor groove binder (MGB) are disclosed. In one group of preferred embodiments, these methods utilize solid supports for automated oligonucleotide synthesis with cleavable linkers. One skilled in the art will also appreciate that MGBs can be attached at internal oligonucleotide positions using linking groups or bases suitably modified to incorporate such compounds.

In yet another aspect, a fluorogenic oligonucleotide probe is prepared from a MGB-modified solid support using techniques similar to those described in Lukhtanov et al. Bioconjugate Chem., 7:564-567 (1996). In this aspect, a quencher-phosphoramidite of the invention is added at the first coupling step to the MGB, and a fluorophore (FL) is attached at the final coupling step to the ODN, to yield 5'-FL-ODN-Q-MGB conjugate probe. Alternatively, a 5'-MGB-Q-ODN-FL can be synthesized using a 5'-phosphoramidite rather than a 3'-phosphoramidite.

Still other aspects are directed to methods and compositions that are useful in micro-arrays in nucleic acid-based diagnostic assays which recently have become important in many fields, such as the medical sciences, forensics, agriculture and water quality control. Other related application of the methods and compositions of the present invention are in procedures using arrays of oligonucleotides, such as the array-based analysis of gene expression (Eisen, Methods of Enzym., 303:179-205 (1999)). In these procedures, an ordered array of oligonucleotides or DNAs that correspond to all, or a large fraction of the genes in many organism is used as a platform for hybridization. Microarray-based methods are used in assays to measure the relative representation of expressed RNA species. The quantitation of differences in abundance of each RNA species is achieved by directly comparing two samples by labeling them with spectrally distinct fluorescent dyes and mixing the two probes for simultaneous hybridization to one array.

To the extent the application of the compositions and methods of present invention relates to the detection of nucleic acids, it includes but is not limited to methods where FRET is involved, such as 5'-nuclease, universal energy transfer primers or beacon assays. These methods are usually directed to, but are not limited to the detection of PCR-generated nucleic acid sequences. Some of these methods involve simultaneous detection of more than one nucleic acid sequence in the same assay. Similarly, the invention relates to methods where FRET and related quenching mechanisms are involved in the detection of protein concentration or enzyme activity.

Still other applications of the invention relate to the labeling with luminescent PPT-, coumarin- and resorufin-based dyes of nucleic acids, proteins and other materials including, drugs, toxins, cells, microbial materials, particles, glass or polymeric surfaces and the like, at a reactive group such as an amino, hydroxyl or sulfhydryl group. The present invention may be used in single- and two-step labeling processes. In the two-step labeling process, a primary component, such as an oligonucleotide is labeled with the reagent capable of introducing the novel fluorophore PPT-, coumarin- and resorufin-based dyes, by reaction with a reactive group of the ODN (such as an amine, hydroxyl, carboxyl, aldehyde or sulfhydryl group) and the label is used to probe for a secondary component, such as an oligonucleotide target.

DETAILED DESCRIPTION OF INVENTION

Figure 1:
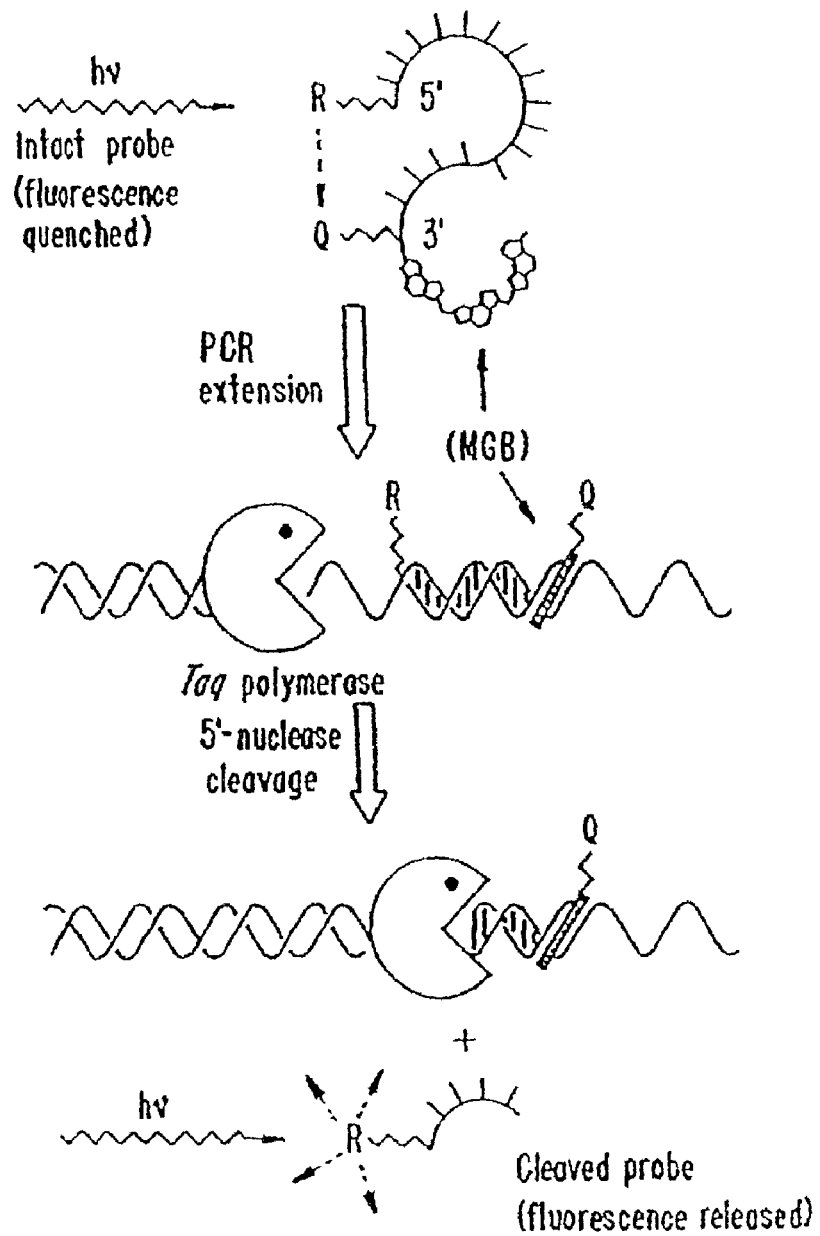
FIG. 1 is a schematic representation of real-time 5'-nuclease PCR assay.

In the reaction schemes and description below (and above), the abbreviations MGB, FL, Q, CPG and ODN refer to "minor groove binder", "fluorescent label" or "fluorophor", "quencher", "controlled pore glass" (as an example of a solid support) and "oligonucleotide" moieties or molecules, respectively, and in a manner which is apparent from context. In certain formulae, the group $[A-B]_n$ is used to refer to an oligonucleotide, modified oligonucleotide or peptide-nucleic acid having 'n' bases (B) and being linked along a backbone of 'n' sugars, modified sugars or amino acids (A).

Unless otherwise stated, the following terms used in the specification and claims have the meanings given below:

The terms "fluorescent label" or "fluorophore" refers to compounds with a fluorescent emission maximum between about 400 and 900 nm. These compounds include, with their emission maxima in nm in brackets, Cy2™ (506), GFP (Red Shifted) (507), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO®-1 (533), JOE (548), BODIPY® 530/550 (550), Dil (565), BODIPY® TMR (568), BODIPY® 558/568 (568), BODIPY® 564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO™-3 (631), R-phycocyanin (642), C-Phycocyanin (648), TO-PRO™-3 (660), TOTO®-3 (660), DiD DilC(5) (665), Cy5™ (670), Thiadicarbocyanine (671), Cy5.5 (694).

The term "linker" refers to a moiety that is used to assemble various portions of the molecule or to covalently attach the molecule (or portions thereof) to a solid support. Typically a linker or linking group has functional groups that are used to interact with and form covalent bonds with functional groups in the ligands or components (e.g., fluorophores, oligonucleotides, minor groove binders, or quenchers) of the conjugates described and used herein. Examples of functional groups on the linking groups (prior to interaction with other components) include —$NH_2$, —$NHNH_2$, —$ONH_2$, —NHC=(O)$NHNH_2$, —OH, or —SH. The linking groups are also those portions of the molecule that connect other groups (e.g., phosphoramidite moieties and the like) to the conjugate. Additionally, a linker can include linear or acyclic portions, cyclic portions, aromatic rings or combinations thereof.

The term "solid support" refers to any support that is compatible with oligonucleotides synthesis, including, for example, glass, controlled pore glass, polymeric materials, polystyrene, beads, coated glass and the like.

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, ($C_1$-$C_8$)alkyl is meant to include methyl, ethyl, n-propyl, 2-propyl, Cert-butyl, pentyl, cyclopentyl, cyclopropylmethyl and the like. For each of the definitions herein (e.g., alkyl, alkenyl, alkoxy, aralkyloxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like The term "aryl" means a monovalent or bivalent (e.g., arylene) monocyclic or bicyclic aromatic hydrocarbon radical of 6 to 10 ring atoms which is unsubstituted or substituted independently with one to four substituents, preferably one, two, or three substituents selected from those groups provided below. The term "aryl" is also meant to include those groups described above wherein one or more heteroatoms or heteroatom functional groups have replaced a ring carbon, while retaining aromatic properties, e.g., pyridyl, quinolinyl, quinazolinyl, thienyl, and the like. More specifically the term aryl includes, but is not limited to, phenyl, 1-naphthyl, 2-naphthyl, thienyl and benzothiazolyl, and the substituted forms thereof.

Substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R", —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Still further, one of the aryl rings (Ar$^1$ and Ar$^2$, below) can be further substituted with another substituted aryl group to extend the resonance ability of the aromatic system, directly or indirectly through groups such as —(CR'=CR')$_n$— and —(C≡C)$_n$—, where n is 0 to 5, increasing the wavelength absorbance maximum.

The prefix "halo" and the term "halogen" when used to describe a substituent, refer to —F, —Cl, —Br and —I.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of "Advanced Organic Chemistry", 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g., $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Futs, Protective Groups in Organic Chemistry, (Wiley, 2nd ed. 1991) and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Optional" or "optionally" in the above definitions means that the subsequently described event or circumstance may but need not occur, and that the description includes instances where the event or circumstance occurs and instances in which it does not. For example, "aryl optionally mono- or di-substituted with an alkyl group" means that the alkyl group may, but need not, be present, and the description includes situations where the aryl group is mono- or di-substituted with an alkyl group and situations where the aryl group is not substituted with the alkyl group.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

General

The invention provides below a number of reagents that are useful in preparing labeled oligonucleotides, particularly for the preparation of FL-ODN-Q-MGB conjugates. Additionally, these fluorophore-oligonucleotide-quencher-minor groove binder conjugates can be in a linear arrangement (as suggested by the formula) or in a branched arrangement wherein the quencher (O) and the minor groove binder (MGB) are attached to a linking group that serves to join ODN, Q and MGB. Both arrangements are meant to be included when the linear abbreviation (FL-ODN-Q-MGB) is used. Additionally, FL, Q and MGB can independently be attached at the 3'-, 5'- or internal positions of the oligonucleotide, so long as such attachment does not interfere with the quenching mechanisms of the conjugate.

Quencher Reagents for Oligonucleotide Synthesis

In one aspect, the present invention provides quencher reagents for the oligonucleotide synthesis having the formula:

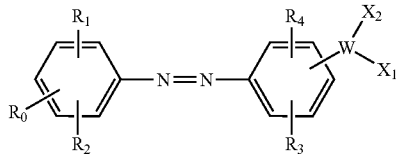

wherein W is a linking group having from 3 to 100 main chain atoms selected from C, N, O, S, P and Si and can be acyclic, cyclic or aromatic or combinations thereof; $X_1$ is H, $(C_1-C_{12})$ alkyl, aryl, heteroaryl, protected or unprotected functional group (e.g., a hydroxy, amino or carboxylic acid or ester that optionally is protected with a suitable protecting group as are known to those of skill in the art); $X_2$ is any phosphorus coupling moiety used in oligonucleotide synthesis, for example, a phosphoramidite of the formula O—P(N(iPr)$_2$)(OCH$_2$CH$_2$CN), or alternatively, a linking group attached to a solid support of the formula O—C(=O)Z-solid support wherein Z is 1 to 30 main chain atoms in length wherein the main chain atoms are selected from C, N, O, P, and S, and Z can include acyclic, cyclic or aromatic groups or combinations thereof; and $R_0$, $R_1$, $R_2$, $R_3$ and $R_4$ are independently selected from the group consisting of H, halogen, NO$_2$, SO$_3$R, SO$_2$N(R)$_2$, C(O)OR, C(O)N(R)$_2$, CN, CNS, OR, OC(O)R, SR, CF$_3$, NHC(O)R, N(R)$_2$ or N[R]$_3$ wherein each R is independently H, $(C_1-C_8)$alkyl, aryl (and heteroaryl), or a cleavable linking group that is attached to a solid support, or a blocking group compatible with oligonucleotide synthesis and optionally, two of $R_0$, $R_1$ and $R_2$ are combined to form a five- or six-membered ring having from zero to three heteroatoms as ring members; and optionally $R_3$ and $R_4$ are combined to form a five- or six-membered ring having from zero to three heteroatoms as ring members. For those embodiments in which $R_3$ and $R_4$ are combined to form a fused ring system, the linking group W can be attached to either the phenyl ring (as indicated above) or to the ring formed by $R_3$ and $R_4$. Additionally, for those embodiments herein, where two alkyl groups are attached to a nitrogen atom, forming a dialkylamino substituent, the alkyl groups can be the same or different.

The linking group W can be essentially any linking group that has from 3 to 100 atoms other than hydrogen atoms, selected from C, N, O, S, P and Si, and is cyclic, acyclic, aromatic or a combination thereof. Additionally, the linking groups will be sufficiently robust so that they are stable to reaction conditions used in oligonucleotide synthesis, as well as the protection/deprotection chemistries used to prepare the conjugates described in more detail below. U.S. Pat. No. 5,512,667 describes a prolinol linker, while U.S. Pat. Nos. 5,451,463 and 5,141,813 describe acyclic linkers that can be used in the present invention. Additionally, U.S. Pat. Nos. 5,696,251, 5,585,422 and 6,031,091 describe certain tetrafunctional linking groups that can be modified for use in the present invention, or used to prepare compositions in which, for example, two fluorophores are present in the conjugate. Functional groups on linkers include primary and secondary nitrogen, primary and secondary OH and —SR Dimethoxytrityl Protected Quencher Phosphoramidites One particular type of reagent disclosed herein are phosphoramidites that bear the quencher molecule (Q) as well as a dimethoxytrityl (DMTr) (methoxytrityl, trityl or the like acid labile blocking group) protected primary alcohol that provides an attachment point for the growing oligodeoxynucleotide (ODN) chain during subsequent oligonucleotide synthesis. Examples of these reagents are depicted in Formulas 1, 2, and 3, and in Reaction Schemes 1 and 2.

In Reaction Scheme 1 the starting compound is a substituted 4-(phenyldiazenyl)phenylamine 1 that has a primary hydroxyl group. Such starting materials are either commercially available or can be synthesized in accordance with methods known in the art. For example, 4-nitrobenzenediazonium salt can be reacted with 2-(2-chloroanilino)ethanol to yield 2-[2-chloro-4-(4-nitrophenylazo)anilino]ethanol (see, U.S. Pat. No. 2,264,303). 2-[2-chloro-4-(4-nitrophenylazo)anilino]ethanol is within the scope of compound 1 as depicted in Reaction Scheme 1.

Other examples of commercially available starting materials (or of their precursors) are: 2-(ethyl{4-[(4-nitrophenyl)diazenyl]phenyl}amino)ethan-1-ol and 2-(ethyl{4-[(2-methoxy-4-nitrophenyl)diazenyl]phenyl}amino)ethan-1-ol.

Returning to Reaction Scheme 1, compound 1 is reacted with p-nitrophenylchloroformate to yield the carbonate 2.

Reaction of 2 with substituted pyrrolidinediols yields a diol intermediate 3. The pyrrolidinediol is a trifunctional reagent that has an amino, a primary and a secondary hydroxyl group. An example of a pyrrolidinediol as well as examples of other trifunctional reagents having an amino, primary and a secondary hydroxyl group, are described in U.S. Pat. No. 5,512,667. The diol 3 is reacted first with dimethoxytrityl chloride (DMTrCl) to block the primary hydroxyl group of the trifunctional reagent and yield intermediate 4. The intermediate 4, still having a free secondary hydroxyl group in the trifunctional reagent, is then reacted with 2-cyanoethyl diisopropylchloro-phosphoramidite to give the dimethoxytrityl protected phosphoramidite reagent 5. In the compounds shown in Reaction Scheme 1 the symbols are defined as follows: $R_0$, $R_1$, $R_2$, $R_3$ and $R_4$ are independently H, halogen, $NO_2$, $SO_3R$, $SO_2N(R)_2$, $C(O)OR$, $C(O)N(R)_2$, CN, CNS, OR, $OC(O)R$, SR, $CF_3$, $NHC(O)R$, $N(R)_2$ or $N[R]_3$ wherein each R is independently H, $(C_1-C_8)$alkyl, aryl (and heteroaryl), or a blocking group compatible with oligonucleotide synthesis; $R_5$ is H, $(C_1-C_8)$alkyl, aryl (and heteroaryl); $R_6$ is a linking group having from 1 to 15 main chain atoms selected from C, N, O, P and S, preferably a $CH_2$ or $CH_2CH_2$ group; and q=1 to 20. The dimethoxytrityl protected phosphoramidite reagent 5 is suitable for attachment to oligonucleotides in steps otherwise known in routine ODN synthesis.

REACTION SCHEME 1

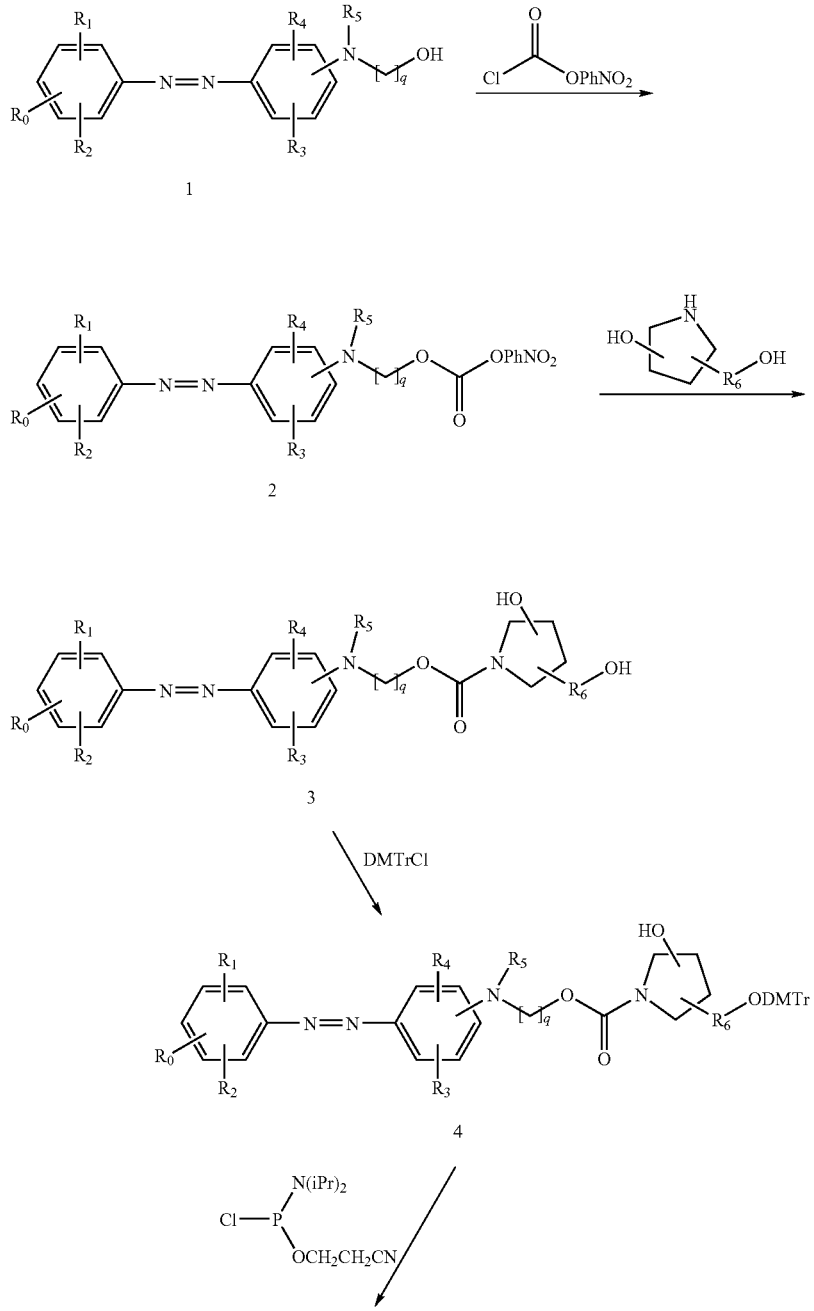

-continued

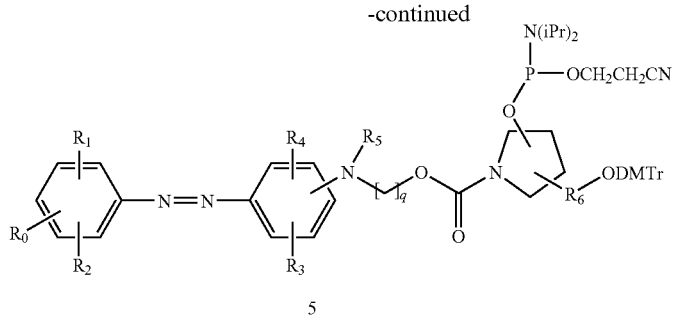

5

The reactions described in Reaction Scheme 1 can be applied to the preparation of other activated quenchers starting with other linking groups having an amino and two hydroxyl groups. Accordingly, the phosphoramidites of Formula 1 and Formula 2 can be synthesized, wherein q, $R_0$, $R_1$, $R_2$, $R_3$, $R_4$ and $R_5$, are as defined above; r and s are each independently integers from 1 to 20; X is —O— or —CH$_2$—; and t and v are each independently integers from 1 to 20.

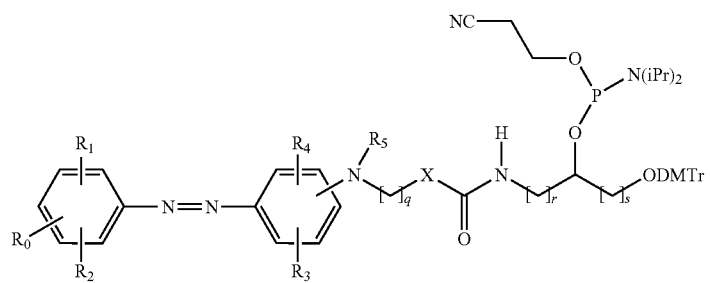

Formula 1

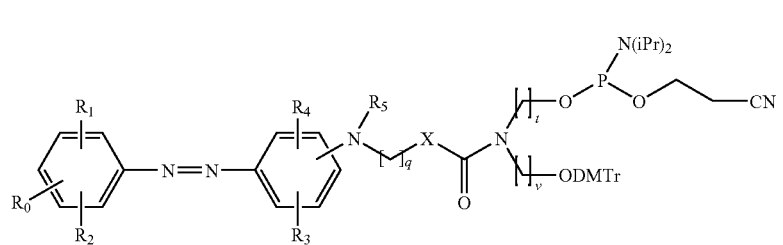

Formula 2

Reaction Scheme 2 discloses the synthesis of another exemplary phosphoramidite reagent 10 bearing the substituted 4-(phenyldiazenyl)-phenylamine quencher moiety and including a pyrrolidinediol linking group. In this synthetic scheme the starting material is a substituted 4-(phenyldiazenyl)-phenylamine compound 6 that has a free carboxyl group. Compound 6 (commercially available or made in accordance with the chemical literature) is reacted with pentafluorophenyl trifluoroacetate to make an active ester 7, which is thereafter reacted to couple the substituted 4-(phenyldiazenyl)-phenylamine moiety to the ring nitrogen of a pyrrolidinediol moiety having a free primary and a free secondary hydroxyl group, yielding compound 8. Treatment of 8 with DMTrCl followed by reaction with 2-cyanoethyl diisopropylchlorophosphoramidite gives the dimethoxytrityl protected phosphoramidite reagent 10. In Reaction Scheme 2 the symbols are defined the same as in Reaction Scheme 1.

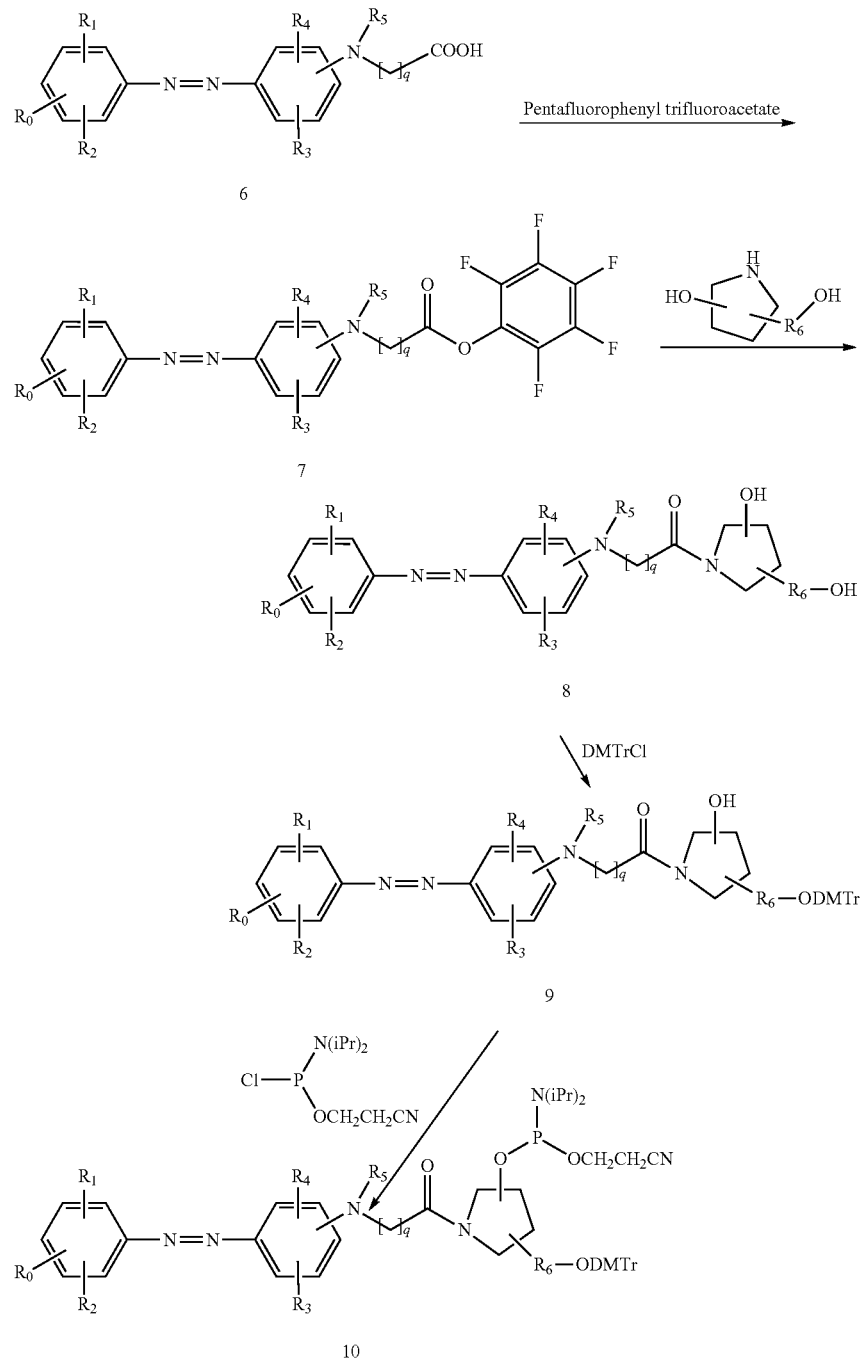

In still another example, using the reactions described in Reaction Scheme 2, starting with a substituted 4-(phenyldiazenyl)phenylamine (compound 6) and using a non-cyclic reagent (having an amino and two hydroxyl functions) instead of the pyrrolidinediol shown in Scheme 2, the dimethoxytrityl protected phosphoramidite of Formula 3 is synthesized, where q, $R_0$, $R_1$, $R_2$, $R_3$, $R_4$, $R_5$ and $R_6$ are defined as above and t and v independently are 1 to 20.

Formula 3

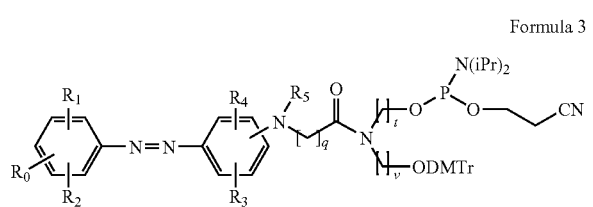

Returning to Reaction Scheme 2, one of skill in the art will understand that certain intermediate compounds such as compound 7 have utility in the post-synthetic modification of oligonucleotides or oligonucleotide conjugates. For example, compound 7 and related activated esters can be used to modify a reactive functional group such as an aminoalkyl group post synthetically. Reagents useful for such modification have the formula provided below as Formula 3A:

Formula 3A

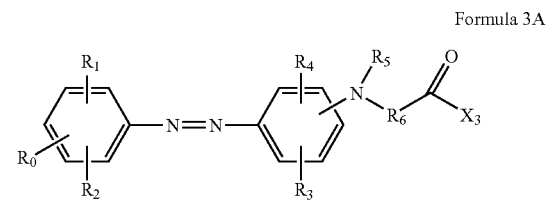

wherein the symbols $R_0$, $R_1$, $R_2$, $R_3$, $R_4$, $R_5$ and $R_6$ are as defined above and $X_3$ is a leaving group such as a pentafluorophenoxy, succinimidyl or other similar group that renders the carbonyl moiety more reactive toward nucleophiles (e.g., compounds with reactive groups such as —$NH_2$, —$NHNH_2$, —$ONH_2$, —SH and —$NHC(O)NHNH_2$).

Quenchers Attached to Solid Support through (or Similarly) Protected Linker, Suitable for ODN Synthesis In a related aspect, a second class of compounds or reagents suitable for introducing the quencher molecules into ODNs are provided that have an attached solid support of the type used for ODN synthesis (for example controlled pore glass (CPG)), and a linker attaching the quencher to the solid support. The linker has a hydroxyl function that is protected, usually by a dimethoxytrityl group which is removed during the synthesis when the first nucleotide is attached to the linker. Generally, the same quencher/linker intermediates described above in Reaction Scheme 1 can also be used to prepare these reagents (using, for example, CPG beads) having the exemplary structure 12, shown in Reaction Scheme 3.

REACTION SCHEME 3

4

1) Succinic Anhydride
2) Pentafluorophenyl Trifluoracetate

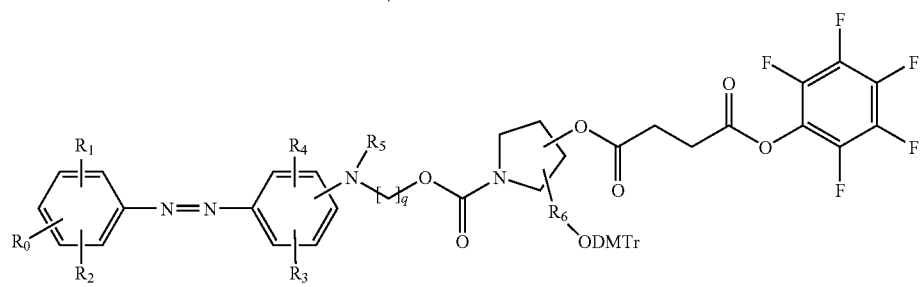

11

CPG~~NH₂

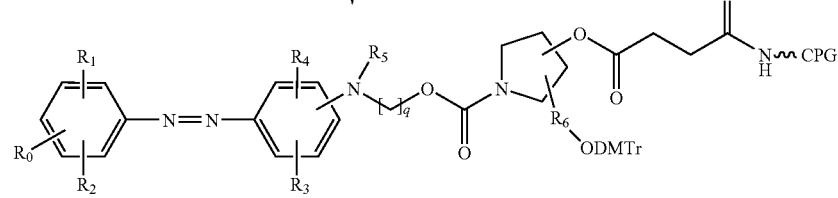

12

The secondary hydroxyl group of the intermediate 4 (shown in Scheme 1) is reacted with succinic anhydride, and thereafter pentafluorophenyl trifluoroacetate to provide the active ester 11. The active ester 11 is then reacted with the free amino group attached to the solid support (CPG bead) to provide the modified solid support 12. Whereas the exemplary modified solid support 12 includes the "linker" derived from pyrrolidine diol, it will be readily understood by those skilled in art that analogous modified solid supports including other linkers and related structures, such as the linkers shown in Formulas 1, 2 and 3 can also be made substantially in accordance with Reaction Scheme 3, resulting in modified solid support compositions including the quencher moiety, such the ones shown in Formula 4 and Formula 5.

The modified solid support compositions including the quencher moiety of structure 12 and of Formula 4 and 5 are useful for preparing 3'-quencher conjugates, which in turn allow the introduction of a fluorophore at the 5'-end with the appropriate phosphoramidite, or post-synthetically with a fluorophore containing a reactive group. In Reaction Scheme 3 and in Formula 4 and Formula 5 the symbols are defined as above. It should be understood that other solid supports (such as polystyrene) and other cleavable linker systems (in addition to the succinate linker shown) can also be prepared in accordance with these general teachings and are also within the scope of the invention.

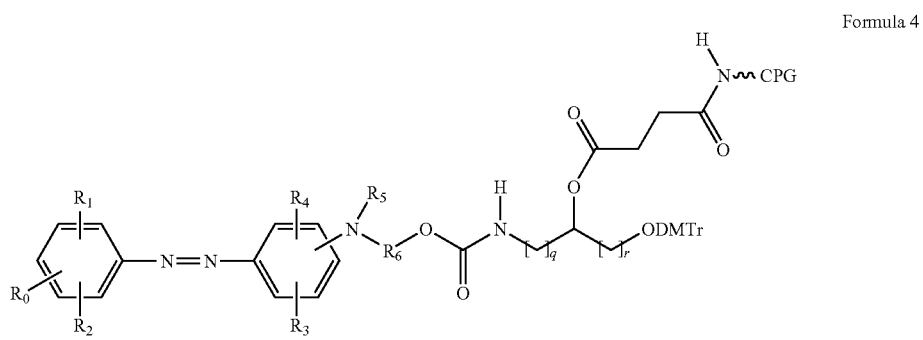

Formula 4

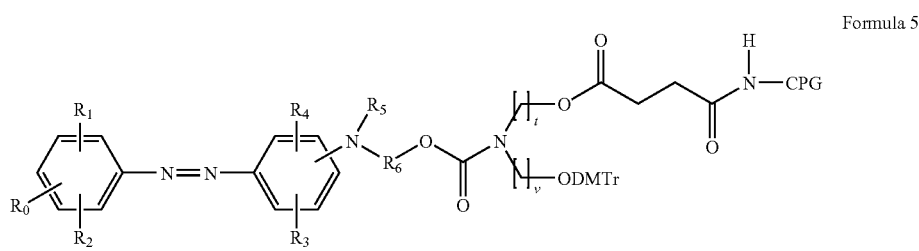

Formula 5

The reaction schemes provided above can be adapted by one of skill in the art to incorporate a variety diazo compounds. Particularly useful are those diazo compounds shown in the table below (wherein each Ra and Rb independently represent a functional group or a protected functional group for attaching the quencher to a linking group or conjugate).

TABLE 1

| Structure | $\lambda_{max}$ nm | $\epsilon$ M$^{-1}$cm$^{-1}$ |
|---|---|---|
| 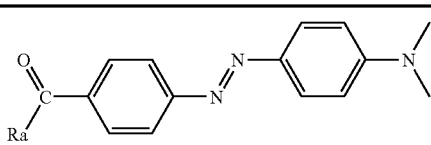 | 453 | ~40,000 |
| 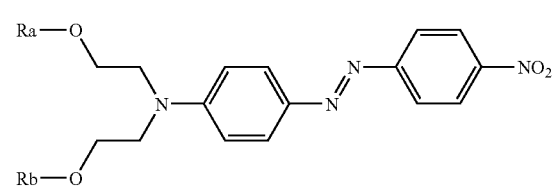 | | |
| 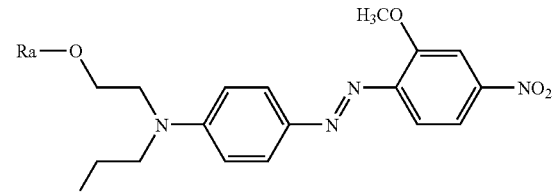 | | |
| 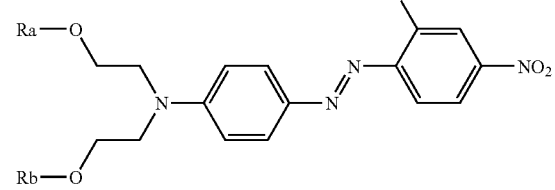 | 522 | ~40,000 |
| 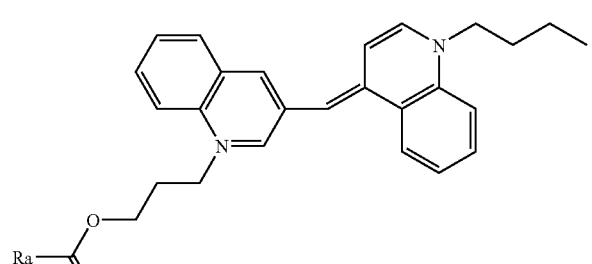 | 538 | ~40,000 |
| 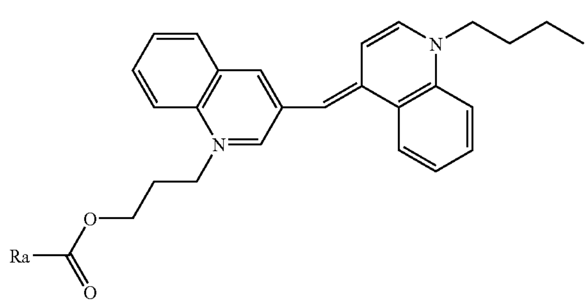 | 595 | >150,000 |

A shift absorbance $\lambda_{max}$ to longer wavelength was observed by increasing the conjugation (e.g., adding more rings and or double bonds) in addition to substitutions.

The following Table contains additional structures of quenchers that can be readily modified to, for example, the related structure having suitable functional groups for introduction into probes, based on the known chemical reactions cited (see, for example, Thiel et al., *J. fur prakt. Chemie*, 328:497-514 (1986); U.S. Pat. Nos. 4,324,721 and 4,054,560; Timm, *Melliand Textilberichte*, 9:1090-1096 (1969); Hallas, J. S. D. C. 285-294 (1979); Beyer et al., *J Prakt. Chem.*, 24:100-104 (1964); Hutchings et al., *Chem. Europ. J.* 3:1719-1727 (1997) and Morley et al., *J. Phys. Chem. A.*, 102:5802-5808 (1998); Haak et al., *J. Chem. Res. Miniprint* 10.2701-2735 (1998) and Ruggli et al., *Helv. Chim. Acta*, 26:814-826 (1943). Additional structures with different combinations of substituents at various positions can be prepared based on compounds and methods known in the dye chemistry field (summarized in the Color Index, Issue 3 on CDD-ROM, pages 4009-4324; Society of Dyers and Colourists, Bradford, England; http://www.sdc.org.uk).

TABLE 2

| Structure Literature | $\lambda_{max}$ nm; $\epsilon$ M$^{-1}$cm$^{-1}$; Solvent | Linker-Modified Structure |
|---|---|---|
| | 464 | |
| | 440 | |
| | 540; 40,000 MeOH | |
| | 549 37,000 EtOH | |
| | 590 48,978 CHCl$_3$ | |

TABLE 2-continued

| Structure Literature | $\lambda_{max}$ nm; $\epsilon$ M$^{-1}$cm$^{-1}$; Solvent | Linker-Modified Structure |
|---|---|---|
| | 601 40,738 CHCl$_3$ | |
| | 623 48,000 CHCl$_3$ | |
| | 656 100,000 CHCl$_3$ | |
| | 656 53,043 | |

TABLE 2-continued

| Structure Literature | λ$_{max}$ nm; ε M$^{-1}$cm$^{-1}$; Solvent | Linker-Modified Structure |
|---|---|---|
| | 598 | |
| | 582 | |
| | 652 | |
| | 554 50,000 | |
| | 673.5 | |

TABLE 2-continued

| Structure Literature | $\lambda_{max}$ nm; $\epsilon M^{-1} cm^{-1}$; Solvent | Linker-Modified Structure |
|---|---|---|
| [structure] | 809 | [structure] |
| [structure] | 592<br>46,000 | [structure] |
| [structure] | 601<br>51,000 | [structure] |
| [structure] | 623<br>48,000 | [structure] |
| [structure] | 632 Predicted | [structure] |

The quenchers above cover the range from about 400-800 nm, and many demonstrate improved quenching when attached to a MGB. While the modified versions illustrate —N(CH$_2$CH$_2$OH)$_2$ as a preferred linking group to be used to couple the quencher to oligonucleotides, MGB or solid support, example of other suitable linkers are known in the art or are provided herein.

Minor Groove Binder Quencher Reagents for Oligonucleotide Synthesis

In another aspect of the invention, a minor groove binder (MGB) is attached to a solid support (e.g., controlled pore glass (CPG)) through a cleavable linker. A quencher moiety, based on the Ar$^1$—N=N—Ar$^2$— type of structure, is attached through a linker molecule (W) to the MGB. The linker molecule also contains a hydroxyl group blocked with DMTr (or like) blocking group. Accordingly, the present invention provides modified solid supports having the structure:

wherein the shaded sphere represents any solid support that is useful in oligonucleotide synthesis, L represents a cleavable linker, MGB is a minor groove binder and the subscript r is 0 or 1; W is a linking group that has from 3 to 100 atoms other than hydrogen atoms, selected from C, N, O, S, P and Si, and is cyclic, acyclic or a combination of acyclic and cyclic, Q is a quencher and the subscript m is 0 or 1, indicating that the quencher is optional, and —O-J$_1$ is a hydroxyl group blocked with protecting group (preferably a dimethoxytrityl protecting group). After removal of the protecting group, an oligonucleotide can be synthesized on an automated oligonucleotide synthesizer by step-wise attachment of nucleotide units to the hydroxyl group. A fluorophore can then be introduced at the 5'-end with the appropriate phosphoramidite, or post-synthetically with a fluorophore containing a reactive group, to yield an ODN having an attached fluorescent moiety (FL), quencher (Q) and MGB (FL-ODN-Q-MGB). One of skill in the art will appreciate from the schemes herein, that while the FL-ODN-Q-MGB conjugates may be described in a linear fashion, that the quencher (Q) and minor groove binder (MGB) can also be attached to a common linking group and provide a "branched" structural formula as illustrated below.

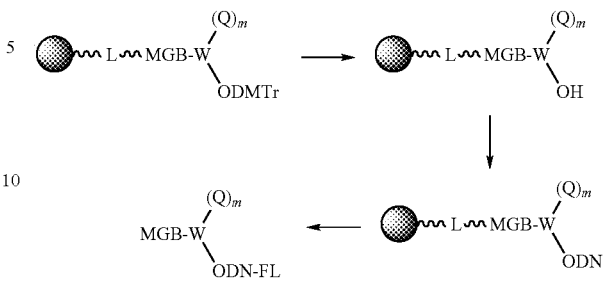

In general, the synthesis of MGBs and their attachment to ODNs is well known (see for example U.S. Pat. No. 5,801,155; and copending applications Ser. Nos. 09/539,097 and 09/141,764). A 5'-MGB-Q-ODN-FL is obtained through synthesis using a 5'-phosphoramidite instead of a 3'-phosphoramidite. 5'-Phosphoramidites are commercially available and modified base 5'-phosphoramidites can be prepared using well-known methods.

In a preferred embodiment the MGB is 3-{[3-(pyrrolo[4,5-e]indolin-7-ylcarbonyl)pyrrolo[4,5-e]indolin-7-yl]carbonyl}pyrrolo[3,2-e]indoline-7-carboxylic acid (DPI$_3$). The synthesis of the covalently bound "aggregate" FL-ODN-Q-DPI$_3$ requires five phases, described below. The first phase, shown in Reaction Scheme 4, is the synthesis of an intermediate, 2-(4-nitrophenyl)ethyl 3-(pyrrolo[4,5-e]indoline-7-carbonyl)pyrrolo[4,5-e]indoline-7-carboxylate (DPI$_2$-NPC) 17. The second phase, shown in Reaction Scheme 5, is the synthesis of Q-DMTr-DPI-CO$_2$PFP 24 where a quencher is coupled through a linker to a pyrrolo[3,2-e]indoline-7-carboxylic acid unit (DPI). Here, and in the reaction schemes PFP stands for the pentafluorophenyl or pentafluorophenyloxy group, as the context requires. In the third phase, shown in Reaction Scheme 6, DMTr-Q-DPI$_3$-PFP 25a is synthesized from 17 and 24. In the fourth phase 25a is coupled to CPG to yield a DMTr-Q-DPI$_3$-CPG 29, and in the fifth phase 29 is used on an automated oligonucleotide synthesizer to stepwise attach nucleotide units and to provide, after removal from the CPG, the product FL-5'-ODN-3'-Q-DPI$_3$ 30.

The fourth and fifth phases of these synthetic process are shown in Reaction Scheme 7. Experimental conditions for this sequence (phases 1 through 5) are described below.

REACTION SCHEME 4

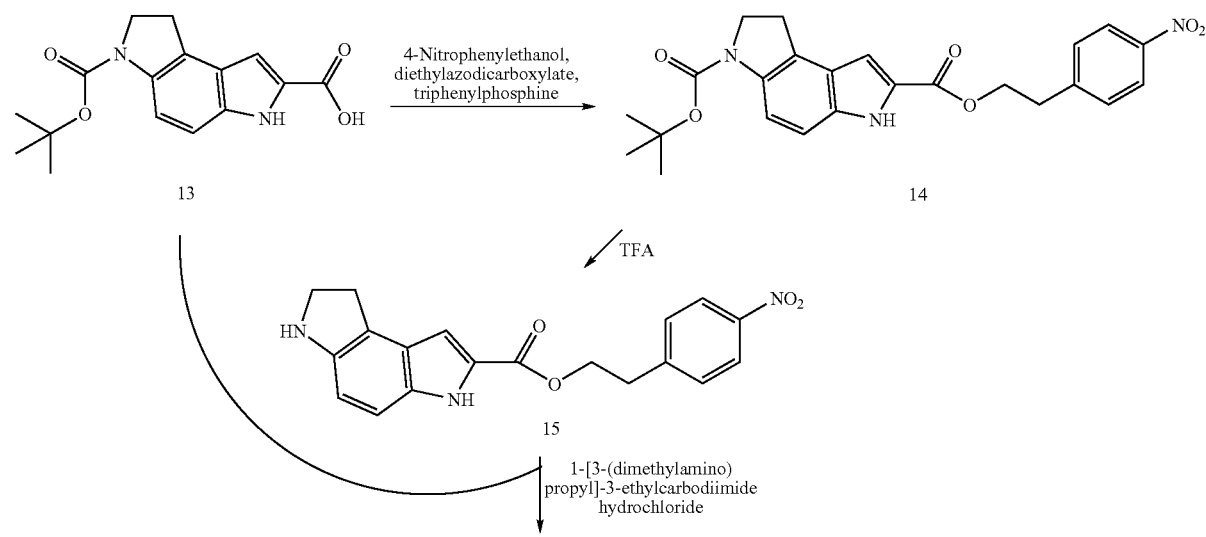

-continued
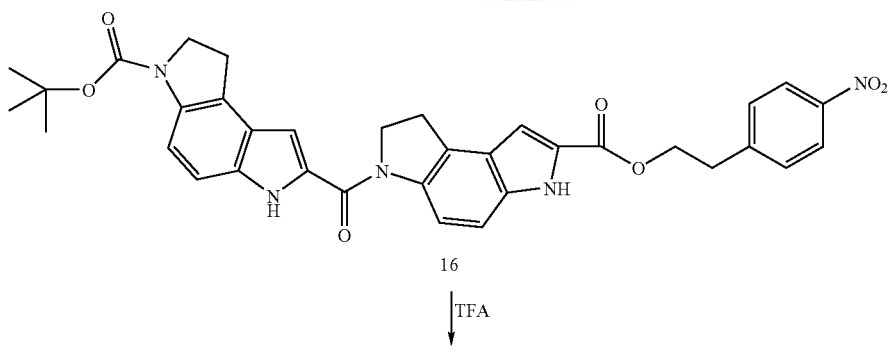
16
↓ TFA
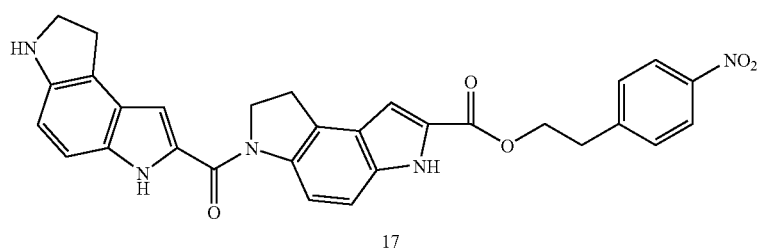
17
REACTION SCHEME 5
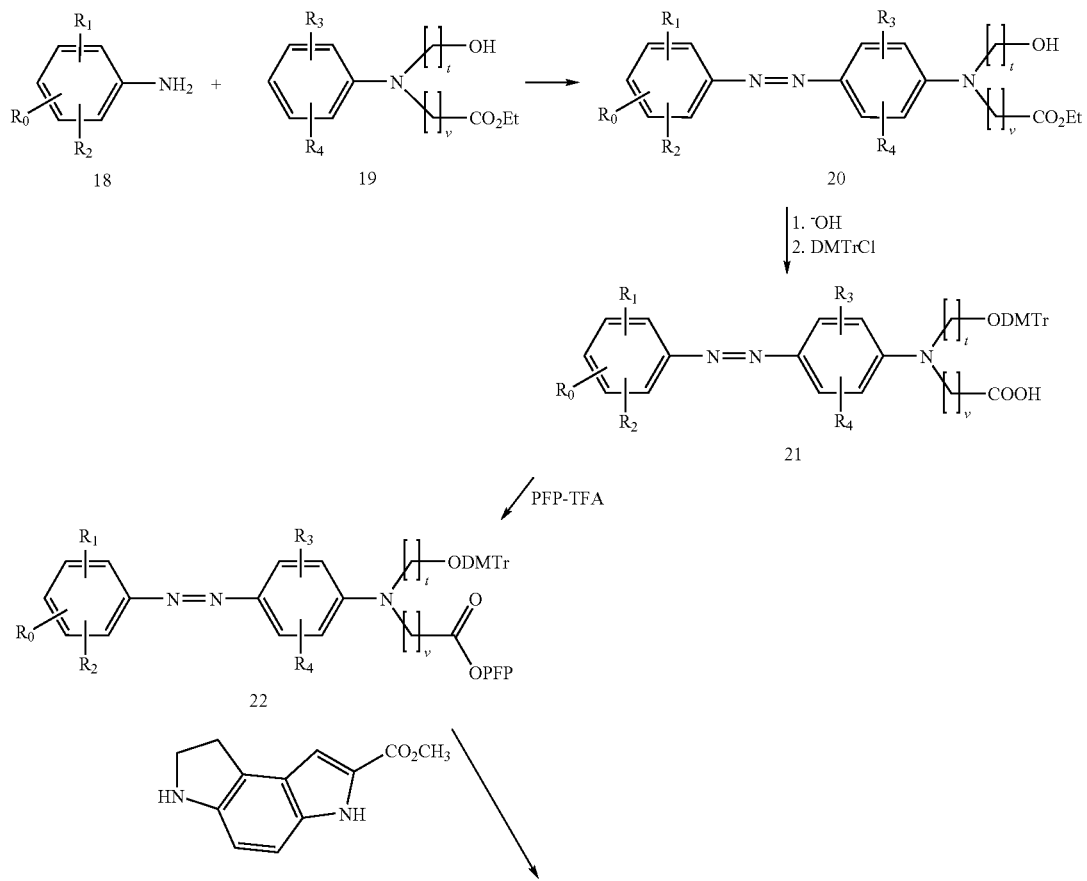

-continued
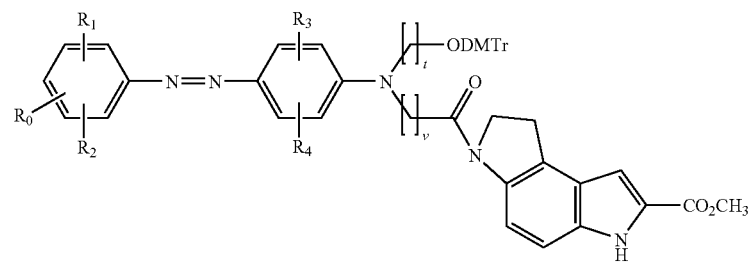
23
1. ⁻OH
2. PFP-TFA
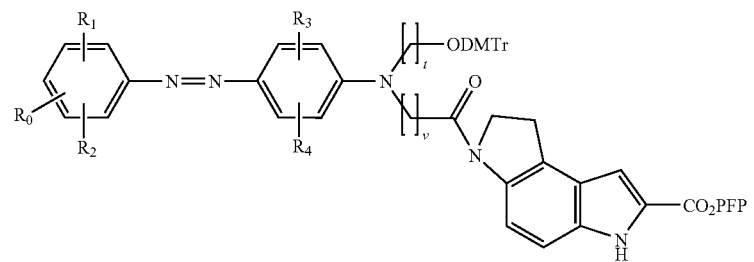
24
REACTION SCHEME 6
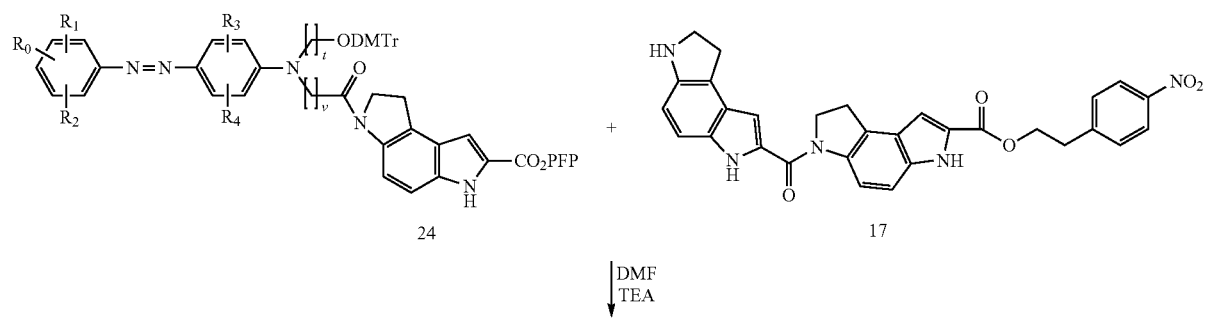
DMF
TEA -continued
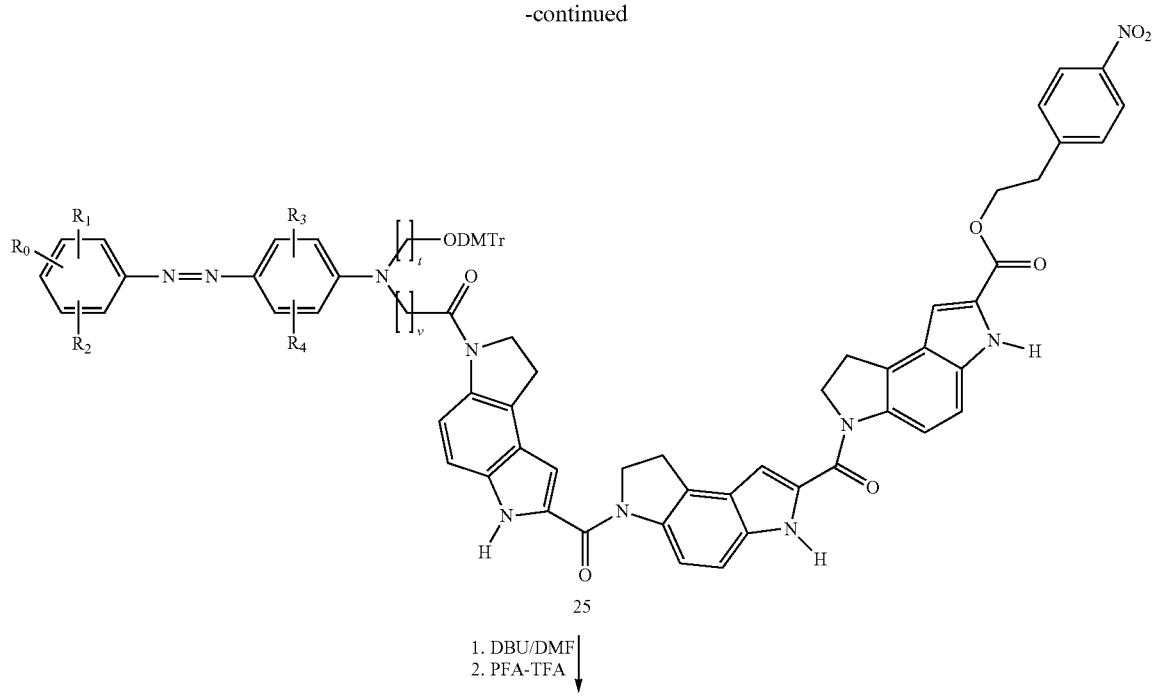
25
1. DBU/DMF
2. PFA-TFA
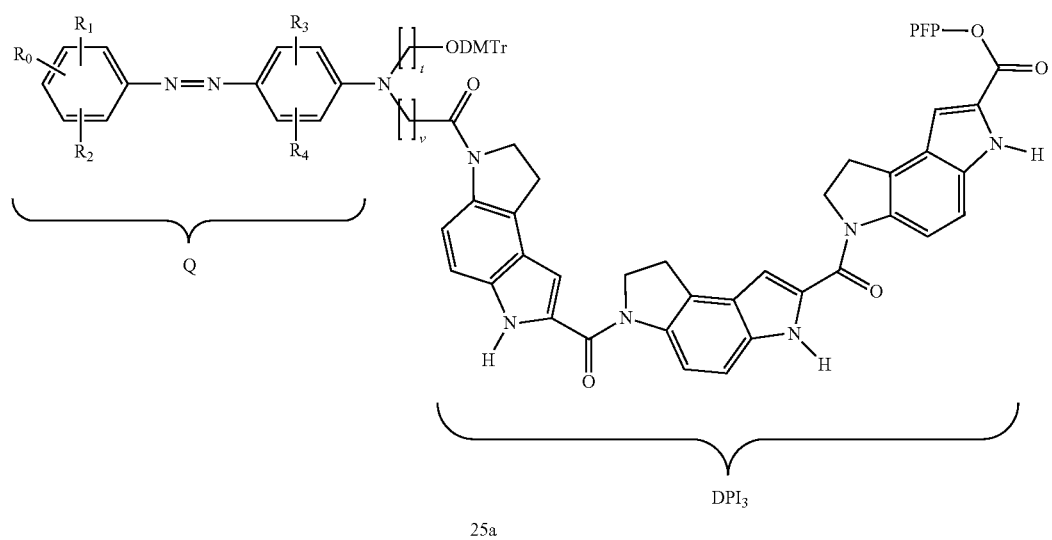
25a REACTION SCHEME 7
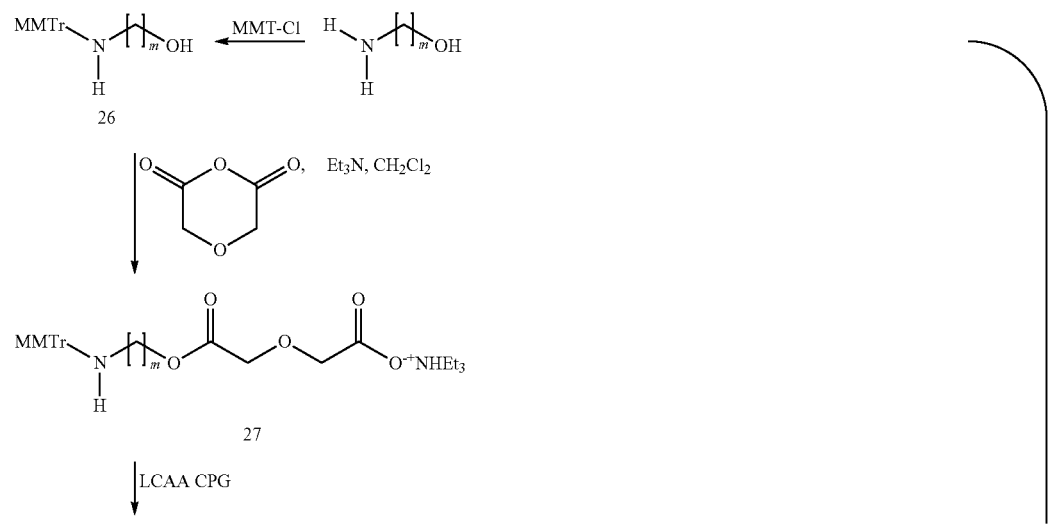
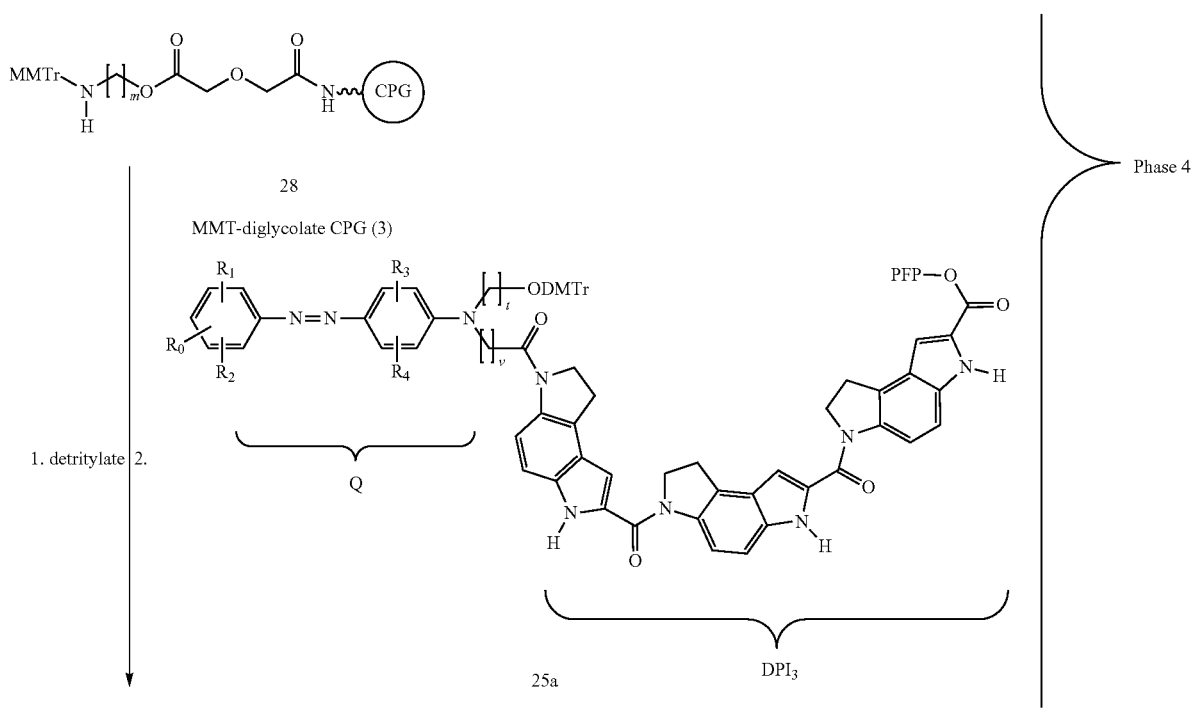

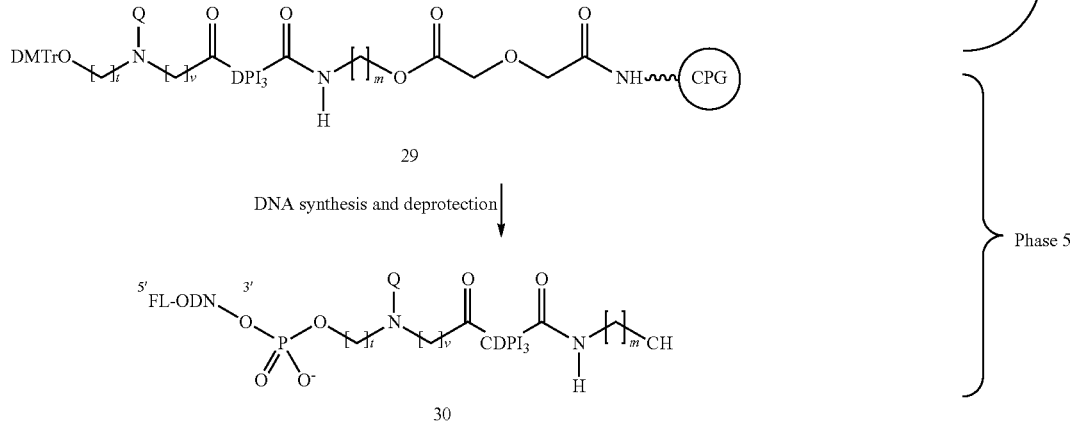

Describing these phases or reactions now in more detail, the Q-DPI₃ moiety 25 (phase 3) is synthesized by the reaction of two intermediates, 17 and 24 as shown in Reaction Scheme 6. The first intermediate DPI₂-NPE 17 is made as shown in Scheme 4. DPI-tBoc 13 was reacted with p-nitrophenylethanol in the presence of diethylazodicarboxylate (DEAD) and triphenylphosphine to yield the di-ester 14. Compound 14 was then treated with trifluoroacetic acid (TFA) to yield 15, and conjugated with 13 in the presence of 1-[3-(dimethylamino)propyl]-3-ethylcarbodiimide hydrochloride to give the 4-nitrophenyl ester of DPI₂ 16 in good yield. Reaction of 16 with TFA gives the p-nitrophenethyl ester of DPI₂ 17. The second intermediate DPI-Q 24 (phase 2) is synthesized as shown in Reaction Scheme 5. A substituted nitroaniline 18 (available commercially or in accordance with the chemical literature) is diazotized in the presence of nitrous acid and is coupled to a substituted aniline 19 (available commercially or in accordance with the chemical literature) to form the azo intermediate quencher molecule 20. Alkaline hydrolysis of the ethyl ester 20 followed by the treatment with DMTrCl gives the DMTr-Q 21, that is subsequently activated with pentafluorophenyl trifluoroacetate to yield 22. Reaction of 22 with DPI-methyl ester gives the Q-DMTr-DPI methylester 23. Compound 23 is then treated with alkali to hydrolyze the methyl ester and then activated with PFP-TFA to yield Q-DMTr-DPI PFP ester 24. In Reaction Scheme 5 the symbols $R_0$, $R_1$ through $R_4$, v and t are defined as above.

Referring now to Reaction Scheme 6 (where the symbols are also defined as above), DMTr-Q-DPI₃-PFP 25a (third phase) is synthesized first by reacting the activated quencher 24 (DMTr-Q-DPI PFP) with DPI₂-NPC 17 to yield the p-nitrophenylethyl ester 25, which is converted to the active ester 25a, first by treatment with base such as 1,8-diazabicyclo [5.4.0]undec-7-ene (DBU) to remove the p-nitrophenylethyl moiety and then treatment with 2,3,4,5,6-pentafluorophenyl trifluoroacetate (PFP-TFA).

The synthesis of DMTr-Q-DPI₃-CPG 29 (phase four) is shown in Reaction Scheme 7. In this synthetic sequence the improved quencher molecule becomes attached through a cleavable diglycolate linker to controlled pore glass beads (CPG). Specifically, aminopropanol, or a homolog thereof, is reacted successively with monomethoxytrityl chloride (MMTr-Cl) and then with diglycolic anhydride to form MMT-blocked aminopropanol 26 (or homolog) and MMT-diglycolate 27, respectively. The symbol m is defined as an integer having the values 2 to 20. For the presently preferred aminopropanol, m is 3. The remaining symbols in this scheme are defined as above. Reaction of 27 with long chain aminoalkyl CPG in the presence of activating agents (HOBT and HBTU), yields the MMT-diglycolate-CPG 28, that is converted after detritylation and reaction with 25a to DMTrO-Q-DPI₃-CPG 29.

In phase 5, still shown in Reaction Scheme 7, oligonucleotide synthesis is performed with the aid of an automated DNA synthesizer, and a fluorophore is attached at the 5'-end of the ODN, using either a fluorophore-phosphoramidite or a fluorophore containing a reactive group, to yield the FL-ODN-Q-DPI₃ 30 conjugate.

The FL-ODN-Q-DPI₃ 30 conjugate can also be synthesized by an alternative synthetic route which is not specifically illustrated in the reaction schemes. In this alternative route DPI₃-methyl ester (obtained in accordance with Boger et al., J. Org. Chem., 52:1521-(1987)) is first reacted with compound 22 and then with alkali to give Q-DPI₃-methyl ester and Q-DPI₃-COOH, respectively. The latter compound is then activated with pentafluorophenyl trifluoroacetate, to yield 25a, which is then used in the reactions shown in Scheme 7, to yield 30.

Fluorophore Reagents

Fluorescent dyes which have emission wavelengths shorter than the green fluorescent dye FAM have utility in DNA probe based assays described below. Generally, these dyes have been less popular for use in probes since excitation with laser light sources is less feasible than with longer wavelengths.

In one group of embodiments, the present invention provides fluorophore phosphoramidite reagents that are useful in introducing a suitable fluorophore into a oligonucleotide probe, the reagents having the formula:

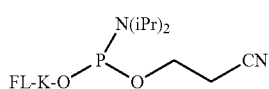

wherein K is a linking group; and FL is a fluorophore selected from the group consisting of:

FL-1

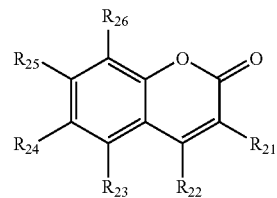

FL-2

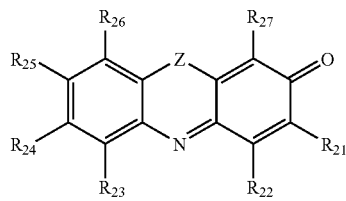

FL-3

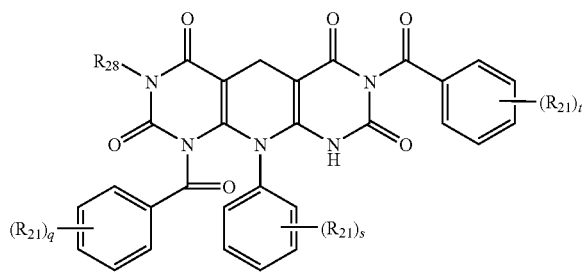

wherein Z is O or S and each of $R_{21}$, $R_{22}$, $R_{23}$, $R_{24}$, $R_{25}$, $R_{26}$ and $R_{27}$ is independently selected from H, halogen, $NO_2$, $SO_3R$, $SO_2N(R)_2$, $C(O)OR$, $C(O)N(R)_2$, CN, CNS, OR, $OC(O)R$, SR, $CF_3$, NHC(O)R, $N(R)_2$ or $N[R]_3$ wherein each R is independently H, $(C_1-C_8)$alkyl, aryl (and heteroaryl), or a blocking group compatible with oligonucleotide synthesis.

In addition, at least one of $R_{21}$, $R_{22}$, $R_{23}$, $R_{24}$, $R_{25}$, $R_{26}$, and $R_{27}$ is -L-X, where L is a linker of 1 to 20 atoms, acyclic, cyclic or a combination thereof, containing C, N, O, S, Si and P; and X is a phosphoramidite or a reactive group (e.g., pentafluorophenyl ester); and any two adjacent groups ($R_{21}$ through $R_{26}$) can be combined to form a fused five or six-membered ring structure that is saturated or unsaturated, and can contain any of C, N, S and O as ring vertices. $R_{28}$ is a member selected from H and a substituted or unsubstituted $(C_1-C_8)$alkyl.

In the formula above, the bifunctional linking group K can be essentially any linking group that provides sufficient spacing for reaction of the phosphoramidite moiety to proceed when the composition is used to introduce FL into an oligonucleotide conjugate or composition. Typically, the linking group has from 3 to 50 main chain atoms selected from C, N, O, S, P and Si with remaining valences occupied by hydrogen atoms. A variety of heterobifunctional linking groups are commercially available and can be used in the present invention. Other suitable linking groups are described herein.

Coumarin Phosphoramidite Reagents

In one group of preferred embodiments, the invention provides coumarin phosphoramidite reagents (e.g., those compounds above in which FL is FL-1). One example of such a phosphoramidite reagent containing a preferred coumarin fluorophore and which is suitable for DNA synthesis, is shown in Reaction Scheme 8, as compound 34. In the phosphoramidite reagent 34, each of $R_{23}$ through $R_{26}$ is independently selected from the groups provided above; and j and k independently are 1 to 10. In a particularly preferred embodiment, reagent 34 includes a coumarin chromophore which emits light at about 458 nm. DNA probes containing this coumarin chromophore were prepared and gave the desired fluorescent emission properties.

REACTION SCHEME 8

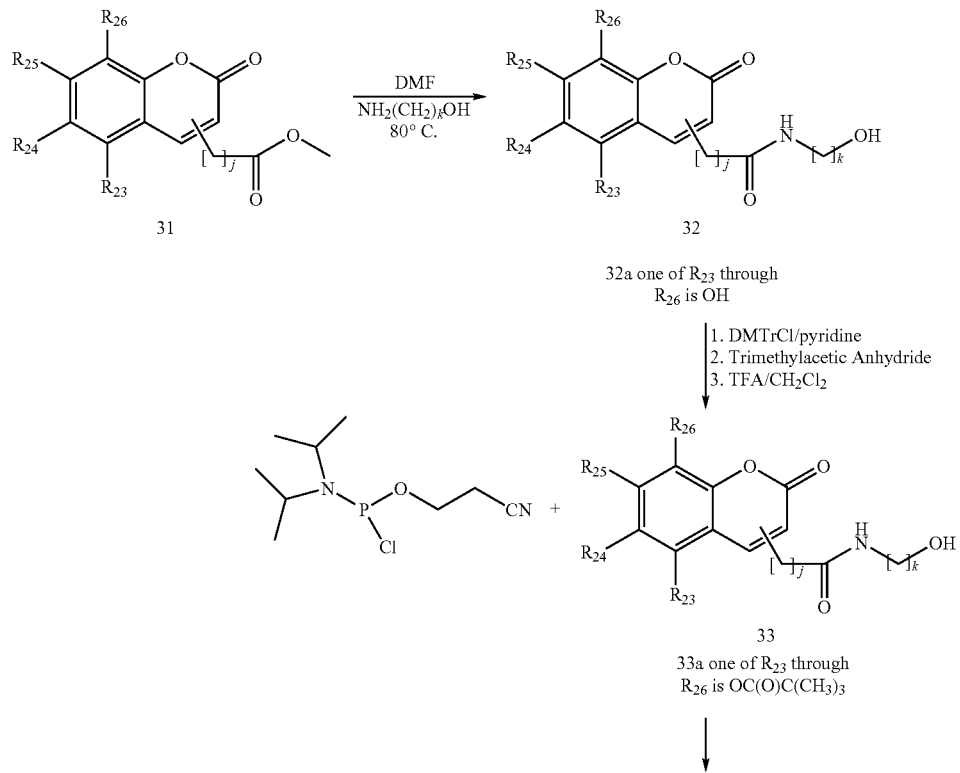

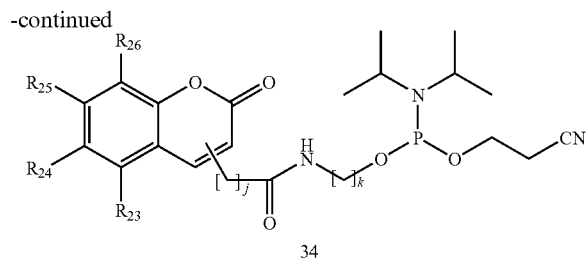

34

34a one of $R_{23}$ through $R_{26}$ is
$OC(O)C(CH_3)_3$

Referring now to Scheme 8 in general terms and also in an example that provides the specific phosphoramidite reagent 34a, a hydroxyl substituted (2-oxo-2H-chromen-4-yl)-alkyl-carboxyl methyl ester (31) is obtained according to the publication Baker et al. (J. Chem. Soc.; 170, 173 (1950)). Compound 31 is converted to the alkanol derivative 32 (specifically to 32a wherein one of $R_{23}$ through $R_{26}$ is —OH and the remaining R groups are H) by reaction with an aminoalkanol at 80° C. Reaction of 32 first with DMTrCl and then with trimethylacetic anhydride followed by the removal of the DMTr blocking group gives a pivaloate derivative 33, in the specific example 33a where one of $R_{23}$ through $R_{26}$ is —OC(=O)C(CH$_3$)$_3$ and the remaining R groups are H. Reaction of 33 with 2-cyanoethyl diisopropylchlorophosphoramidite gives reagent 34 (specifically 34a). The reagent 34 is used for incorporating the coumarin fluorophore into the 5'-terminus of DNA probes. It is noteworthy that removal of the protecting groups during automated oligonucleotides synthesis proceeds well, resulting in high yields. The symbols j and k in Scheme 8 are defined as 0 to 20 and 1 to 20, respectively.

Still other coumarins are known and can be modified to provide the phosphoramidite reagents above.

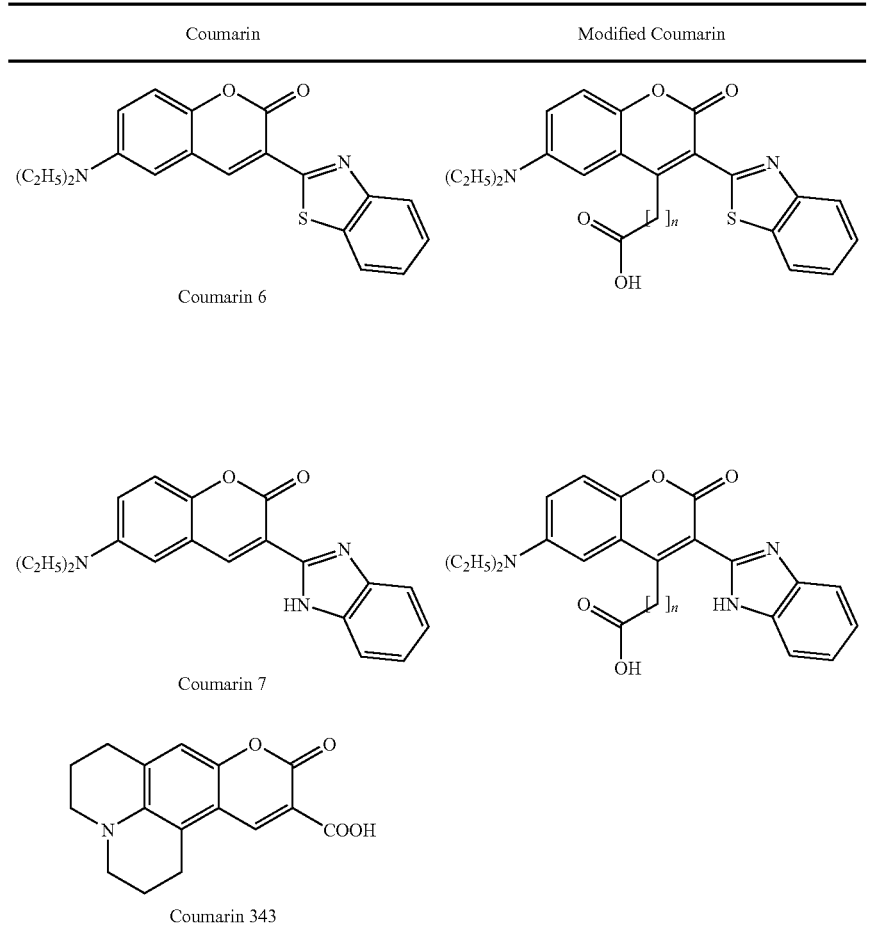

| Coumarin | Modified Coumarin |
|---|---|

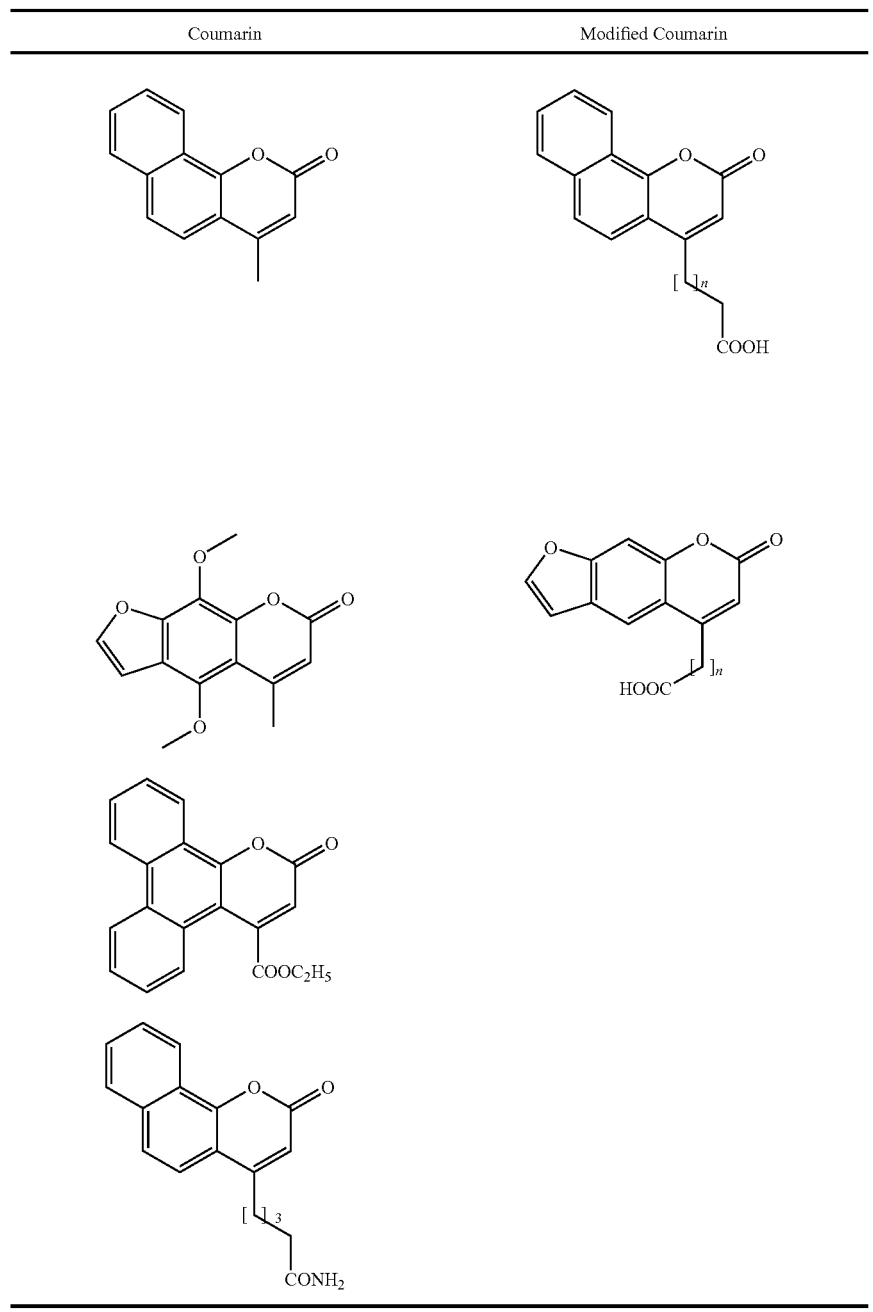

See, for example, *Bull. Chem. Soc. Japan.* 71(7):1719-1724 (1998); Kartha et aL, *Proc. Indian Acad. Sci. Sect. A,* 18:28 (1943); Atta et al., *Phosphorus, Sulfur, Silicon Relat. Elem.* 80:109-116 (1993); U.S. Pat. No. 5,696,157; Nicolaides et al., *J. Chem. Soc. Perkin Trans. I,* 2:283-290 (1992); and Saleh et al., *Phosphorus, Sulfur Silicon Relat. Elem.* 48:285-288 (1990).

Resorufin Phosphoramidite

Another new class of DNA synthesis reagents (see the fluorophore phosphoramidites in which FL is FL-2) are based on the 7-hydroxy-3H-phenoxazin-3-one chromophore present in the parent compound (resorufin) and have emission wavelength (595 nm) that is easily distinguished from FAM emission. In accordance with the invention the chromophore is synthesized in such a way as to incorporate a linker structure for further functionalization to the desired phosphoramidite reagents. The preparation of preferred examples of these reagents 37 suitable for DNA synthesis, is shown in Reaction Scheme 9. Generally, in reagents of formula 37, each of $R_{23}$, $R_{24}$, $R_{25}$, $R_{26}$ and $R_{27}$ is independently selected from H, halogen, $NO_2$, $SO_3R$, $SO_2N(R)_2$, C(O)OR, C(O)N(R)_2, CN, CNS, OR, OC(O)R, SR, $CF_3$, NHC(O)R, $N(R)_2$ or $N[R]_3$ wherein each R is independently H, ($C_1$-$C_8$)alkyl, aryl (and heteroaryl), or a blocking group compatible with oligonucleotide synthesis; and h=1 to 20. $R_{29}$ in the scheme is H or DMTr.

REACTION SCHEME 9

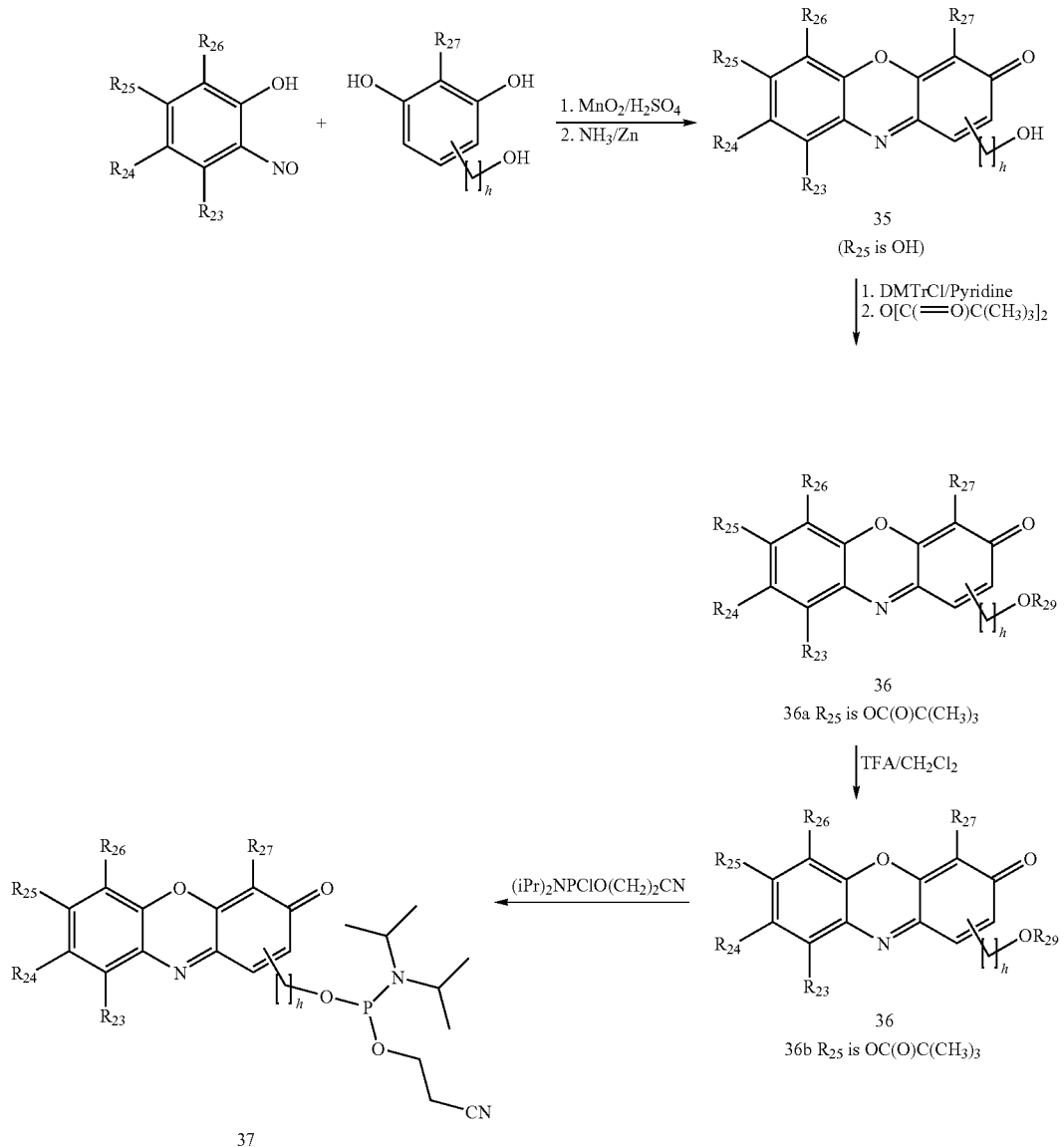

As is shown in the example of Scheme 9 in general terms and also for a specific example, reaction of nitrosorecorcinol derivative (commercially available or synthesized in accordance with the state-of-the-art) and of 4-(3-hydroxypropyl) benzene-1,3-diol (obtained in accordance with Forchiassin et al., *J. Heterocyc. Chem.* 20:493-494 (1983)) and $MnO_2$ yielded a resazurin derivative contaminated with some resorufin derivative. This mixture was treated with $NH_4OH$ and Zn dust to yield resorufin derivative 35 (specifically 35a where $R_{25}$ is OH and the remaining R groups are H) contaminated with 2,3,4-trihydro-2H-pyrano[3,2-b]phenoxazin-9-one as major impurity. The latter mixture was treated with DMTrCl and pyridine, and then with trimethylacetic acid anhydride. The product 36 was then subjected to purification by chromatography on silica gel to give the DMTr-protected derivative of 36a (where $R_{25}$ is —OC(=O)C(CH$_3$)$_3$, $R_{29}$ is DMTr, and the remaining R groups are H). The pure DMTr-derivative was treated with TFA/CH$_2$Cl$_2$ to yield a single product 36b after silica gel chromatography. Treatment of 36 (where $R_{25}$ is —OC(=O)C(CH$_3$)$_3$ and $R_{29}$ is H) with 2-cyanoethyl diisopropylchlorophosphoramidite gave the desired phosphoramidite reagent 37 (specifically 37a wherein $R_{25}$ is —OC(=O)C(CH$_3$)$_3$, and the remaining R groups are H) that can be utilized to introduce the fluorophore into a desired ODN.

Additional resorufin-type fluorophores that can be converted into suitable phosphoramidite reagents are shown in the table below.

TABLE 3

| Resorufin dye | Linker attachment sites |
|---|---|
| 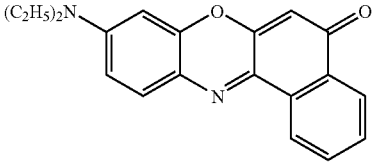 Nile Red | 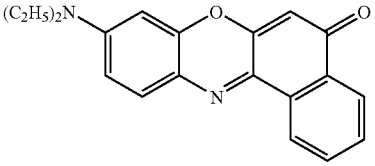 Attach linker to either of the phenyl rings or the alkyl groups |
| 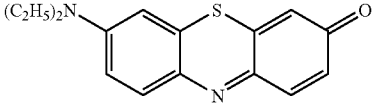 | 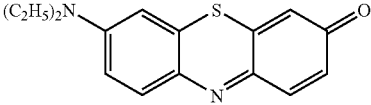 Attach linker to the phenyl ring, the quinone ring, the alkyl group or via a lactone (see lactone methods above) |
| 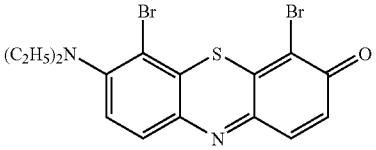 | |
| 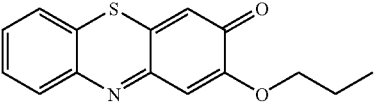 | Attach linker to the phenyl ring, the quinone ring or to the alkoxy substituent (UV absorption maximum 494 nm) |
| 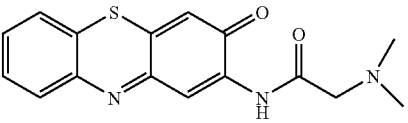 | Attach linker to the phenyl ring, the quinone ring or to the amide sidechain |
| 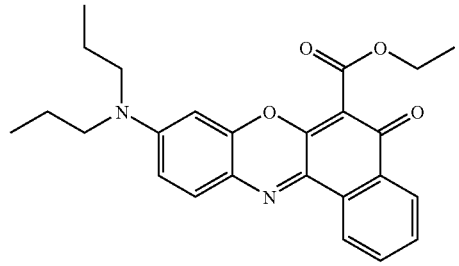 | Attach linker to either of the fused phenyl rings or to the amino or ester substituents (UV absorption maximum 569) |
| 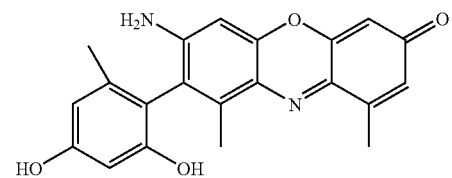 | Attach linker to any of the hydroxy, amino, or methyl groups or to other positions on the phenyl or quinone rings (UV absorption maximum 566) |

Additional compounds suitable for elaboration into the present resorufin-type phosphoramidite reagents are described in, for example, co-pending application Ser. No. 09/457,616; U.S. Pat. No. 4,954,630; Pashkevich et al., *Chem. Heterocycl. Cmpd., Engl. Transl.* 11:308-312 (1975); Morrison et al., *Photochem. Photobiol.,* 66:245-252 (1997); Afans'eva et al., *Chem. Heterocycl. Cmpd., Engl. Transl.* 174-177 (1983); Chem. Abstracts 16329 (1955); Long et al., *J. Heterocycl. Chem.* 36:895-900 (1999); and Musso et al., *Chem. Ber.,* 96:1936-1944 (1963).

In one group of embodiments, the present invention provides resorufin phosphoramidite reagents having the formula:

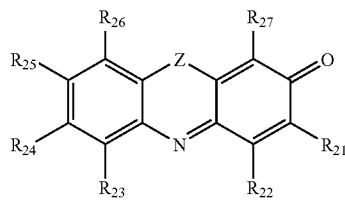

wherein Z is O or S and each of $R_{21}$, $R_{22}$, $R_{23}$, $R_{24}$, $R_{25}$, $R_{26}$ and $R_{27}$ is independently selected from H, halogen, $NO_2$, $SO_3R$, $SO_2N(R)_2$, C(O)OR, C(O)N(R)$_2$, CN, CNS, OR, OC(O)R, SR, $CF_3$, NHC(O)R, N(R)$_2$ or N[R]$_3$ wherein each R is independently H, ($C_1$-$C_8$)alkyl, at (and heteroaryl), or a blocking group compatible with oligonucleotide synthesis. In addition, at least one of $R_{21}$, $R_{22}$, $R_{23}$, $R_{24}$, $R_{25}$, $R_{26}$, and $A_{27}$ is -L-X, where L is a linker 1 to 20 atoms, acyclic, cyclic or a combination thereof, containing C, N, O, S, Si and P; and X is a phosphoramidite or a reactive group (e.g., pentafluorophenyl ester); and any two adjacent groups ($R_{21}$ through $R_{26}$) can be combined to form a fused ring structure that is saturated or unsaturated, and can contain any of C, N, S and O as ring vertices.

PPT Phosphoramidite

The synthesis of a phosphoramidite reagent incorporating a purple fluorescent dye PPT 44 having excitation and emission wavelengths of 384 and 400 nm, respectively is shown in Reaction Scheme 10 and in Example 10.

REACTION SCHEME 10

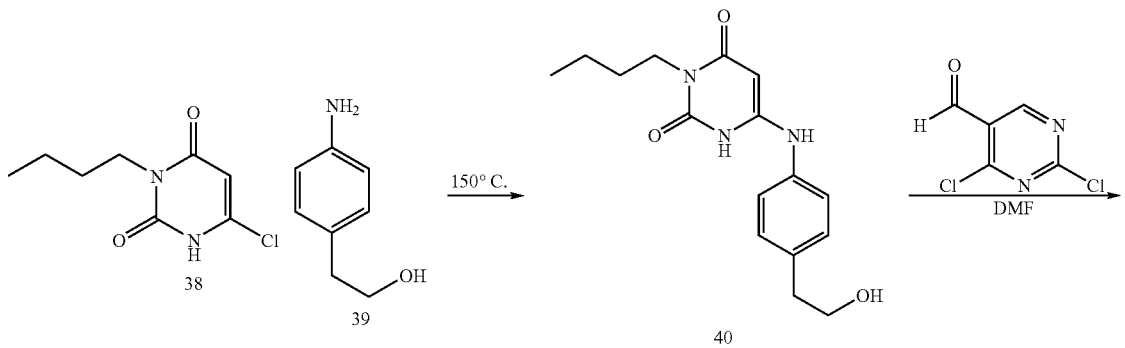

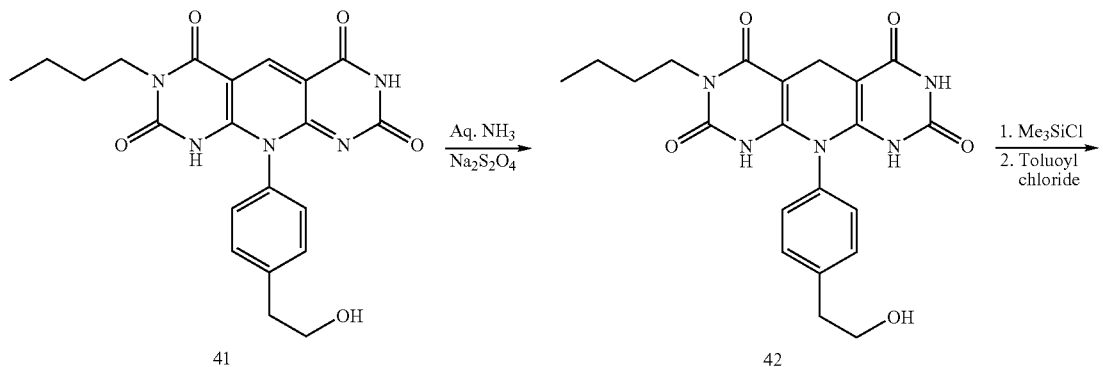

-continued

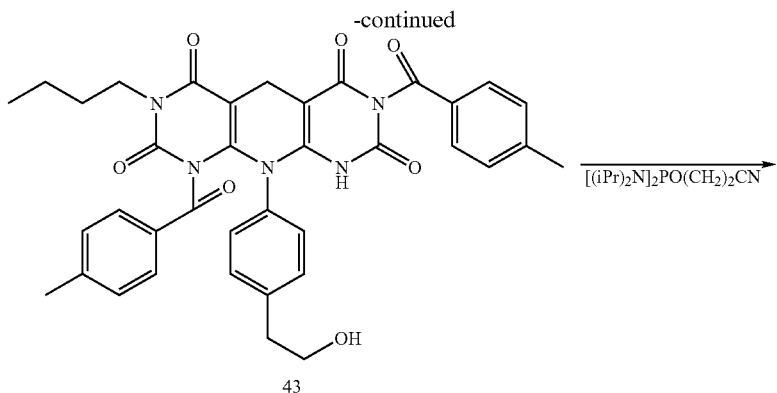

43

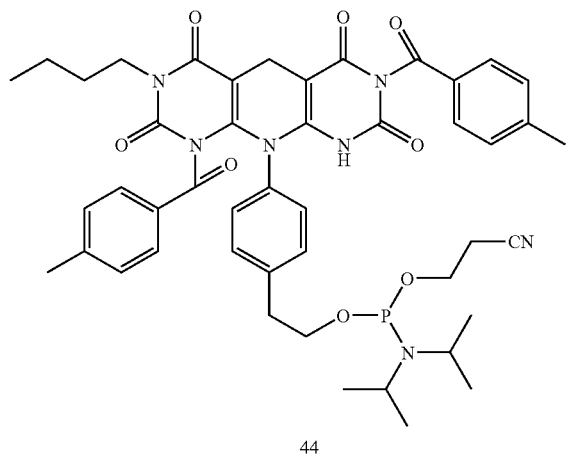

44

In accordance with this scheme 6-chloro-3-n-butyluracil 38 and 2-(4-aminophenyl)ethanol 39 are reacted to yield the phenyl substituted uracil derivative 40. The compounds 38 and 39 can be obtained in accordance with literature methods and general methods known to those of skill in the art. Reaction of 40 with 5-formyl-4,6-dichloro pyrimidine in DMF at room temperature affords the tricyclic heterocycle 41. Reduction of 41 in $NH_3/Na_2S_2O_4$ yields 42 which is then blocked as the toluoyl-derivative 43. In the final step 43 is reacted with 2-cyanoethyl diisopropylchlorophosphoramidite to yield the reagent PPT cyanoethyl phoporamidite 44 that can be used to introduce the PPT fluorophore into an ODN.

In related embodiments, the present invention provides PPT phosphoramidite reagents having the formula:

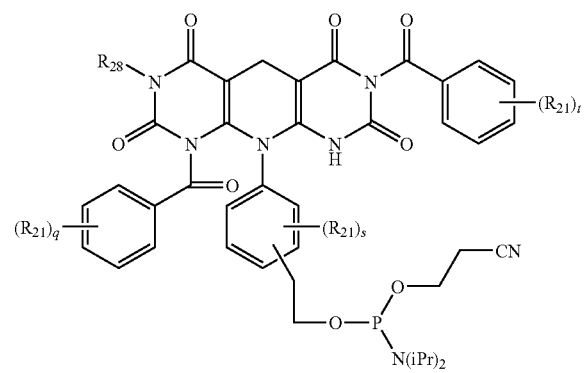

wherein each $R_{21}$ is independently selected from H, halogen, $NO_2$, $SO_3R$, $SO_2N(R)_2$, C(O)OR, C(O)N(R)_2, CN, CNS, OR, OC(O)R, SR, $CF_3$, NHC(O)R, $N(R)_2$ or $N[R]_3$ wherein each R is independently H, $(C_1-C_8)$alkyl, aryl (and heteroaryl), or a blocking group compatible with oligonucleotide synthesis; and any two adjacent $R_{21}$ groups can be combined to form a fused five or six-membered ring structure that is saturated or unsaturated, and can contain any of C, N, S and O as ring vertices. $R_{28}$ is a member selected from H and a substituted or unsubstituted $(C_1-C_8)$alkyl.

A number of the above coumarin, resorufin and PPT fluorophores are availed with an alkylcarboxyl group substituent which serves as a starting material for the synthesis of the corresponding phosphoramidite reagents. Accordingly, these compounds can be activated on the alkylcarboxyl group as the pentafluorophenyl esters. The activated esters are used to attach these dyes to amine modified oligonucleotides.

Similarly, in still other embodiments, dUTP-labeled quenchers or fluorophores are obtained for example in accordance with the teachings of U.S. Pat. No. 5,328,824. Furthermore, the phosphoramidite of 7-labeled pyrazolo[3,4-d]pyrimide-labeled quenchers or fluorophores are synthesized according to the teaching of U.S. Pat. No. 5,824,796, and can be used for labeling of oligonucleotides.

PPG Red Dye-based and other Phosphoramidite Reagents for Oligonucleotide Synthesis.

In another embodiment the red dye 13 quencher is attached to the 3-position of pyrazolo[5,4-d]pyrimidines (PP) or the 5-position of a pyrimidine. Referring now to Scheme 11 itself, the starting material is 5-(4-amino-3-iodopyrazolo[5,4-d]-pyrimidinyl)-2-(hydroxymethyl)oxolan-3-ol 45 which is available in accordance with Seela et al. *J. Chem. Soc., Perkin. Trans.*, 1 (1999, 479-488). Compound 45 is first reacted with N-propynyl-2,2,2-trifluoroacetate (or a homolog thereof where in the scheme n is 1 to 10) and then with Pd(PPh$_3$)$_4$-CuI to give the alkyne derivative 46. Pd/H$_2$ reduction of 46 followed by ammonium hydroxide treatment gives the aminoalkyl derivative 47 (PPA'). Reaction of PPA' with compound 2 (available as disclosed in connection with Reaction Scheme 1) yielded substituted PPA'-Red 13, 48. Reaction of 48 with (1,1-dimethoxyethyl)dimethyl-amine blocks the amino group of the pyrazolo[5,4-d]pyrimidine to yield 49. Compound 49 is first reacted with DMTrCl and then with 2-cyanoethyl diisopropylchlorophosphoramidite to give the DMTrCl blocked PPA'-Red 13 phosphoramidite 50.

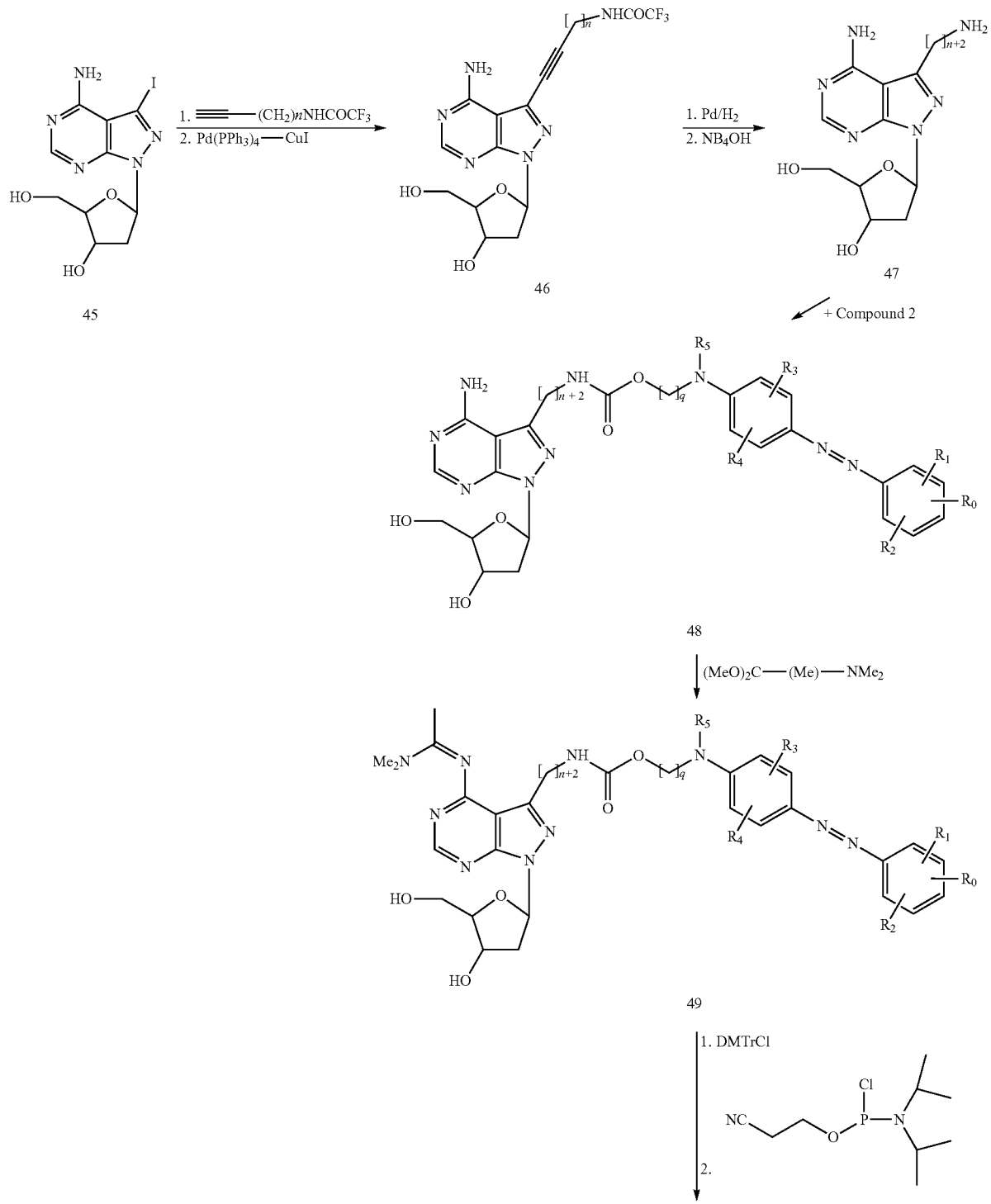

REACTION SCHEME 11

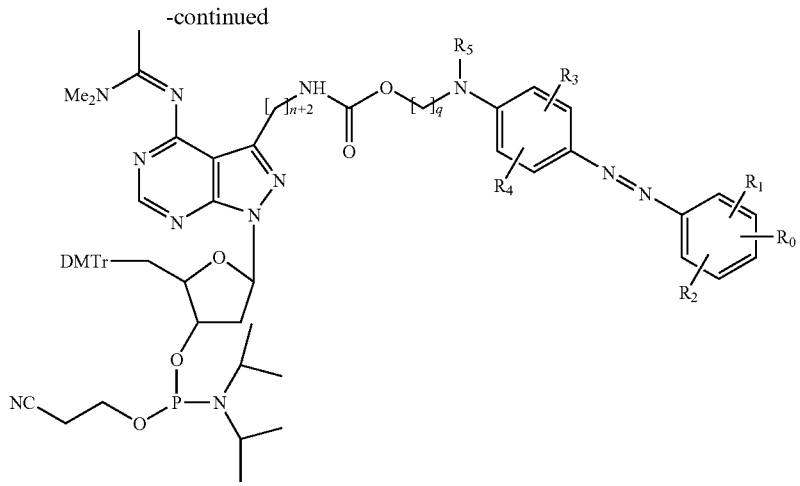

50

In still other embodiments starting with the deoxyriboside of 6-amino-5-hydroxy-3-iodo-pyrazolo[5,4-d]pyrimidin-4-one (3-Iodo-PPG) the phosphoramidite reagent containing the Red 13 dye covalently linked to the 3-Iodo-PPG moiety is synthesized with reactions analogous to those shown in Reaction Scheme 11. Similarly starting with 5-aminopropyldeoxyuridine the phosphoramidite reagent containing the Red 13 dye covalently linked to 5-aminopropyl-deoxyuridine is synthesized.

It will be clear to those skilled in the art in light of the foregoing disclosure that the pyrazolopyrimidine-Red-13- or uridine-Red 13-based phosphoramidites within the scope of this invention can contain various linkers between the pyrazolopyrimidine and uracil bases and the Red 13 quenchers, to the full extent such linkers are available in accordance with the state of the art and this disclosure.

FL-ODN-Q and FL-ODN-Q-MGB Probes

Using the reagents and methods outlined above, as well as other readily available starting materials, probes that are useful in, for example, hybridization assays can be prepared.

Accordingly, the present invention provides oligonucleotide probes having the formula:

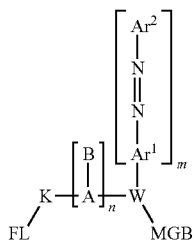

wherein FL is a fluorophore with emission wavelengths in the range of about 300 to about 800 nm and more preferably 400 to 700 nm (specific examples of fluorophores having emissions in this range are described in Haugland, HANDBOOK OF FLUORESCENT PROBES AND RESEARCH CHEMICALS, SIXTH ED., Eugene, Oreg.); K is a linker containing between 1 and 30 main chain atoms which include any of C, O, N, S, and P; [A-B]$_n$ represents a nucleic acid oligomer (e.g. DNA, RNA or PNA or any combination thereof, including forms with modified bases and sugars), where A includes the sugar phosphate backbone (including modified sugars or peptides and modified phosphates), each B is a nucleic acid base (including modified bases and analogs, e.g., pyrazolo[3,4-d]pyrimidine bases), and the subscript n is the number of nucleotide units, typically from about 3 to about 100, preferably from about 6 to 50, and more preferably about 8 to 25. More particularly, the letter B represents in each instance, any of the purine- and pyrimidine-; pyrazolo[3,4-d]pyrimidine-, 7-substituted pyrazolo[3,4-d]pyrimidine-, 7-deazapurines, 7-substiuted 7-deazapurines, modified purine- and pyrimidine-bases, and the oligonucleotide or nucleic acid can include any combinations of these bases.

The letter W represents a linker having 3 to approximately 100 main chain atoms, selected from the group consisting of C, O, N, S, Si and P. In one group of embodiments, W is a substituted branched aliphatic chain, or a substituted ring structure or a combined substituted aliphatic and ring structure. The symbols Ar$^1$ and Ar$^2$ represent substituted or unsubstituted aryl groups as described in more detail above, while the subscript m is 0 or 1. In certain preferred embodiments, Ar$^2$ is substituted with one or more electron-withdrawing groups (e.g., nitro, cyano, carboxy, sulfonyl, halogen and the like) and Ar$^1$ is substituted with one or more electron-donating groups (e.g., alkyl, alkoxy, amino, alkylamino, dialkylamino and the like). Finally, the symbol MGB represents a minor groove binder. A variety of minor groove binders can be used to prepare the probes described herein. Preferred minor groove binders are those that bind in a non-covalent manner, but have the crescent shape that is useful for binding in the minor groove. Suitable examples include, analogs of CC1065, Hoeschst 33258, DAPI, lexitropsins, distamycin, netropsin, berenil (and related diarylamidines), duocarmycin, pentamidine, 4,6-diamino-2-phenylindole, and pyrrolo[2,1-c][1,4]benzodiazepines.

In one group of preferred embodiments, the probes have the formula:

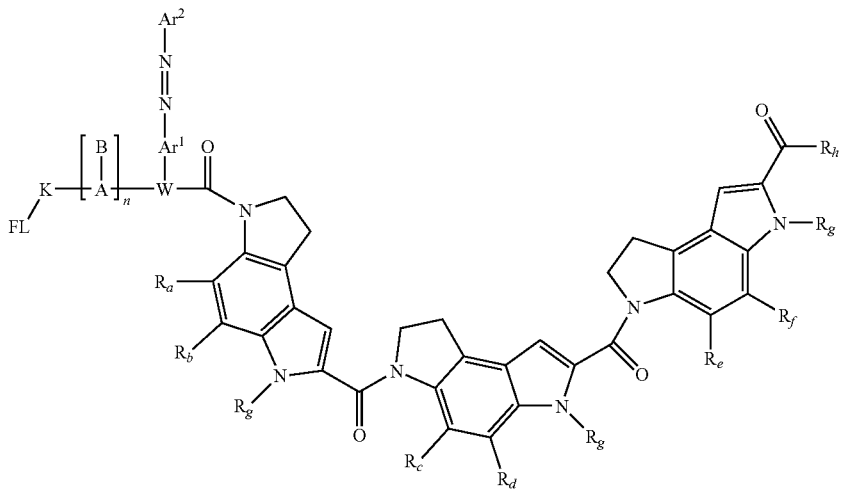

wherein the symbols FL, K, A, B, n, W, Ar¹, and Ar² have the meanings provided above, and the symbols $R_a$, $R_b$, $R_c$, $R_d$, $R_e$ and $R_f$ represent substituents selected from H, halogen, $(C_1-C_8)$alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)_mCO_2^-$, $(CH_2)_mOPO_3^{-2}$, and $NHC(O)(CH_2)_mCO_2^-$, and esters and salts thereof, wherein each $R_g$ is independently H or $(C_1-C_8)$alkyl, and the subscript m is an integer of from 0 to 6. The symbol $R_h$ represents H or a group (typically the vestige of a linking group used in solid phase synthesis) having from 1-30 atoms selected from C, N, O, P, and S which is either cyclic, acyclic, or a combination thereof, and having additional hydrogen atoms to fill the available valences.

In a related group of embodiments, the quencher Ar¹—N=N—Ar² is attached to $R_h$ rather than W.

In another preferred group of embodiments, the probes of the present invention are represented by Formula 6:

Formula 6

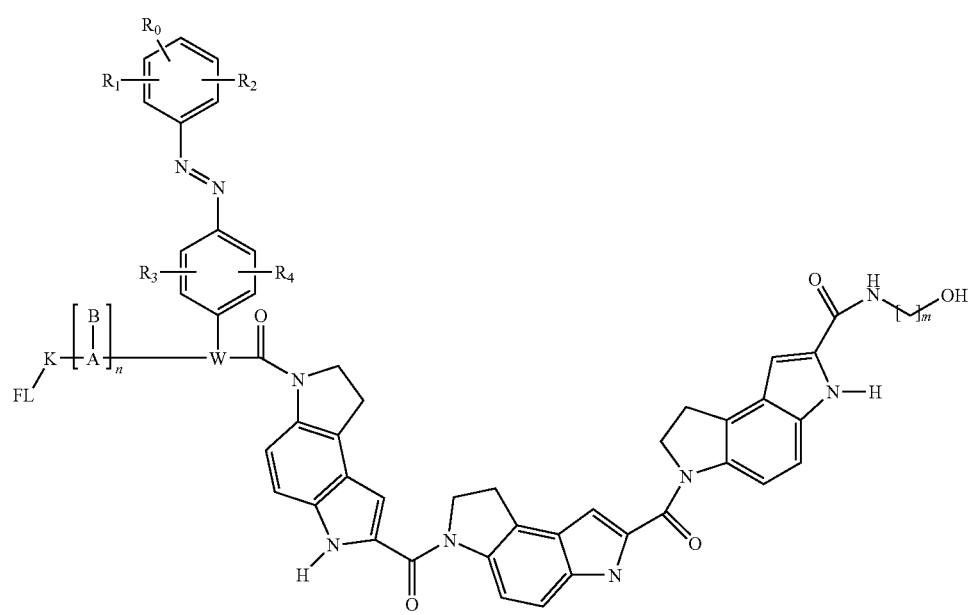

wherein the symbols FL, K, A, B, W $R_0$, $R_1$, $R_2$, $R_3$ and $R_4$ having the meanings provided above.

In a particularly preferred embodiment, the probe has the formula shown in Formula 6 wherein W is —$(CH_2)_3N(-)$-$(CH_2)_3$—; $R_0$=$NO_2$; $R_1$=—Cl; $R_2$=$R_3$=$R_4$=H; K is a ($C_1$-$C_6$)alkylene linker and m=3. The W-(Q)-MGB portion of the molecule is typically attached at the 3'-end of the oligonucleotide, but can also be attached at the 5'-end by performing the synthesis with a 5'-phosphoramidite in place of the more commonly used 3'-phosphoramidite reagents.

Syntheses of PNA and PNA/DNA chimeras are known in the art and can generally be performed in accordance with the publications Uhlmann et al., *Angew. Chem. Inter. Ed.,* 37:2796-2823 (1998); Mayfield et al., *Anal. Biochem.,* 401-404 (1998). Synthesis of oligonucleotides containing one or more locked nucleic acid bases can be performed as described in Kyaemo et al., *J. Org. Chem.* 65.5167-5176 (2000).

Conjugate probes of the present invention containing a fluorescent reporter-quencher pair can be used in conjunction with the amplification of target polynucleotides, frequently in methods utilizing PCR, as described for example by Holland et al., *Proc. Natl. Acad. Sci.* 86:7276-7280(1991) and Wittwer et al., *Biotechniques* 22:176-181 (1997). The binding site of the conjugate probe is generally located between the PCR primers used to amplify the target polynucleotide.

Use of the conjugate oligonucleotide probes according to the present invention for detection of target oligonucleotide sequences provides several advantages over prior-art reporter quencher groups and combinations. For example, the probes including the 4-[4-nitrophenyl)diazinyl]phenylamine quencher structure in accordance with the present invention gave larger signal to noise ratios (S/N) in probes with either FAM or TAMRA serving as reporters than those probes using dabcyl as a quencher. Furthermore, the quenchers used in accordance with the invention show a broader absorbance range than dabcyl, allowing efficient quenching of a broad range of fluorophores. In addition, the MGB-oligonucleotide conjugate probes have improved hybridization characteristics and an improved quencher provides about 30-fold increase in S/N ratio with TAMRA compared to a standard probe (no $DPI_3$) with dabcyl. Moreover, the attachment of a minor groove binder to oligonucleotides containing a quencher/fluorophore pair allows the quencher to quench the fluorophores' fluorescence outside of its typical absorbance range. Finally, certain reagents are now available (as provided herein) that can be used to introduce the quencher into the probe composition during automated oligonucleotide synthesis, while other reagents (e.g., dabcyl phosphoramidite) are commercially available (Glen Research, Sterling, Va.).

In the present invention, an oligonucleotide comprises a plurality of nucleotide units, a 3' end and a 5'end. The oligonucleotide may contain one or more modified bases other than the normal purine and pyrimidine bases, as well as modified internucleotide linkages capable of specifically binding target polynucleotide through Watson-Crick base pairing, or the like. In addition, oligonucleotides may include peptide oligonucleotides (PNAs) or PNA/DNA chimeras, the synthesis of which is known and can be performed for example in accordance with the publications Uhlmann et al., *Angew. Chem. Inter. Ed.,* 37:2796-2823 (1998) and Mayfield et al., *Anal. Biochem.,* 401-404 (1998).

Figure 5:
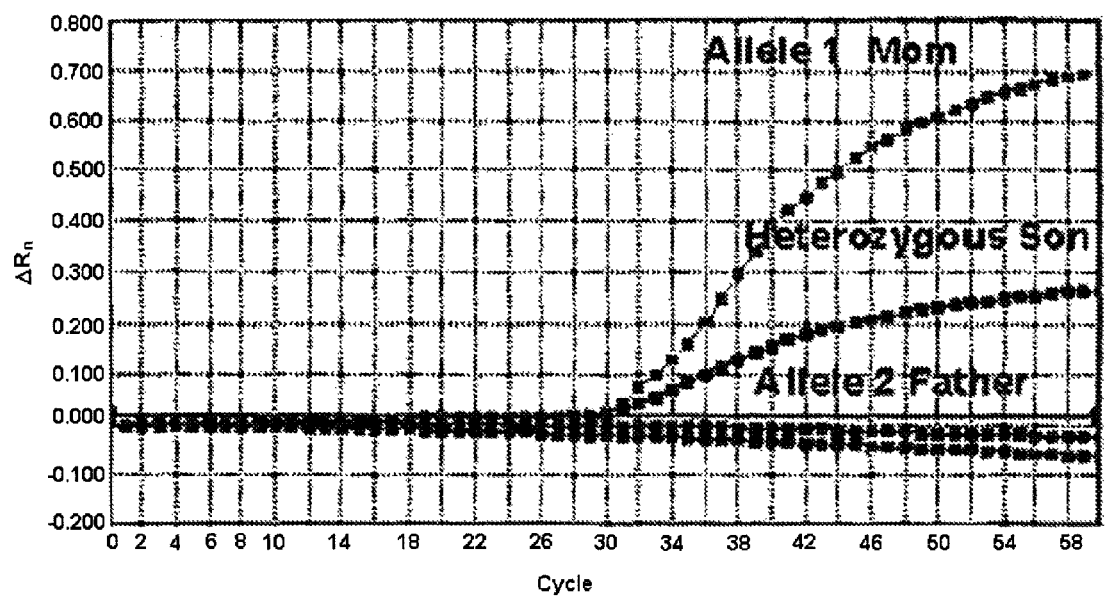
FIG. 5 illustrates the real-time detection of RRM1 allele 1 (TIC mismatch) with a non-cleavable MGB-probe, MGB-Q-ATA TCT AGC GTT GA-FI (30, below, wherein the subscripts t, v, and m are 3, $R_0$ is 4-$NO_2$, $R_1$ is 2-Cl, $R_2$, $R_3$ and $R_4$ are H and Fl is fluorescein).

In one group of embodiments, the oligonucleotide probes of the invention will have a sufficient number of phophodiester linkages adjacent to the 5' end to allow 5'-3' exonuclease activity to allow efficient cleavage between the quencher and fluorophore components in the probe. A suitable number of phosphodiester linkages in this regard is approximately between 1 and 100, but preferably between 3 and 40. In other embodiments, conjugates containing fluorophore and quencher pairs will provide adequate signal upon hybridization to the target nucleic acid, with cleavage of the probe. Amplified material can be detected with 5'-MGB-Q-ODN-Fl conjugates (see Example 16 and FIG. 5) in which the target is amplified via PCR and the detection is performed in real-time without cleavage of the conjugate. The example below further illustrates the ability of the 5'-MGB to prevent the 5'-nuclease activity of the polymerase to cleave this probe and further, that the MGB in combination with the quencher effectively quench a fluorophore having an emission maximum of 520 nm when the probe is not hybridized to its complementary target. This method can also be used as an endpoint assay rather than a real-time procedure.

Assays and Hybridization Methods

The compositions of the present invention can be used with a variety of techniques, both currently in use and to be developed, in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; techniques in which hybridization of an oligonucleotide to a target nucleic acid is followed by hydrolysis of the oligonucleotide to release an attached label; and techniques in which two or more oligonucleotides are hybridized to a target nucleic acid and interactions between the multiple oligonucleotides are measured. The conditions for hybridization of oligonucleotides, and the factors which influence the degree and specificity of hybridization, such as temperature, ionic strength and solvent composition, are well-known to those of skill in the art. See, for example, Sambrook et al., supra; Ausubel et al., supra; Innis et al. (eds.) PCR Protocols, Academic Press, San Diego, 1990; Hames et al. (eds.) NUCLEIC ACID HYBRIDISATION: A PRACTICAL APPROACH, IRL Press, Oxford, 1985; and van Ness et al. (1991) *Nucleic Acids Res.* 19:5143-5151.

Additionally, the compounds described herein can be used to detect polymeric targets such a nucleic acids using techniques utilized for, e.g., gene expression, SNP detection, sequencing methods, FRET detection (TaqMan assays, molecular beacons, linear beacons), array-based methods, primer extension, enzymatic methods, and the like.

Hybridization Probes

In one application of the present invention, one or more FL-oligonucleotide conjugates are used as probe(s) to identify a target nucleic acid by assaying hybridization between the probe(s) and the target nucleic acid. A probe may be labeled with any detectable label of the present invention, or it may have the capacity to become labeled either before or after hybridization, such as by containing a reactive group capable of association with a label or by being capable of hybridizing to a secondary labeled probe, either before or after hybridization to the target. As a basis of this technique it is noted that conditions for hybridization of nucleic acid probes are well-known to those of skill in the art. See, for example, Sambrook et al., MOLECULAR CLONING: A LABORATORY MANUAL, SECOND EDITION, Cold Spring Harbor Laboratory Press (1989), Ausubel et al., CURRENT PROTOCOLS IN MOLECULAR BIOLOGY, John Wiley & Sons (1987, 1988, 1989, 1990, 1991, 1992, 1993, 1994, 1995, 1996); Hames et al. (eds.) NUCLEIC ACID HYBRIDIZATION: A PRACTICAL APPROACH, IRL Press, Oxford, 1985; and van Ness et al. *Nucleic Acids Res.* 19:5143-5151(1991).

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; and other known techniques. See, for example, Falkow et al., U.S. Pat. No. 4,358,535; Urdea et al., U.S. Pat. Nos. 4,868,105 and 5,124,246; Freifelder, PHYSICAL BIOCHEMISTRY, SECOND EDITION, Freeman & Co., San Francisco, 1982; Sambrook et al., supra; Ausubel et al., supra; and Hames et al., supra.

Assays Utilizing Labeled Probes, Hydrolyzable Probe and Labeled Primers

Additional applications for oligonucleotide conjugates containing a fluorophore and quencher are found in assays in which a labeled probe is hybridized to a target and/or an extension product of a target, and a change in the physical state of the label is effected as a consequence of hybridization. A probe is a nucleic acid molecule that is capable of hybridizing to a target sequence in a second nucleic acid molecule. By way of example, one assay of this type, the hydrolyzable probe assay, takes advantage of the fact that many polymerizing enzymes, such as DNA polymerases, possess intrinsic 5'-3' exonucleolytic activities. Accordingly, if a probe is hybridized to a sequence that can serve as a template for polymerization (for instance, if a probe is hybridized to a region of DNA located between two amplification primers, during the course of an amplification reaction), a polymerizing enzyme that has initiated polymerization at an upstream amplification primer is capable of exonucleolytically digesting the probe. Any label attached to such a probe will be released, if the probe is hybridized to its target and if amplification is occurring across the region to which the probe is hybridized. Released label is separated from labeled probe and detected by methods well-known to those of skill in the art, depending on the nature of the label. For example, radioactively labeled fragments can be separated by thin-layer chromatography and detected by autoradiography; while fluorescently-labeled fragments can be detected by irradiation at the appropriate excitation wavelengths with observation at the appropriate emission wavelengths. This basic technique is described for example in U.S. Pat. No. 5,210,015.

In a variation of this technique, a probe contains both a fluorescent label and a quenching agent, which quenches the fluorescence emission of the fluorescent label. In this case, the fluorescent label is not detectable until its spatial relationship to the quenching agent has been altered, for example by exonucleolytic release of the fluorescent label from the probe. Thus, prior to hybridization to its target sequence, the dual fluorophore/quencher labeled probe does not emit fluorescence. Subsequent to hybridization of the fluorophore/quencher-labeled probe to its target, it becomes a substrate for the exonucleolytic activity of a polymerizing enzyme which has initiated polymerization at an upstream primer. Exonucleolytic degradation of the probe releases the fluorescent label from the probe, and hence from the vicinity of the quenching agent, allowing detection of a fluorescent signal upon irradiation at the appropriate excitation wavelengths. This method has the advantage that released label does not have to be separated from intact probe. Multiplex approaches utilize multiple probes, each of which is complementary to a different target sequence and carries a distinguishable label, allowing the assay of several target sequences simultaneously.

The use of FL-ODN-Q-DPI$_3$ conjugates in this and related methods allows greater speed, sensitivity and discriminatory power to be applied to these assays. In particular, the enhanced ability of MGB-oligonucleotide conjugates to allow discrimination between a perfect hybrid and a hybrid containing a single-base mismatch facilitates the use of hydrolyzable probe assays in the identification of single-nucleotide polymorphisms and the like, as described in the publication WO 995162A2. Examples 15 and 16 illustrate the utility of FL-ODN-Q- DPI$_3$ conjugates in this type of assay. Compositions and methods of the invention are capable of discriminating single-nucleotide mismatches and are also capable of discriminating between sequences that have multiple mismatches with respect to one another.

Another application embodiment uses a self-probing primer with an integral tail, where the quencher/fluorophore is present in the hairpin, that can probe the extension product of the primer and after amplification hybridizes to the amplicon in a form that fluoresces. The probing of a target sequence can thereby be converted into a unimolecular event (Whitcombe et al., *Nat. Biotech.* 17:804-807 (1999)).

Fluorescence Energy Transfer

In other applications, compositions of the invention, e.g., oligonucleotide conjugates containing a fluorophore/quencher pair (FL-ODN-Q or FL-ODN-Q-MGB) are used in various techniques which involve multiple fluorescent-labeled probes. In some of these assays changes in properties of a fluorescent label are used to monitor hybridization, For example, fluorescence resonance energy transfer (FRET) has been used as an indicator of oligonucleotide hybridization. In one embodiment of this technique, two probes are used, each containing a fluorescent label and a quencher molecule respectively. The fluorescent label is a donor, and the quencher is an acceptor, wherein the emission wavelengths of the donor overlap the absorption wavelengths of the acceptor. The sequences of the probes are selected so that they hybridize to adjacent regions of a target nucleic acid, thereby bringing the fluorescence donor and the acceptor into close proximity, if target is present. In the presence of target nucleic acid, irradiation at wavelengths corresponding to the absorption wavelengths of the fluorescence donor will result in emission from the fluorescence acceptor. These types of assays have the advantage that they are homogeneous assays, providing a positive signal without the necessity of removing unreacted probe. For further details and additional examples of the assays which are known in the art, see, for example, European Patent Publication 070685; Agrawal & Zamecnik, *Nucl. Acids Res.* 18:5419-5423 (1990); and Cardullo et al., (1988) *Proc. Natl. Acad. Sci. USA* 85:8790-8794. Additional applications of the novel compositions of the present invention are in those and related techniques in which interactions between two different oligonucleotides that are both hybridized to the same target nucleic acid are measured. The selection of appropriate fluorescence donor/fluorescence acceptor pairs will be apparent to one of skill in the art, based on the principle that, for a given pair, the emission wavelengths of the fluorescence donor will overlap the absorption wavelengths of the acceptor. The enhanced ability of $DPI_3$-oligonucleotide conjugates to distinguish perfect hybrids from hybrids containing a single base mismatch facilitates the use of FRET-based techniques in the identification of single-nucleotide polymorphisms and the like.

In another application of the novel compositions of the invention, the fluorescence of the FL-ODN-Q conjugate is quenched in its native state. But, after hybridization with the intended target the spatial arrangement of the fluorophore and quencher moieties are changed such that fluorescence occurs. For this basic technique see for example Tyagi et al., *Nat. Biotech.* 16:49-53 (1998); and U.S. Pat. No. 5,876,930.

It should be understood that in addition to the fluorophores which are found in accordance with the present invention especially useful to be used with the quenchers of the invention, and which fluorophores are incorporated into ODNs in accordance with the invention, a person of ordinary skill may choose additional fluorophores to be used in combination with the quenchers of the present invention, based on the optical properties described in the literature, such as the references: Haugland HANDBOOK OF FLUORESCENT PROBES AND RESEARCH CHEMICALS, Six Edition, Eugene, Oreg., pp. 235-236. 1996; Berlman, Handbook of Fluorescence Spectra of Aromatic Molecules, $2^{nd}$, Academic Press, New York, 1971; Du et al., PhotochemCAD. A Computer-Aided Design and Research Tool in Photochemistry, *Photochem. Photobiol.* 68:141-142 (1998). Therefore the use of the novel ODN quencher conjugates in combination with these known fluorophores is considered within the scope of the invention.

In another application, the minor groove binder, $DPI_3$, is coupled to a quencher in a FL-ODN-Q-$CDPI_3$ conjugate to improve signal to noise ratios (see Table 4, below). Preferred quenchers are the quenchers of Formula 6 and more preferably, the quenchers are those provided in the conjugates of formulae 8-11, 12-16 (in Table 4) and further depicted as conjugate 30 (in Reaction Scheme 7).

Additional quenchers suitable for use in combination with the novel fluorophores (34, 37 and 44) of the invention include dabcylnitrothiazole, TAMRA, 6-(N-[7-nitrobenz-2-oxa-1,3-diazol-4-yl]amino) hexanoic acid, 6-carboxy-X-rhodamine (Rox) and QSY-7.

Another application of the novel fluorophore/quencher pairs of the invention is to incorporate the pair into enzyme substrates, where fluorescence is quenched because of the proximity of the fluorophore and quencher. However, after an enzyme cleaves the substrate the fluorophore and quencher become separated and fluorescence is observed. An example of this technique is described below using the phosphodiesterase enzyme. It will be clear to those schooled in the art that suitable substrates containing both the novel quenchers and fluorophores can be constructed for enzymes that cleave substrates.

Oligonucleotide Arrays

In another application, the oligonucleotide conjugates of the present invention are utilized in procedures employing arrays of oligonucleotides or oligonucleotide conjugates. Techniques for sequencing by hybridization, single nucleotide polymorphism analysis (SNPs) and array-based analysis of gene expression (see, Hacia et al., *Nat. Genet.* 22:119-120 (1999)) are well-known and can be readily adapted to utilize the conjugates of the present invention. For example, an ordered array of oligonucleotides of different known sequences (or their conjugates) is used as a platform for hybridization to one or more test polynucleotides, nucleic acids or nucleic acid populations. Determination of the oligonucleotides which are hybridized and alignment of their known sequences allows reconstruction of the sequence of the test polynucleotide. For a description of these techniques see for example, U.S. Pat. Nos. 5,492,806; 5,525,464; 5,556,752; and PCT Publications WO 92/10588 and WO 96/17957. Materials for construction of arrays include, but are not limited to, nitrocellulose, glass, silicon wafers and optical fibers.

Structural Considerations

The terms oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids which are disclosed by Nielsen et al., *Science* 254:1497-1500 (1991); bicyclo DNA oligomers (Bolli et al., *Nucleic Acids Res.* 24:4660-4667 (1996)) and related structures. One or more MGB moieties and/or one or more fluorescent labels, and quenching agents can be attached at the 5' end, the 3' end or in an internal portion of the oligomer. A preferred MGB in accordance with the invention is $DPI_3$ and the preferred quencher is red 13 amide.

Preferred in the present invention are DNA oligonucleotides that are single-stranded and have a length of 100 nucleotides or less, more preferably 50 nucleotides or less, still more preferably 30 nucleotides or less and most preferably 20 nucleotides or less with a lower limit being approximately 5 nucleotides.

Oligonucleotide conjugates containing a fluorophore/quencher pair with or without an MGB may also comprise one or more modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. The modified nucleotides which may be included in the ODN conjugates of the invention include 7-deazapurines and their derivatives and pyrazolopyrimidines (described in PCT WO 90/14353); and in co-owned and co-pending application Ser. No. 09/054,630.

Preferred base analogues of this type include the guanine analogue 6-amino-1H-pyrazolo[3,4-d]pyrimidin-4(5H)-one (ppG or PPG) and the adenine analogue 4-amino-1H-pyrazolo[3,4-d]pyrimidine (ppA or PPA). Also of use is the xanthine analogue 1H-pyrazolo[5,4-d]pyrimidin-4(5H)-6(7H)-dione (ppX). These base analogues, when present in an oligonucleotide, strengthen hybridization and improve mismatch discrimination. All tautomeric forms of naturally-occurring bases, modified bases and base analogues may be included in the oligonucleotide conjugates of the invention.

Similarly, modified sugars or sugar analogues can be present in one or more of the nucleotide subunits of an oligonucleotide conjugate in accordance with the invention. Sugar modifications include, but are not limited to, attachment of substituents to the 2', 3' and/or 4' carbon atom of the sugar, different epimeric forms of the sugar, differences in the α- or β-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, and cyclopentyl.

Modified internucleotide linkages can also be present in oligonucleotide conjugates of the invention. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Several further modifications of bases, sugars and/or internucleotide linkages, that are compatible with their use in oligonucleotides serving as probes and/or primers, will be apparent to those of skill in the art.

Certain preferred embodiments of the invention involve the synthesis of numerous phophoramidites with various quencher chromophores, based on the structures of known dyes and their analogues (see, the Color Index, Issue 3 on CDD-ROM, pages 4009-4324; Society of Dyers and Colourists, Bradford, England; http://www.sdc.org.uk) and linkers and their incorporation at the 3'-end of fluorogenic MGB ODNs as shown in Reaction Scheme 3. Different fluorescent reporter groups (shown in Reaction Scheme 7) were also incorporated into the oligonucleotide probes and are described in the EXPERIMENTAL section. The fluorogenic properties of these ODN conjugates are described in Table 4.

In other embodiments MGB molecules, due to their desirable improved hybridization properties, were incorporated into oligonucleotides containing both a fluorophore and a quencher, without loss in hybridization specificity, fluorescent quenching and fluorescent signal. The flat aromatic quencher residue coupled to the neighboring aromatic $DPI_3$ residue, have strict geometric requirements since the linker between the oligonucleotide and the $DPI_3$ residue must be flexible enough to allow positioning of the $DPI_3$ in the minor groove after DNA duplex formation.

Characteristics of Reagents of the Invention

A number of $FL-ODN-Q-DPI_3$ conjugates synthesized with the reagents and methods of the invention are shown in Formulas 7 to 16, where n specifies the number of bases in the oligonucleotide and FL is either FAM or TAMRA. "B" signifies a heterocyclic base attached to the deoxyribose sugar moiety.

TABLE 4

Formulas 7 to 16

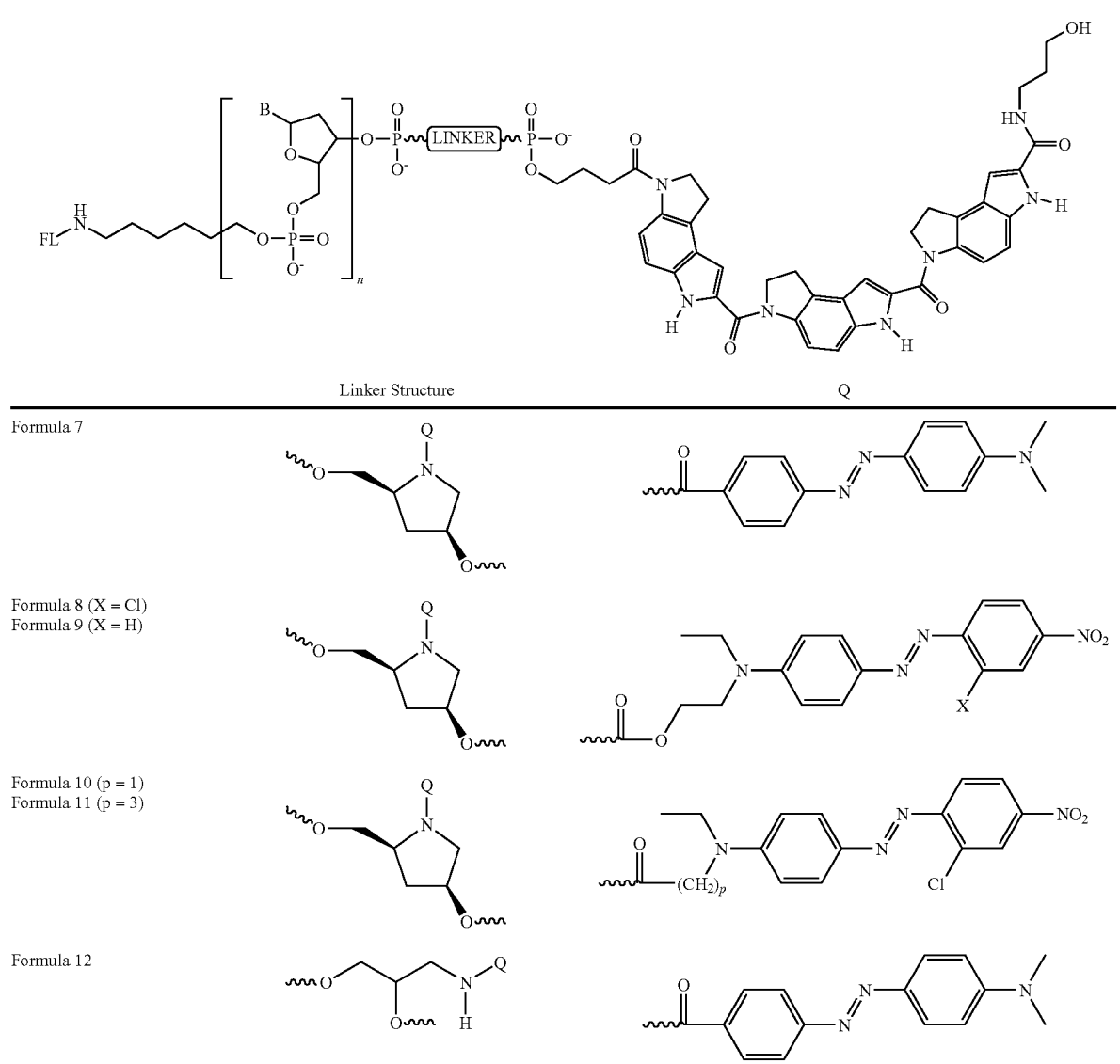

TABLE 4-continued

Formulas 7 to 16

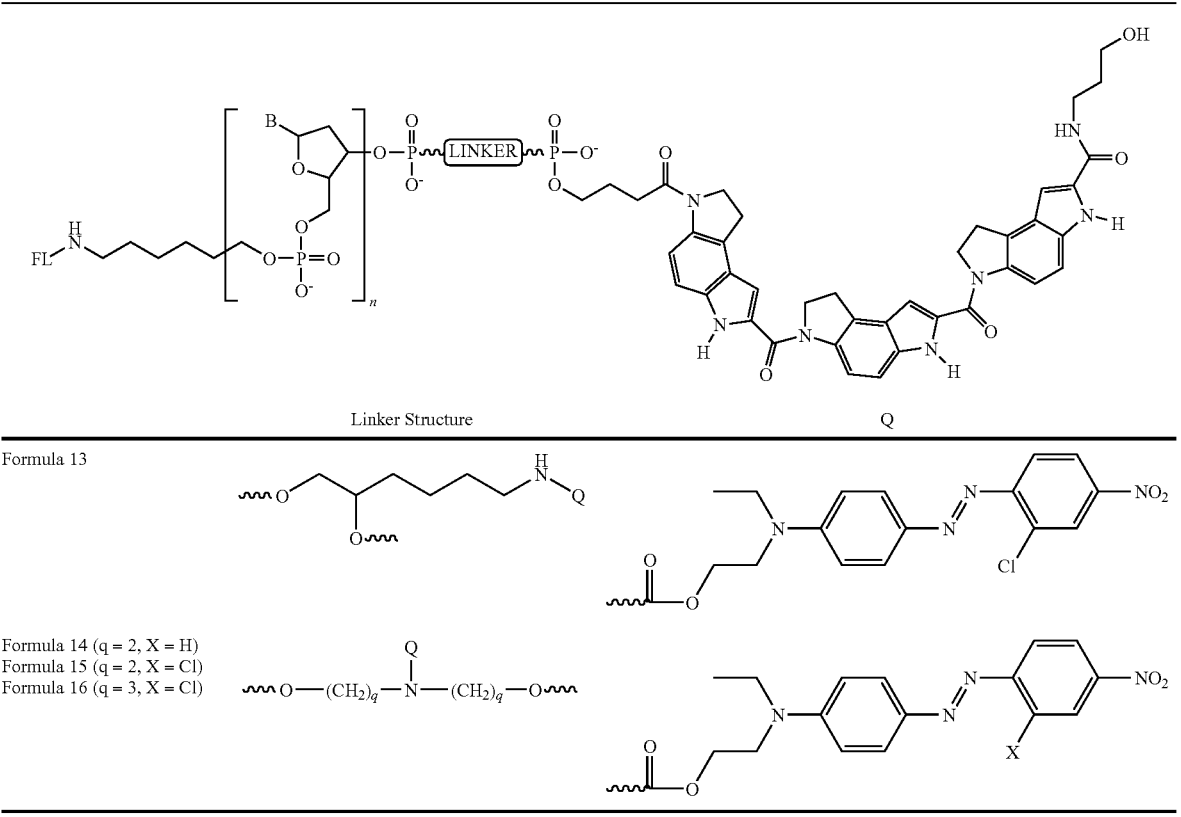

The quenchers incorporated in the compounds represented by Formulas 7-16 are the commercially available 2-[4-(4-nitrophenylazo)-N-ethylphenylamino]ethanol (Disperse Red 1), 2-[4-(2-chloro-4-nitrophenylazo)-N-ethylphenylamino] ethanol (Disperse Red 13) and 2-[4-(dimethylamino)phenylazo]benzoic acid, identified in this invention as Red 1, Red 13 and dabcyl respectively.

UV Properties of Red 13 and Dabcyl Oliqonucleotide Conjugates

Figure 2:
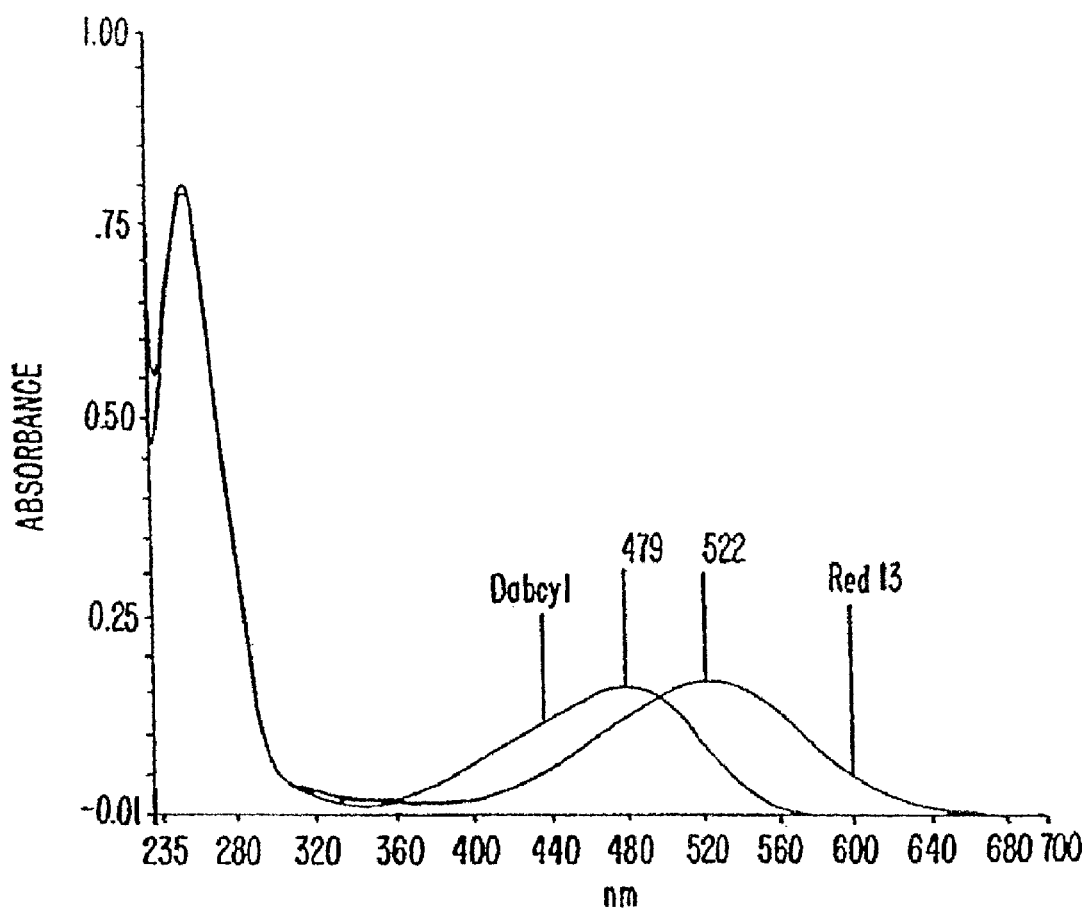
FIG. 2 is a graph showing the UV spectra of Dabcyl- and Red 13 dye-modified DNA probes.

FIG. 2 shows the absorbance properties of the Red 13 chromophore (Formula 8, without $DPI_3$) in comparison to dabcyl (Formula 7, without $DPI_3$ when incorporated at the 3'-end of an otherwise unmodified DNA probe. The broader absorbance (especially at long wavelengths) of the Red 13 chromophore is a clear advantage. Note that the $\lambda_{max}$ for Red 13 is at 522 nm whereas the $\lambda_{max}$ for dabcyl is 479 nm. The absorbance of Red 13 is ideal for quenching of fluorescein (emission max=525 nm) but also overlaps with the fluorescence emission of other common laser dyes.

Quenching Properties of $DPI_3$ Probes with Various Quenchers and Linkers.

For the 10 fluorogenic probes described in Formulas 7 to 16 the fluorescence of a standard solution of each probe was measured before and after digestion with snake venom phosphodiesterase (PDE), as described in the EXPERIMENTAL section. This PDE assay allows the quenching properties of each probe to be compared. Fluorescence of the digested probe (signal) divided by the initial fluorescence (noise) gave a signal to noise ratio (SIN), presented in Table 5. Larger numbers for S/N reflect more efficient fluorescent quenching (lower fluorescent background) of the intact probe.

TABLE 5

EFFECT OF DIFFERENT QUENCHERS AND LINKERS ON FLUOROGENIC PROBES SHOWN IN FORMULAS 7-16.

| Formula # (quencher) | S/N[a] (FL = FAM) | S/N[a] (FL = TAMRA) |
|---|---|---|
| 7 (dabcyl) | 16 | 13 |
| 8 (Red 13) | 21 | 21 |
| 9 (Red 1) | 24 | 21 |
| 10 (Red 13) | 13 | 33 |
| 11 (Red 13) | 27 | 21 |
| 12 (dabcyl) | 13 | 7 |
| 13 (Red 13) | 23 | 21 |
| 14 (Red 1) | 19 | 3 |
| 15 (Red 13) | 24 | 4 |
| 16 (Red 13) | 22 | 24 |

[a]Signal to noise (S/N) was determined using the phosphodiesterase assay described in Example 13. The ODN sequence was 5'-gagggatgtaaaaat (SEQUENCE ID. No. 1). The fluorophores ($R_2$) studied here is either 6-carboxyfluorescein (6-FAM) or 6-carboxytetramethylrhodamine (TAMRA).

It is clear from the data in Table 5 that the Red 13 chromophore and the closely related Red 1 chromophore are better quenchers for both FAM and TAMRA with a variety of linkers than dabcyl. The linker can affect quenching by the Red 13 chromophore. For example, Formula 14 and Formula 15 worked well with FAM, but had poor quenching efficiency for TAMPA. It is somewhat surprising that dabcyl worked so well, especially for the TAMRA probes. As described below, effective FRET quenching by dabcyl is a specific case for MGB probes.

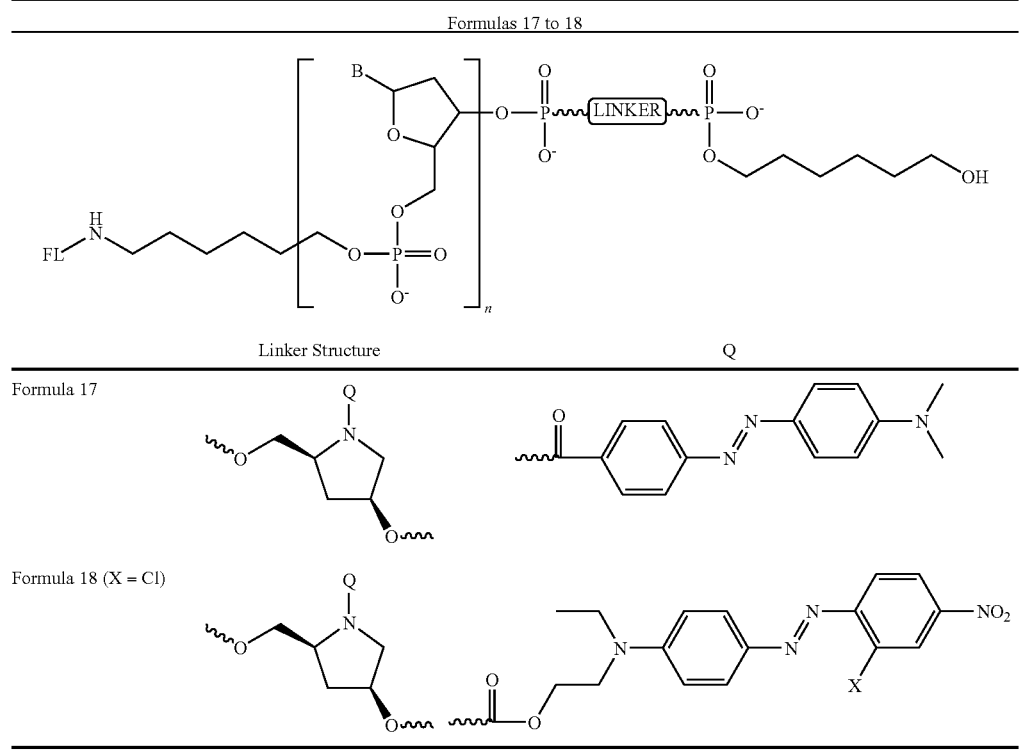

Formulas 17 to 18

Linker Structure

Formula 17

Formula 18 (X = Cl)

Comprarison of Quenchin Pro erties of DPI$_3$ Probes and Probes without DPI$_3$.

To further illustrate the advantages of the Red 13 quencher chromophore, fluorogenic probes with a 3'-hexanol blocking group (without MGB) were compared. The structure and fluorescent properties of 13 fluorogenic probes with the same sequence were compared using the PDE assay. A red-sensitive detector was used in this study (Table 6) whereas a blue-sensitive detector was used in the study shown in Table 5 (S/N for identical ODNs are different because different detectors have different sensitivities for the same fluorophore). The following structural variables are summarized in Table 6: Probe type (no-MGB vs. MGB), Quencher (dabcyl vs. Red 13 vs. Red 13 amide), and Reporter dye (FAM vs. TAMRA).

TABLE 6

FLUORESCENT PROPERTIES OF OLIGONUCLEOTIDES WITH VARIOUS QUENCHERS/FLUOROPHORES1.

| Formula # | Probe type | Quencher | FAM (S/N) | TAMRA (S/N) |
|---|---|---|---|---|
| 17 | no-DPI$_3$ | dabcyl | 4.7 | 3.9 |
| 18 | no-DPI$_3$ | Red 13 | 11.6 | 5.8 |
| 7 | DPI$_3$ | dabcyl | 23 | 23.5 |
| 8 | DPI$_3$ | Red 13 | 35 | 108 |

TABLE 6-continued

FLUORESCENT PROPERTIES OF OLIGONUCLEOTIDES WITH VARIOUS QUENCHERS/FLUOROPHORES1.

| Formula # | Probe type | Quencher | FAM (S/N) | TAMRA (S/N) |
|---|---|---|---|---|
| 30 (R1 = 2-Cl, t = v = 3) | DPI$_3$ | Red 13 amide | 48 | 97 |

1Signal to noise (S/N) was determined using the phosphodiesterase assay described above. The ODN sequence was 5'-gagggatgtaaaaat (SEQUENCE ID. No. 1). The linker structure of the dabcyl or Red 13 quenchers (Q) is shown in Formulas 7 and 8 respectively. The linker structure of the Red 13 amide is shown in 30 Reaction Scheme 7, R$_0$ is 4-NO$_2$, R$_1$ = 2-Cl, R$_2$ = R$_3$ = R$_4$ = –H; t = v = 3.

As can be seen from the data in Table 5, for probes which do not contain DPI$_3$, the dye Red 13 quencher works better than dabcyl for both FAM and TAMRA. In DPI$_3$ containing probes, the dye Red 13 works better in combination with FAM and much better in combination with TAMRA. Both 8 and 30 work better in DPI$_3$-containing probes with both fluorophores, with 30 showing the best S/N ratio for FAM. As a result, the Red 13 chromophore is a more efficient quencher than dabcyl for long wavelength fluorescent reporter groups. For the most commonly used fluorophore (FAM) a 2.5-fold increase in S/N was observed for standard (no-DPI$_3$) probes. This improved quenching by Red 13 is consistent with the increased spectral overlap presented in FIG. 2 and a standard FRET mechanism. The increased S/N of both 8 and 30 when incorporated into the DPI$_3$ probes is dramatic and surprising. The combination of the Red 13 quencher and the DPI$_3$ resulted in a 10-fold increase in S/N for FAM quenching and a 28-fold increase in S/N for TAMRA quenching.

It is surprising and that the DPI$_3$ residue helps improve fluorescent quenching by the dabcyl and Red 13 chromophores. Without wishing to be bound by theory, it is presently postulated that the random coil conformation of the fluorogenic probe in solution is more structured in the DPI$_3$ probes such that the average distance between the fluorophore and quencher is closer than in probes without MOB. This closer average distance in the DPI$_3$ probes (tighter coil) would give rise to more efficient FRET. The exact nature of this interaction is not known, but UV spectra of the quencher and dye chromophores are not affected by the DPI$_3$. This is in contrast to the fluorogenic hairpin probes where the UV spectra are changed by the constrained conformation (collisional quenching).

Performance of Fluorogenic DPI$_3$ Probes in a "Real-Time" PCR Assay.

Figure 3:
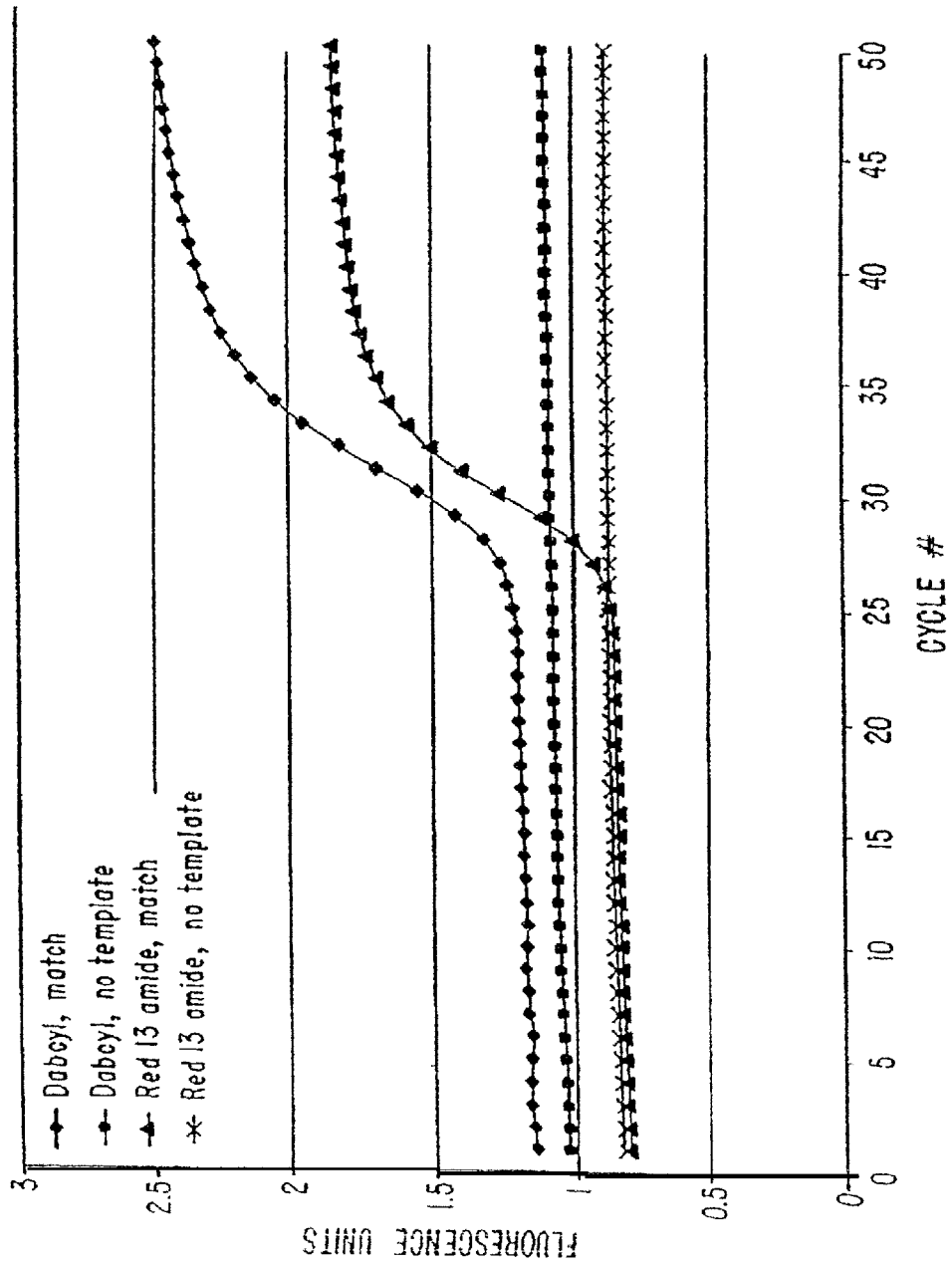
FIG. 3 is a graph showing the performance of fluorogenic MGB probes in a "real-time" PCR assay.

DPI$_3$ probes prepared with 5'-fluorescein and the Red 13 amide linker were tested in the 5'-nuclease assay to see if the hybridization properties were compatible with the linker system. As shown in FIG. 3, both dabcyl and Red 13 worked as quenchers for fluorescein in the 5'-nuclease assay when used in MGB probes. Red 13 performed better than dabcyl as evidenced by the lower initial fluorescence (background) and the higher plateau after PCR. Current commercially available thermal-cycling fluorimeters can not read longer wavelength dyes in real-time PCR, but the Red 13 chromophore was shown to give a good S/N with TAMRA containing probes in an end point analysis after PCR.

According to another general method, the 5'-fluorophore-ODN-Q-MGB conjugates of the instant invention have improved performance in assays designed to detect DNA targets by direct hybridization. A basic description of this method is found in U.S. Pat. No. 5,876,930. In this assay format, the non-hybridized probes (quenched by FRET) become fluorescent upon forming a rigid duplex structure, thereby separating the quencher and fluorophore.

Red 13 Chromophore Quenches a Broad Range of Fluorescent Reporter Groups

A series of DPI$_3$ probes with the Red 13 amide were prepared with several different fluorescent reporter groups to examine the effective range of quenching. Probes were digested with PDE as usual and showed good S/N for dyes which emit from 458-665 nm.

TABLE 7

PERFORMANCE OF FLUOROGENIC DPI$_3$ PROBES WITH VARIOUS FLUOROPHORES.

| Fluorophore (FL) | Ex 8 (nm) | Em 8 (nm) | S/N |
|---|---|---|---|
| coumarin | 378 | 458 | 32 |
| FAM | 488 | 522 | 63 |
| Cy3 | 541 | 565 | 61 |
| TAMRA | 547 | 582 | 37 |
| resorufin | 549 | 595 | 110 |
| Cy5 | 641 | 665 | 36 |

The structure of the fluorogenic probes was FL-ODN-Q-CDPI$_3$ where Q is the Red 13 amide and the ODN sequence was 5'-GTC CTG ATT TTA C (SEQUENCE Id. No. 2). The fluorophores FAM, TAMRA, cy3 and cy5 were incorporated using commercially available phosphoramidite reagents. The coumarin and resorufin fluorophores were incorporated using phosphoramidites 34 and 37 which were prepared as described below.

Figure 4:
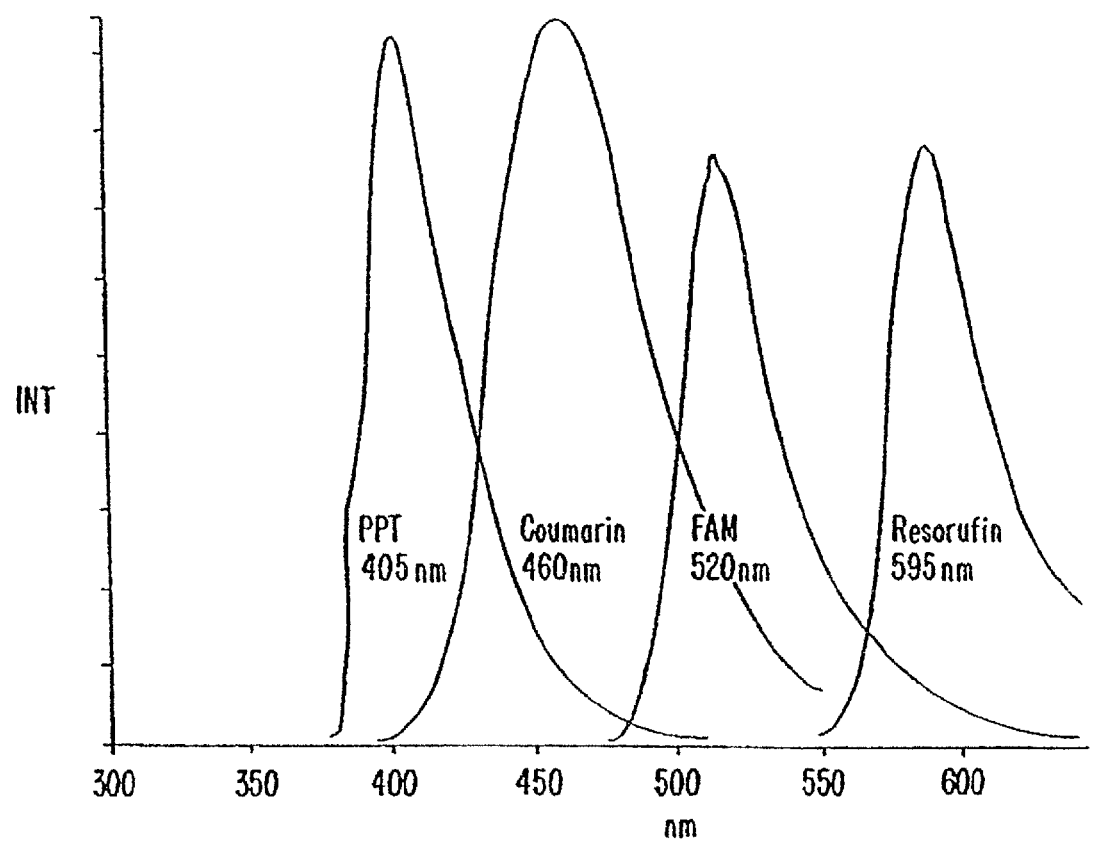
FIG. 4 is a graph showing the fluorescent spectra of violet, FAM and resorufin dye containing DNA probes.

The fluorescent emission is well separated from FAM, as shown in the overlaid spectra in FIG. 4. As shown in Table 7, the resorufin fluorescence is also quenched by the Red 13 chromophore. Thus the resorufin phosphoramidite has excellent properties for use in FRET probes and in combination with FAM for multicolor analysis.

As shown in Table 7, the coumarin fluorescence is also quenched by the Red 13 chromophore. Thus, the coumarin phosphoramidite reagent can be incorporated in FRET probes and particularly in combination with FAM for multicolor analysis.

FRET-Based Enzyme Substrates

The improved quencher molecules can be used in other FRET based assay systems. According to another general application of the invention, a quencher molecule and fluorophore are attached to an enzyme substrate, which through its catalytic action on this Q-substrate-fluorophore conjugates cleaves and separates the Q and fluorophore molecules. For example, the pentafluorophenyl activated ester 11 shown in Reaction Scheme 3 can be used for labeling lysine residues of peptides for studying proteolytic enzymes.

EXAMPLES

General Experimental

All air and water sensitive reactions were carried out under a slight positive pressure of argon. Anhydrous solvents were obtained from Aldrich (Milwaukee, Wis.). Flash chromatography was performed on 230-400 mesh silica gel. Melting points were determined on a Mel-Temp melting point, apparatus in open capillary and are uncorrected. Elemental analysis was performed by Quantitative Technologies Inc. (Boundbrook, N.J.). UV-visible absorption spectra were recorded in the 200-400-nm range on a UV-2100 (Shimadzu) or a Lambda 2 (Perkin Elmer) spectrophotometers. $^1$H NMR spectra were run at 20EC on a Bruker WP-200 or on a Varian XL-200 spectrophotometer; chemical shifts are reported in ppm downfield from Me$_4$Si. Thin-layer chromatography was run on silica gel 60 F-254 (EM Reagents) aluminum-backed plates.

Example 1

This example illustrates the preparation of a quencher phosphoramidite reagent according the methods outlined in Reaction Scheme 1. The product is 2-({4-[(2-Chloro-4-nitrophenyl)diazenyl]phenyl}ethylamino)ethyl (2S,4R)-2-{[bis(4-methoxyphenyl)phenylmethoxy]methyl}-4-{[bis(methylethyl)amino](2-cyano-ethoxy)phosphinooxy}pyrrolidinecarboxylate (5a).

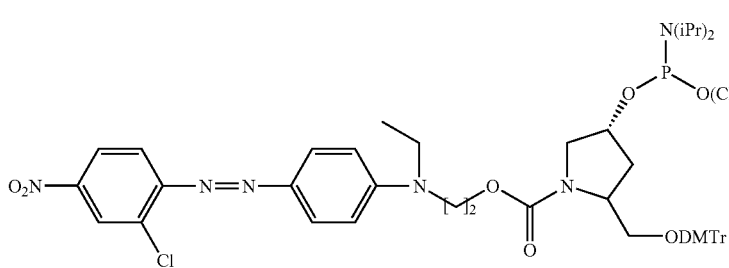

2-({4-[(2-Chloro-4-nitrophenyl)diazenyl]phenyl}ethylamino)ethyl (5S,3R)-3-hydroxy-5-(hydroxymethyl)pyrrolidinecarboxylate (3a)

A solution of 2-[4-(2-chloro-4-nitrophenylazo)-N-ethylphenylamino]ethanol (Disperse Red 13, Aldrich Chemical Co., 9.0 g, 25.80 mmol) and 4-nitrophenyl chloroformate (Aldrich Chemical Co., 9.4 g, 46.61 mmol) in 90 ml of anhydrous pyridine was stirred at 70° C. for 40 min, affording intermediate 2a. Ethanol (5.0 ml) was added to the reaction solution followed by trans-hydroxyprolinol (Reed et al., Bioorg. Chem. 2:217-225 (1991) (42 ml of a 0.5 M solution in ethanol) and triethylamine (3.2 ml). The resultant solution was stirred for 30 min at 70° C. The solution was evaporated to dryness and the residue was suspended in 1 liter of water and extracted with ethyl acetate (3×500 ml). The pooled extracts were dried over sodium sulfate, filtered and evaporated. The residue was purified by silica gel chromatography eluting with a gradient of 0-10% methanol in ethyl acetate. The pure product fractions were evaporated and precipitated from ethyl acetate-ether: 9.2 g (59%); TLC (ethyl acetate), $R_f$=0.25. $^1$H NMR (DMSO-$d_6$) δ 8.43 (1H, d, J=2.5 Hz), 8.25 (1H, dd, J=9.0 and 2.4 Hz), 7.86 (2H, d, J=9.1 Hz), 7.78 (1H, d, J=9.0 Hz), 6.96 (2H, d, J=9.3 Hz), 4.88 (1H, m), 4.67 (1H, t, J=5.7 Hz), 4.19 (3H, m), 3.80 (1H, m), 3.73 (2H, t, J=5.4 Hz), 3.56 (2H, q), 3.46 (1H, t, J=4.7 Hz), 3.27 (1H, m), 1.94 (1H, m), 1.79 (1H, m), 1.17 (3H, t, J=6.8 Hz). Anal. Calcd for $C_{22}H_{26}ClN_5O_6$+0.2 $H_2O$: C, 53.32; H, 5.37; N, 14.13. Found: C, 53.24; H, 5.25; N, 13.99.

2-({4-[(2-Chloro-4-nitrophenyl)diazenyl]phenyl}ethylamino)ethyl (5S,3R)-5-{[bis(4-methoxyphenyl)phenylmethoxy]methyl}-3-hydroxypyrrolidinecarboxvlate (4a)

To a solution of 3a (9.1 g, 18.53 mmol) in 130 ml of anhydrous pyridine was added 6.26 g of dimethoxytrityl chloride. The solution was stirred for 3 h. at room temperature and then poured into 300 ml of 5% sodium bicarbonate solution. The mixture was extracted with ethyl acetate (2×300 ml) and the combined extracts were dried over sodium sulfate, filtered and evaporated. The residue was purified by silica gel chromatography eluting with a gradient of 20-0% hexane in ethyl acetate followed by a gradient of 0-2% methanol in ethyl acetate. The chromatography eluent also contained 1% triethylamine. The pure product fractions were combined affording an amorphous solid: 12.66 g (86%); TLC (ethyl acetate), $R_f$=0.44. $^1$H NMR (DMSO-$d_6$) δ 8.45 (1H, s), 8.26 (1H, d, J=8.9 Hz), 7.82 (3H, m), 7.27 (4H, m), 7.16 (5H, m), 6.95-6.79 (6H, m), 4.95 (1H, m), 4.32 (1H, m), 4.14 (1H, m), 3.99 (2H, m), 3.73 (1H, m), 3.69 (6H, s), 3.56 (1H, m), 3.40-3.30 (2H, m), 3.14 (1H, m), 2.10-1.82 (2H, m), 1.16 (3H, m), 1.06 (3H, t, J=6.5 Hz). Anal. Calcd for $C_{43}H_{44}ClN_5O_8$+0.2 $H_2O$: C, 64.73; H, 5.61; N, 8.78. Found: C, 65.08; H, 5.70; N, 8.31.

2-({4[(2-Chloro-4-nitrophenyl)diazenyl]phenyl}ethylamino)ethyl (2S,4R)-2-{[bis(4-methoxyphenyl)phenylmethoxy]methyl}-4-{[bis(methylethyl)amino](2-cyano-ethoxy)phosphinooxy}pyrrolidinecarboxylate (5a)

To a solution of 4a (12.63 g, 15.91 mmol) dissolved in 440 ml of anhydrous methylene chloride, containing 8.0 ml of N,N-diisopropylethylamine, was added 5.94 ml of 2-cyanoethyl diisopropylchlorophosphoramidite. The solution was stirred 30 min under argon at room temperature. The reaction mixture was treated with 10 ml of methanol and poured into 400 ml of 5% sodium bicarbonate solution. The organic phase was dried over sodium sulfate and evaporated. The residue was purified by silica gel chromatography eluting with a gradient of 40-20% hexane in ethyl acetate (2% triethylamine). The pure product fractions were evaporated affording an amorphous solid: 14.75 g (93% yield). $^{31}$P NMR (DMSO-$d_6$) δ 146.93 (singlet). Anal. Calcd for $C_{52}H_{61}ClN_7O_9$+1.0 $H_2O$: C, 61.68; H, 6.27; N, 9.68. Found: C, 61.44; H, 6.47; N, 9.35.

Example 2

This example illustrates the preparation of a solid support (CPG) bound quencher-linker conjugate (12 in Reaction Scheme 3) that can be used for the preparation of additional reagents described herein.

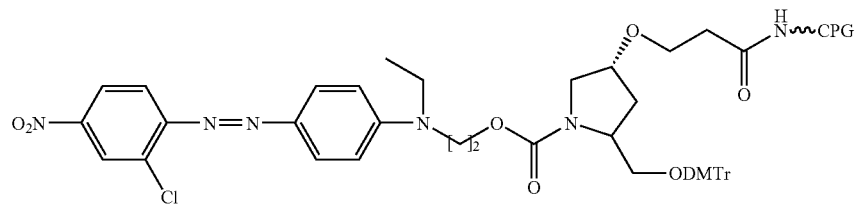

RED 13-pyrrolidine-DMTr-CPG, 12

Synthesis of pentafluorophenyl ester (11) and RED 13-pyrrolidine-DMTr-CPG (12) Reactions Scheme 3.

The pentafluorophenyl ester (11) is synthesized by the same method used for the synthesis of Compound 22 as described in Example 4 and Reaction Scheme 5.

RED 13-pyrrolidine-DMTr-CPG (12)

10 g of LCAA-CPG was combined with 5 ml of a 0.3 M solution of 11 in DMF and agitated gently overnight, when it was filtered and washed with 2×100 mL of DMF, 2×100 mL of acetonitrile, and 2×100 mL of ether. Traces of ether were removed in vacuo (oil pump). Unreacted amino groups were acetylated by treating the CPG with 40 mL of dry pyridine and 5 mL of acetic anhydride. After swirling for 1.5 h, the CPG was filtered and washed with 2×100 mL of DMF, 2×100 mL of acetonitrile, and 2×100 mL of ether. Traces of ether were removed in vacuo (oil pump). The CPG was analyzed for MMT loading by treating 3-5 mg of CPG in 25 mL of 1:1/70% perchloric acid:methanol. The absorbance of the released MMT cation was recorded at 472 nm and loading level was adjusted to be between 30-40 mmol/g of CPG using the equation:

$$MMT \text{ loading } (mmol/g) = \frac{A472 \times \text{volume (in mL)} \times 14.3}{\text{wt of CPG (mg)}}$$

Example 3

This example illustrates the preparation of MGB precursors as described in Reaction Scheme 4 and further developed in Reaction Schemes 5-7. Specifically, 2-(4-nitrophenyl)ethyl 3-(pyrrolo[4,5-e]indolin-7-ylcarbonyl)pyrrolo[4,5-e]indoline-7-carboxylate (17, Reaction Scheme 4) is described.

2-(4-Nitrophenyl)ethyl 3-[(tert-butyl)oxycarbonyl] pyrrolo[4,5-e]indoline-7-carboxvlate (14)

Ten grams (33.1 mmol) of 3-[(tert-butyl)oxycarbonyl]pyrrolo[3,2-e]indoline-7-carboxylic acid (Boger et al., *J. Org. Chem.* 52:1521 (1987)), well dried, are placed into an argon filled flask, and 84 mL of THF and 10.4 mL (66.2 mmol) of diethyl azodicarboxylate (DEAD) are added. A dropping funnel is placed atop the flask (flushed with argon) and a water bath (to cool the flask) is placed under it. A solution of 17.3 g (66 mmol) of triphenylphosphine and 6.64 g (39.7 mmol) of 2-(p-nitrophenyl) ethanol in 160 mL of ethyl ether is made. This solution is added to the dropping funnel, and then to the reaction flask, dropwise, with stirring. The reaction is allowed to proceed for an hour, at which time, a TLC analysis is done (2:1 hexanes/ethyl acetate) examined by UV (254 nm) to determine whether the reaction is complete. If it is complete, then the baseline spot (bluish) will disappear and the product, with an $R_f$ of 0.55, will appear as a dark spot. Often, especially if the reactants are not entirely dry, another portion of triphenylphosphine and DEAD are required. If so, a tenth of the original amounts is usually sufficient, i.e., 1.73 g of triphenylphosphine and 1.04 mL of DEAD. These can be added neat to the stirred solution. Allow to react another hour, after which another TLC analysis usually reveals complete reaction. The product usually precipitates out in part; this is collected bt filtration and washed with methanol, then recrystallized by dissolving in a minimum amount (typically, 80-100 ml) of warm acetone and adding four times that volume of warm methanol. Cool to 4° C. for several hours or perhaps overnight. The supernatant from the original precipitation is saved and evaporated to a syrup or until dry. It too is dissolved in a minimum amount of warm acetone; typically about 100-120 mL of warm acetone. The total amount or acetone used for the two recrystallizations is usually approximately 200 mL. As before, an amount of warm methanol equal to four times the amount of acetone is added. The solution is cooled; crystallization begins almost at once but is allowed to continue several hours to overnight. The recrystallizations are quite efficient, but the product from the reaction supernatant is usually not quite as pure and is purified by recrystallization. The yield is approximately 85%. (mp 191-193° C.) $^1$H NMR (DMSO-d6) δ 11.83 (s, 1H), 8.18 (d, J=8.5 Hz, 2H), 7.84 (br s, 1H), 7.64 (d, J=8.5 Hz, 2H), 7.25 (d, J=8.8 Hz), 6.96 (s, 1H), 4.56 (t, J=6 Hz, 2H), 4.00 (t, J=8.8 Hz, 2H), 3.21 (m, 4H), 1.51 (s, 9H). Combustion Analysis: Found: C, 63.16%; H, 5.56%; N, 9.45%. Calculated for 0.4 mole added water: C, 62.8%; H, 5.7%; N, 9.16%.

2-(4-Nitrophenyl)ethyl pyrrolo[4,5-e]indoline-7-carboxylate (15)

Two grams (4.43 mmol) of 14 are weighed into a round bottomed flask. Then, in a fume hood, 25 mL (325 mmol) of trifluroacetic acid is added, and the flask is capped and stirred. The solid dissolves in about a minute. The mixture is stirred for 1 hour, at which time deprotection will be done (HPLC can be used as a check). The acid is evaporated on a rotary evaporator (use a trap) and the product is dissolved in 100 mL of methylene chloride. This is extracted twice with 100 mL of half to ⅔ saturated sodium bicarbonate solution. The aqueous layers are back-extracted once with ~50 mL of methylene chloride and this is combined with the rest. The organic layer is dried over sodium sulfate twice and evaporated to give a brown solid. If desired, this material can be recrystallized by diluting a very concentrated solution in methylene chloride with methanol and cooling.

Yields approaching 100% are usually obtained. mp 192-194° C. $^1$H NMR (DMSO-d6) δ 11.51 (s, 1H), 8.18 (d, J=8.5 Hz, 2H), 7.63 (d, J=8.5 Hz, 2H), 7.11 (d, J=8.5 1H), 6.80 (s, 1H), 6.70 (d, J=8.5 Hz), 5.03 (br s, 1H), 4.54 (t, J=6.4 Hz, 2H), 3.46 (t, J=8.6 Hz, 2H), 3.19 (m, 2H), 3.04 (t, J=8.6 Hz, 2H). Combustion Analysis: Calculated for $C_{19}H_{17}N_3O_4$: C,64.94%; H, 4.88%; N, 11.96%. Found: C, 65.50%; H, 4.70%; N, 11.64%

2-(4-Nitrophenyl)ethyl 3-({3-[(tert-butyl)oxycarbonyl]pyrrolo[4,5-e]indolin-7-yl}carbonyl)pyrrolo[4,5-e]indoline-7-carboxylate (16)

3.09 grams (8.8 mmol) of 15 is mixed with 2.66 grams (8.8 mmol) of 13 (Boger et al., *J. Org. Chem.* 52:1521(1987)), and 46 mL of DMF is added. Then 3.85 grams (8.77 mmol) of 1-[3-(dimethylamino)propyl]-3-ethylcarbodiimide hydrochloride are added. The mixture is stirred for about three hours. The mixture is initially homogeneous, but as the stirring proceeds, a precipitate of the product forms. The solvent DMF is evaporated under a high vacuum, and about 100 mL of methanol is added. The mixture is swirled and filtered in a sintered glass funnel, then thoroughly washed with 3×50 mL portions of methanol. Then it is dried in vacuo. Yields usually approach 100 percent. mp: 132-134° C. $^1$H NMR (DMSO-d6) δ: 11.93 (s, NH, 1H), 11.62 (s, NH, 1H), 8.30 (br s, aromatic proton, 1H), 8.27 (br s, aromatic proton, 1H), 8.19 (d, aromatic protons, J=8.3 Hz, 2H), 7.65 (d, aromatic protons, J=8.3 Hz, 2H), 7.34 (d, J=9 Hz, aromatic proton, 1H), 7.29 (d, J=9 Hz, aromatic proton, 1H), 7.07 (s, aromatic proton, 1H), 6.98 (s, aromatic proton, 1H), 4.60 (m, aliphatic protons, 4H), 4.02 (t, J=8.5 Hz, aliphatic protons, 2H), 3.40 (t, J=8 Hz, aliphatic protons, 2H), 3.24 (m, aliphatic protons, 4H), 1.52 (s, 3×$CH_3$, 9H). Combustion Analysis: Calculated: C, 66.13%; H, 5.23%; N, 11.02%. Found: C, 65.94%; H, 5.19%; N, 11.07%.

2-(4-Nitrophenyl)ethyl 3-(pyrrolo[4,5-e]indolin-7-ylcarbonyl)pyrrolo[4,5-e]indoline-7-carboxylate (17)

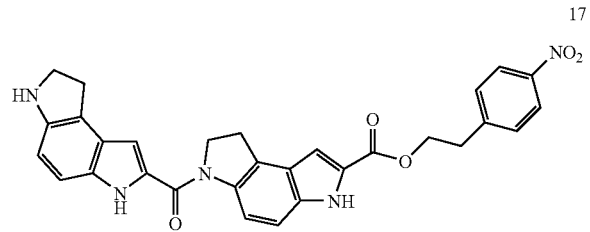

5 grams of 16 are placed in a flask. 100 mL of trifluoroacetic acid is added, and the mixture is stirred. After an hour, the acid is evaporated on a rotary evaporator and 100 mL saturated sodium bicarbonate solution and 100 mL of water are added. The mixture is agitated or sonicated for ~½ hours, then filtered and washed with water and then methanol, and dried in vacuo. The material may be recrystallized. It is dissolved in a minimum amount of warm DMF, and then approximately a threefold portion of methanol is added and the solution is sonicated a few minutes. A cream to brown material crystallizes out. This is washed with methanol, and dried in vacua The yield approaches theoretical values. $^1$H NMR (DMSO-d6) δ 11.96 (s, NH, 1H), 11.71 (s, NH, 1H), 8.30 (br s, aromatic proton, 1H), 8.27 (br s, aromatic proton, 1H), 8.19 (d, aromatic protons, J=8.5 Hz, 2H), 7.66 (d, aromatic protons, J=8.3 Hz, 2H), 7.34 (m, aromatic protons, 2H), 7.08 (s, aromatic proton, 1H), 7.03 (s, aromatic proton, 1H), 4.60 (m, aliphatic protons, 4H), 3.68 (t, J=8 Hz, aliphatic protons, 2H), 3.40 (t, J=8 Hz, aliphatic protons, 2H), 3.24 (m, aliphatic protons, 4H). Combustion Analysis: Found: C, 63.55%; H, 4.42%; N, 11.95%. Calculated, for ½ mole sodium bicarbonate contaminant: C, 63.43%; H, 4.45%; N, 12.13%.

Example 4

This example illustrates the preparation of Q-W-MGB conjugates according to Reaction Schemes 5 and 6. Specifically, 2,3,4,5,6-pentafluorophenyl 3-[4-({3-[bis(4-methoxyphenyl)phenylmethoxy]propyl}-{4-[(2-chloro-4-nitrophenyl)diazenyl]phenyl}amino)butanoyl]pyrrolo[4,5-e]indoline-7-carboxylate (24, Reaction Scheme 5), is prepared.

Ethyl 4-[(3-hydroxypropyl)phenylamino]butanoate (19)

A mixture of 3-(phenylamino)propan-1-ol (Huang et al., *J. Org. Chem.*; 58(23):6235-6246(1993)) (65.6 g, 0.43 mol), ethyl 4-bromobutyrate (104.5 g, 0.54 mol) and 100 mL of ethyldiisopropylamine is stirred at 100° C. for 1 h. The reaction is cooled to room temperature and partitioned between water 400 mL and ethyl acetate (500 mL). The organic layer is washed with saturated $NaHCO_3$, brine and dried over $Na_2SO_4$. The oil obtained after concentration is chromatographed on silica eluting with 10% $EtOH/CHCl_3$. Concentration of the appropriate fractions affords 115 g (100%) of the desired product as a colorless, viscous oil. $^1$H NMR ($CDCl_3$) δ 7.23 (m, 2H), 6.72 (m, 3H), 4.14 (q, J=7 Hz, 2H), 3.72 (t, J=6 Hz, 2H), 3.43 (t, 7 Hz, 2H), 3.34 (t, 7 Hz, 2H), 2.35 (t, 7 Hz), 1.88 (m, 4H), 1.26 (t, 7 Hz, 3H).

Ethyl 4-({4-[(2-chloro-4-nitrophenyl)diazenyl]phenyl}(3-hydroxypropyl)amino)butanoate (20)

2-Chloro-4-nitroaniline 2.5 g (10 mmol) is placed into a 125 mL flask and 6 mL of water is added. Agitation and sonication partially dissolves the yellow chloronitroaniline. Then the stirred solution is cooled with ice in a fume hood and 15.8 mL of concentrated (~12 M) HCl is added. Most of the yellow material dissolves at this point. The flask is fitted with a dropping funnel, and a solution of 1.51 g (21.9 mmol) sodium nitrite in 3-4 mL of water is added to the dropping funnel and slowly added to the solution in the flask with stirring, over about 20 minutes. When this is complete, 0.6 g (~21 mmol) of urea is added followed by 2.73 g of ethyl 4-[(3-hydroxypropyl)phenylamino]butanoate as a solution in 8.2 mL acetic acid. After a minute 20 g of sodium acetate in -50 mL of water is added. The mixture is allowed to stir for an hour at room temperature. Most of the product is separated as an emulsion. The mixture is partitioned between ethyl acetate and water. The organic layer is washed with $NaHCO_3$ (3×50 ml), brine and dried over anhydrous sodium sulfate. Then the organic solvents are evaporated to a syrup. The crude product is chromatographed on silica gel (1.5×20 inches) eluting with 50% ethyl acetate/hexane. The appropriate fractions are collected, combined, evaporated (30-40 degrees), and dried in a vacuum. The product is a dark oil. The yield is approximately 68-70%. $^1$H NMR (DMSO-d6) δ 8.42 (d, J=2.5 Hz, aromatic proton, 1H), 8.24 (dd, $J_1$=9 Hz, $J_2$=2.5 Hz, aromatic proton, 1H), 7.86 (d, J=9 Hz, 2H), 7.77 (d, J=9 Hz, 1H), 6.92 (d, J=9 Hz, aromatic protons, 2H), 4.67 (t, J=6 Hz, OH, 1H), 4.07 (q, J=7 Hz, $CH_2O$, 2H), 3.5 (m, aliphatic protons, 6H), 2.40 (t, J=7 Hz, aliphatic protons, 2H), 1.84 (m, aliphatic protons, 2H), 1.72 (m, aliphatic protons, 2H), 1.18 (t, J=7 Hz, $CH_3$, 3H).

4-({4-[(2-Chloro-4-nitrophenyl)diazenyl]phenyl}(3-hydroxypropyl)amino)butanoic acid To a stirred solution of 20 (4.48 g, 10 mmole) in 40 mL of THF added 40 mL of ethanol followed by a solution of KOH (0.84 g, 15 mmol) in 20 mL of water and 20 mL of ethanol. The mixture is stirred overnight and concentrated. The residue suspended in 125 mL of water, treated with 2.6 mL (~3 eqv.) of acetic acid, and cooled to 4° C. The resulting solid is filtered off, washed with water, and dried. Yield is quantitative. $^1$H NMR (DMSO-d6) δ 8.42 (d, J=2.5 Hz, aromatic proton, 1H), 8.23 (dd, $J_1$=9 Hz, $J_2$=2.5 Hz, aromatic proton, 1H), 7.82 (d, J=9 Hz, 2H), 7.90 (d, J=9Hz, 1H), 7.03 (d, J=9 Hz, aromatic protons, 2H), 4.8 (br s, OH, 1H), 3.5 (m, aliphatic protons, 6H), 1.86 (t, J=6 Hz, aliphatic protons, 2H), 1.72 (m, aliphatic protons, 4H).

4-({3-[Bis(4-methoxyphenyl)phenylmethoxy]propyl}-{4-[(2-chloro-4-nitrophenyl)diazenyl]phenyl}amino)butanoic acid (21)

4.21 g (10 mmol) of the acid from the previous step is placed into a 250 mL round bottom flask. Dry pyridine (50-100 ml) is added and evaporated (30-40 degrees) with a rotary evaporator. The process is repeated once or twice to remove all traces of water. Dry pyridine (80 mL) is added to the contents of the flask. Then 4.07 g (12 mmol) of dimethoxytrityl chloride is added. After being stirred for 1 h pyridine is evaporated and the resulting syrup is dissolved in a few milliliters of 18:1:1 methylene chloride/methanol/triethylamine. A silica gel column (~1.5"×20") is prepared with an eluent of 18:1:1 methylene chloride/methanol/triethylamine and the product is run through the column, collecting and combining the appropriate fractions. After the solvents are removed by evaporation the resulting amorphous solid contains some triethylammonium salts in addition to the desired product. The impurity does not interfere with the next step and the product is used without additional purification.

2,3,4,5,6-Pentafluorophenyl 4-({3-[bis(4-methoxyphenyl)phenylmethoxyl]-propyl}-{4-[(2-chloro-4-nitrophenyl)diazenyl]phenyl}amino)butanoate (22)

To the flask containing 21 (10 mmol) is added 7 mL of triethylamine followed by 100 mL of methylene chloride, (2×30 mL) and dried under vacuum. The yield of the desired product is 2.7 g (87%) as a deep-purple solid. $^1$H NMR (DMSO-d6) δ 11.93 (d, J=1.7 Hz, indole NH, 1H), 8.43 (d, J=2.5 Hz, aromatic proton, 1H), 8.3-8.2 (m, aromatic protons, 2H), 7.85-7.75 (m, aromatic protons, 3H), 7.45-7.18 (m, aromatic protons, 10 H), 7.05 (d, J=1.8 Hz, aromatic proton, 1H), 6.97 (d, J=9 Hz, aromatic protons, 2H), 6.87 (d, J=9 Hz, aromatic protons, 4H), 4.12 (t, J=8 Hz, aliphatic protons, 2H), 3.87 (s, ester CH$_3$, 3H), 3.71 (s, CH$_3$, 6H), 3.60 (br t, aliphatic protons, 2H), 3.45 (br t, aliphatic protons, 2H), 3.29 (br t, aliphatic protons, 2H), 3.08 (t, J=5 Hz, aliphatic protons, 2H), 2.5 (br t, obscured by DMSO signal, aliphatic protons, 2H), 1.88 (br m, aliphatic protons, 4H).

2,3,4,5,6-pentafluorophenyl 3-[4-({3-[bis(4-methoxyphenyl)phenylmethoxyl]-propyl}-{4-[(2-chloro-4-nitrophenyl)diazenyl]phenyl}amino)butanoyl]-pyrrolo[4,5-e]indoline-7-carboxylate (24)

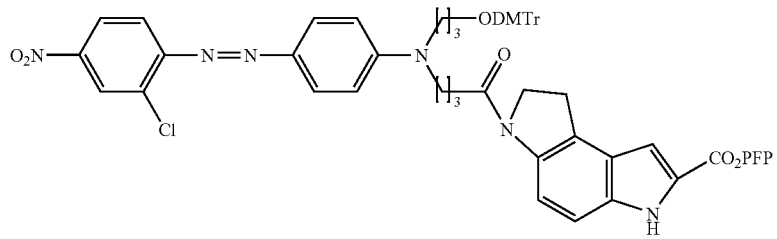

24

2.05 mL of pentafluorophenyl trifluoroacetate (PFP-TFA) is then added. The solution is stirred for half an hour. At the end of this time, the reaction is usually complete. (TLC: 2:1 hexane/ethyl acetate). The solvent is removed on the rotary evaporator to give a syrup which is chromatographed on silica eluting with 1:3 ethyl acetate/hexane. Appropriate fractions are collected, combined, evaporated and dried under vacuum. The yield is 41%. $^1$H NMR (DMSO-d6) δ 8.43 (d, J=2.5 Hz, aromatic proton, 1H), 8.24 (dd, J$_1$=9 Hz, J$_2$=2.5 Hz, aromatic proton, 1H), 7.83 (d, J=9 Hz, aromatic proton, 1H), 7.78 (d, J=9 Hz, aromatic proton, 1H), 7.42-7.15 (m, aromatic protons, 10H), 7.07 (m, aromatic protons, 2H), 7.00-6.80 (m, aromatic protons, 4H), 3.72 (s, 2×CH$_3$, 6H), 3.56 (m, aliphatic protons, 2H), 3.48 (t, J=6.3 Hz, aliphatic protons, 2H), 3.08 (t, J=5 Hz, aliphatic protons, 2H), 2.89 (t, J=7 Hz, aliphatic protons, 2H), 1.95 (m, aliphatic protons, 2H), 1.86 (m, aliphatic protons, 2H).

Methyl 3-[4-({3-[bis(4-methoxyphenyl)phenylmethoxy]propyl}-{4-[(2-chloro-4-nitrophenyl)diazenyl]phenyl}amino)butanoyl]pyrrolo[4,5-e]indoline-7-carboxylate (23)

To a solution of 22 (3.0 g, 3.37 mmol) in 15 mL anhydrous DMF is added triethylamine (0.75 mL) followed by methyl pyrrolo[4,5-e]indoline-7-carboxylate (Boger et al., *J. Org. Chem.* 52:1521 (1987)) (0.8 g, 3.7 mmol). The resultant solution is stored at room temperature for 20 h. The reaction is analyzed by HPLC to confirm its completeness. DMF is removed on a rotary evaporator equipped with an oil pump. The residue, dark syrup is suspended in 50% ethylacetate/hexanes (~25 mL). The mixture is sonicated to initiate the crystallization. The crystals are stirred for 15 min, collected by filtration on a sintered glass funnel, washed with methanol Hydrolysis of the Methyl Ester To a solution of 23 (2.67 g, 2.9 mmol) in 25 mL THF are added methanol (25 mL) and 5% LiOH, monohydrate in H$_2$O (10 mL). The resultant suspension is stirred at 50° C. (bath temperature) for 90 min. by which time a clear solution is obtained. TLC analysis shows no starting material. Solvent is removed under vacuum and the product is partitioned between CH$_2$Cl$_2$ and cold 10% citric acid. The organic phase is neutralized with triethylamine, dried over Na$_2$SO$_4$ and concentrated. The resultant product (amorphous solid) is dried in high vacuum for at least 3 h and used in the next step without additional purification.

PFP Ester Preparation

The product obtained in the previous step is dissolved in 100 mL anhydrous DMF. Triethylamine (2 mL) is added followed by PFP-TFA (2 mL, 4.4 mmol). The reaction is stirred for 30 min and analyzed by HPLC. No starting material, free acid should be observed. DMF is evaporated and the residue, deep purple syrup is suspended in 100 mL MeOH. After stirring for 30 min, a dark precipitate is formed which is collected by filtration on a sintered glass funnel, washed with methanol (3×20 mL) and dried under vacuum (15-30 h). This procedure yields 2.7 g (94%) of the desired product as a purple solid. $^1$H NMR (DMSO-d6) δ 12.45 (d, J=1.8 Hz, indole NH, 1H), 8.43 (d, J=2.5 Hz, aromatic proton, 1H), 8.38 (d, J=9 Hz, aromatic proton, 1H), 8.24 (dd, J$_1$=9 Hz, J$_2$=2.5 Hz, aromatic proton, 1H), 7.85-7.75 (m, aromatic protons, 3H), 7.52-7.18 (m, aromatic protons, 11 H), 6.97 (d, J=9 Hz, aromatic protons, 2H), 6.88 (d, J=9 Hz, aromatic protons, 4H), 4.16 (t, J=8.5 Hz, aliphatic protons, 2H), 3.71 (s, CH$_3$, 6H), 3.61 (br t, aliphatic protons, 2H), 3.47 (br t, aliphatic protons, 2H), 3.32 (br t, aliphatic protons, 2H), 3.08 (t, J=5

Hz, aliphatic protons, 2H), 2.5 (br t, obscured by DMSO signal, aliphatic protons, 2H), 1.88 (br m, aliphatic protons, 4H).

Example 5

This example continues work of Example 4 in preparing minor groove binder-quencher conjugates, as reagents useful in the preparation of probes described herein. Specifically, 2,3,4,5,6-Pentafluorophenyl 3-{[3-({3-[4-({3-[bis(4-methoxyphenyl)-phenylmethoxy]propyl}-{4-[(2-chloro-4-nitrophenyl)diazenyl]phenyl}amino)butanoyl]pyrrolo[4,5-e]indolin-7-yl}-carbonyl)pyrrolo[4,5-e]indolin-7-yl]carbonyl}pyrrolo[4,5-e]indoline-7-carboxylate (25a where $R_1$=2-Cl and t=v=3, Reaction Scheme 6), is prepared.

aromatic proton, 1H), 7.01 (s, aromatic proton, 1H), 6.99 (m, aromatic protons, 3H), 6.88 (d, J=9 Hz, aromatic protons, 4H), 4.61 (m, aliphatic protons, 6H), 4.14 (t, J=8.5 Hz, aliphatic protons, 2H), 3.71 (s, 2×CH$_3$O, 6H), 3.59 (m, aliphatic protons, 2H), 3.43 (m, aliphatic protons, 6H), 3.34 (m, obscured by water signal, aliphatic protons, 2H), 3.22 (m, aliphatic protons, 2H), 3.08 (t, J=5 Hz, aliphatic protons, 2H), 2.5 (t, obscured by DMSO signal, COCH$_2$—, 2H), 1.89 (br m, aliphatic protons, 4H).

Analysis: Calculated: C, 68.27%; H, 4.95%; N, 10.81%. Found: C, 68.08%; H, 4.98%; N, 10.63%.

2,3,4,5,6-Pentafluorophenyl 3-{[3-({3-[4-({3-[bis(4-methoxyphenyl)phenylmethoxy]-propyl}-{4-[(2-chloro-4-nitrophenyl)diazenyl]phenyl}amino)butanoyl]pyrrolo[4,5-e]indolin-7-yl}carbonyl)pyrrolo[4,5-e]indolin-7-yl]carbonyl}pyrrolo[4,5-e]indoline-7-carboxylate (25a)

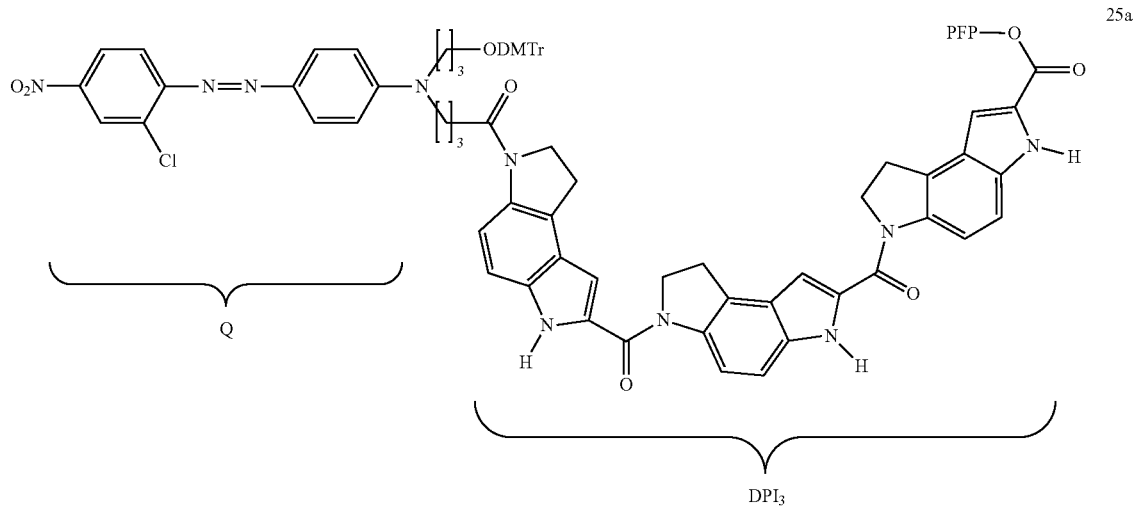

2-(4-Nitrophenyl)ethyl 3-{[3-({3-[4-({3-[bis(4-methoxyphenyl)phenylmethoxyl]propyl}-{4-[(2-chloro-4-nitrophenyl)diazenyl]phenyl}amino)butanoyl]pyrrolo[4,5-e]indolin-7-yl}carbonyl)pyrrolo[4,5-e]indolin-7-yl]carbonyl}pyrrolo[4,5-e]indoline-7-carboxylate (25)

Into a 100 mL round bottom flask is weighed out 1.31 g (1.22 mmol) of 24. This is dissolved in 25 mL of dimethylformamide. Then 0.81 mL of triethylamine is added, and finally 0.623 g (1.162 mmol) of 17. The reaction mixture is left overnight, then the solution is concentrated to ~10 mL and the resultant precipitate is filtered off, using a sintered glass filter funnel. The solid is washed with generous volumes of methanol (stirring the sludge in the filter with the methanol before applying the vacuum) several times and ether. When the effluent is clear and essentially colorless, the deep violet precipitate is dried in vacuo to afford 1.5 g (90%) of the desired product. $^1$H NMR (DMSO-d6) δ 11.96 (s, indole NH, 1H), 11.76 (s, indole NH, 1H), 11.69 (s, indole NH, 1H), 8.43 (d, J-2.4 Hz, aromatic proton, 1H), 8.35-8.20 (m, aromatic protons, 4H), 8.19 (d, J=9 Hz, aromatic protons, 2H), 7.85-7.75 (m, aromatic protons, 3H), 7.66 (d, J=9Hz, aromatic protons, 2H), 7.45-7.18 (m, aromatic protons, 12H), 7.10 (s, Into a flask is placed 1.0 g (0.73 mmol) of the product from the previous step, 40 mL of THF, and 2.46 g of DBU. The mixture is stirred at 50 degrees for 4 hours, then removed from the heat and evaporated to 15 to 20 ml. About 40 mL of methanol is added to the product and the mixture is agitated and sonicated. Then the precipitate is filtered off with a sintered glass funnel and washed with 40-60 mL of additional methanol, followed by a similar amount of ethyl ether, each time stirring the material in the filter prior to applying the vacuum so that the effluent soon becomes clear. The product is dried in vacuo for an hour or two before it is used in the next step. The material is dissolved in 20 mL of DMF in a 100 mL flask and stirred to dissolve. Then 0.6 mL (4.3 mmol) of triethylamine is added, followed by 0.6 mL of PFP-TFA. The reaction mixture is stirred under argon overnight, and then evaporated to a gum and a ~10 mL of DMF is added, followed by ~80 mL of methanol. This mixture is swirled and sonicated, and then the product, which precipitates out, is filtered off and dried in vacuo. Yield is 85-90%. $^1$H NMR (DMSO-d6) δ 12.01 (s, indole NH, 1H), 11.76 (s, indole NH, 1H), 11.69 (s, indole NH, 1H), 8.43 (d, J-2.4 Hz, aromatic proton, 1H), 8.40 (br s, aromatic proton, 1H), 8.35-8.20 (m, aromatic protons, 3H), 7.85-7.75 (m, aromatic protons, 3H), 7.59 (d, J=1.2 Hz, aromatic proton, 1H), 7.45-7.18 (m, aromatic protons, 12H), 7.13 (s, aromatic proton, 1H), 6.99 (m, aromatic protons, 3H), 6.88 (d, J=9 Hz, aromatic protons, 4H), 4.66 (m, aliphatic protons, 4H), 4.14 (t, J=8.5 Hz, aliphatic protons, 2H), 3.71 (s, 2×CH$_3$O, 6H), 3.59 (m, aliphatic protons, 2H), 3.43 (m, aliphatic protons, 6H), 3.34 (m, obscured by water signal, aliphatic protons, 2H), 3.08 (t, J=5 Hz, aliphatic protons, 2H), 2.5 (t, obscured by DMSO signal, COCH$_2$—, 2H), 1.89 (br m, aliphatic protons, 4H). Analysis: Found: C, 63.58%; H, 4.13%; N, 9.53%. Calculated, for 2.3 moles of water: C, 63.97%; H, 4.21%; N, 9.44%.

Example 6

This example illustrates the preparation of the support-bound composition, generally depicted as 29 in Reaction Scheme 7, and abbreviated as DMTrO-Red 13-amide-CDPl$_3$-CPG.

3-[(4-Methoxyphenyl)diphenylamino]propan-1-ol (26)

4 g (53 mmol) of 3-aminopropanol was dissolved by stirring in 50 mL of methylene chloride in an oven dried 250 mL round bottom flask. This solution was stoppered and set aside. 7.7 g (24.9 mmol) of monomethoxytrityl chloride (MMT-Cl, Aldrich reagent grade) was dissolved in another 50 ml of methylene chloride. An oven dried dropping funnel was fitted to the flask and the MMT-Cl solution was added to the funnel. The MMT-Cl solution was then added to the solution in the flask over ~10 min (some heat develops). After an hour the reaction was analyzed by TLC (1:1 v/v hexanes/ethyl acetate, R$_f$ 0.4) and found to be complete. Visualization of TLC spots by ninhydrin spray/heat showed a trace of (faster moving) bis-MMT side product. The reaction mixture was added to 200 mL of water standing over 200 mL of methylene chloride in a separatory funnel. The mixture was shaken and separated into layers; the aqueous layer was discarded and the organic layer was washed with an additional 200 mL of water. The organic layer was dried over 10-20 g of sodium sulfate and evaporated to give ~7 g of the tritylated amine as a pale yellow syrup. This compound did not require further purification and was dried overnight. After several days the syrup solidified. The product was recrystallized from ether-hexanes to give 4.6 g (53% yield) of 26 as a white solid (mp=89.5-90.5 EC). Anal. calcd for C$_{23}$H$_{25}$NO$_2$: C, 79.51; H, 7.25; N, 4.03. Found: C, 79.48; H, 7.18; N, 3.98.

2-[({3-[(4(4-Methoxyphenyl)diphenylamino]propyl}oxycarbonyl)methoxy]-acetic acid, triethylammonium salt (27)

2.72 g (7.83 mmol) of the alcohol (26) was dissolved in 20 mL of methylene chloride with 1.3 mL (9.4 mmol) of triethylamine and 1.1 g (9.5 mmol) of glycolic anhydride. The mixture was stirred for 2 h (became homogeneous). TLC showed clean reaction (Rf=0.35 in 9:1/methylene chloride:methanol). The solvents were removed by evaporation and the residue was chromatographed on a 1.5×18 inch silica gel column packed with 93% methylene chloride, 5% methanol, and 2% triethylamine. The fractions containing product were combined and solvent was removed by evaporation. Co-evaporation with dry DMF ensured removal of traces of water and of residual volatile solvents. Yield of the colorless syrup (27) was assumed to be 100%. The syrup was dissolved in dry DMF to give a final volume of 23.4 mL (~0.33 M solution).

Synthesis of N-MMT diglycolate CPG (28)

10 g of LCAA-CPG was combined with 5 mL of a 0.33 M solution of 27 in DMF (1.66 mrnol) in a 100 mL round bottom flask. A solution of 2.5 mL of diisopropylethylamine, 0.11 g (0.8 mmol) of HOBT and 0.63 g (1.66 mmol) of HBTU was prepared and added to the CPG. The mixture was stoppered and swirled for 16 h on an orbital shaker (150 rpm). The CPG was filtered on a medium porosity sintered glass funnel and washed with 2×100 mL of DMF, 2×100 mL of acetonitrile, and 2×100 mL of ether. Traces of ether were removed in vacuo (oil pump). Unreacted amino groups were acetylated by treating the CPG with 40 mL of dry pyridine and 5 mL of acetic anhydride. After swirling for 1.5 h, the CPG was filtered and washed with 2×100 mL of DMF, 2×100 mL of acetonitrile, and 2×100 mL of ether. Traces of ether were removed in vacuo (oil pump). The CPG was analyzed for MMT loading by treating 3-5 mg of CPG in 25 mL of 1:1/70% perchloric acid:methanol. The absorbance of the released MMT cation was recorded at 472 nm and loading level was calculated to be 95.7: mol/g of CPG using the equation:

$$MMT \text{ loading } (:\text{mol/g}) = A_{472} \times \text{volume (in mL)} \times 14.3 \div \text{wt of } CPG \text{ (mg)}$$

Synthesis of CPG 29

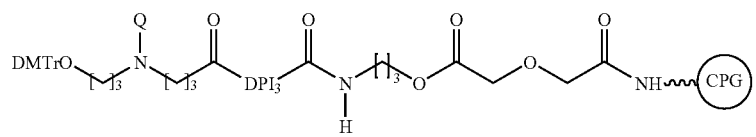

29

4 g of N-MMT diglycolate CPG (28) was weighed into a medium porosity sintered glass funnel. The CPG was detritylated by treating with 25 mL of 3% TCA/DCM. After stirring briefly with a spatula, the mixture reacted for 5 min before filtering (turned yellow). The process was repeated 4 times until the filtrate was colorless. The CPG was washed with 4×40 mL of methylene chloride. The filtrate was discarded to organic waste, and the CPG was neutralized by treatment with 40 mL of 20% triethyiamine in acetonitrile. After briefly stirring with a spatula, the mixture was filtered and washed with 2×40 mL of acetonitrile, and 2×40 mL of ether. Traces of ether were removed in vacua (oil pump). The de-tritylated CPG was used immediately for the following immobilization reaction.

0.259 g (180: mol) of 25a (see Example 5) was shaken with 12 mL of dry DMSO in a 15 mL polypropylene tube. After 15 min, the dark purple solution was added to 4 g of detritylated diglycolate CPG (in a 50 mL round bottom flask). This corresponds to an offering ratio of 45: mol PFP ester per gram of CPG. An additional 5 mL of DMSO was added to the polypropylene tube to dissolve residual PFP ester and the solution was added to the CPG. 2 mL of triethylamine was added and the mixture was stoppered and swirled on an orbital mixer for 14 h. The CPG was filtered and washed with 2×50 mL of DMSO, 2×50 mL of acetonitrile, and 2×50 mL of ether. Traces of ether were removed in vacuo (oil pump). Unreacted amino groups were acetylated by treating the CPG with 10 mL of dry pyridine and 3 mL of acetic anhydride. After swirling for 6 h, the CPG was filtered and washed with 2×50 mL of DMF, 2×50 mL of acetonitrile, and 2×50 mL of ether. Traces of ether were removed in vacuo (oil pump). The CPG was analyzed for DMT loading by treating 3-5 mg of CPG in 25 mL of 1:1/70% perchloric acid:methanol. The absorbance of the released DMT cation was recorded at 498 nm and loading level was calculated to be 45:mol/g of CPG using the equation:

$$DMT \text{ loading } (:\text{mol/g}) = A_{498} \times \text{volume (in mL)} \times 14.3 \div \text{wt of } CPG \text{ (mg)}$$

Example 7

Synthesis of FL-ODN-Red 13-amide-CDPI$_3$ (30)

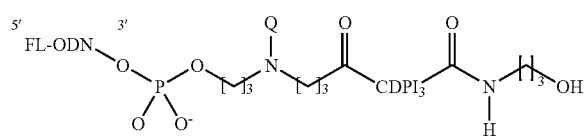

The oligonucleotides were synthesized on the CPG 29 using standard phosphoramidite coupling chemistry except that the standard 0.1 1$_2$ oxidizing solution was diluted to 0.01-0.015 to avoid iodination of the MGB moiety. FAM and TET were incorporated at the 5'end using the corresponding phosphoramidites available from Glen Research.

Example 8

This example illustrates the preparation of a coumarin-based phosphoramidite reagent as shown in Reaction Scheme 8. Specifically, 4-{[N-(6-{[Bis(methylethyl)amino](2-cyanoethoxy)phosphinooxy}hexyl)carbamoyl]methyl}-2-oxo-2H-chromen-7-yl 2,2-dimethylpropanoate (34a) is prepared.

N-(6-Hydroxyhexyl)-2-(7-hydroxy-2-oxo (2H -chromen-4-yl))acetamide (32a)

(7-Hydroxy-2-oxo-2H-chromen-4-yl)-acetic acid methyl ester (1) was synthesized according to Baker et al. (*J. Chem. Soc.;* 1950; 170, 173.).

A solution of 31 (2.0 g, 8.5 mmol, wherein one of R$_{23}$ through R$_{26}$ is OH) and 6-aminohexanol (4.0 g, 34.1 mmol) in 15 mL of DMF was heated at 80° C. for 24 h. DMF was evaporated under vacuum to afford the mixture of the product and the excess 6-aminohexanol as a viscous syrup. Chromatography on silica eluting with 10% MeOH/CH$_2$Cl$_2$ and evaporation of the pure product fractions afforded a white solid which was washed with ether and dried under vacuum. The yield was 2.05 g (75%).

4-{[N-(6-Hydroxyhexyl)carbamoyl]methyl}-2-oxo-2H-chromen-7-yl 2,2-dimethylpropanoate (33a)

To a solution of 32a (2.0 g, 6.3 mmol) in 20 mL of dry pyridine was added 4,4'-dimethoxytriphenylmethyl chloride (3.0 g, 8.9 mmol). The solution was kept at room temperature for 1 h. TLC analysis (ethyl acetate, R$_f$~0.7) showed complete reaction (protection of the primary hydroxy group). To this solution was added trimethylacetic anhydride (2.0 mL, 9.9 mmol) followed by triethylamine (5 mL) and 4-(dimethylamino)pyridine (0.3 g). The mixture was stirred for 5 h, TLC analysis showed complete protection of the phenol group (R$_f$~0.9, ethyl acetate). Methanol was added to quench excess anhydride. Pyridine was removed by evaporation under vacuum and co-evaporation with xylene. The product obtained was partitioned between ethyl acetate and 2% NaHCO$_3$, the organic phase was concentrated under vacuum to give the crude DMT protected 33a.

To remove the DMT group, the DMT derivative was dissolved in 100 mL of 10% MeOH in CH$_2$Cl$_2$ and treated with 0.5 mL of trifluoroacetic acid. After being stirred for 1 h, the reaction mixture was neutralized with triethylamine (0.7 mL) and concentrated. The resultant viscous oil was partitioned between ethyl acetate and water. The organic layer was dried over Na$_2$SO$_4$ and concentrated. The solid obtained was suspended in ether (50 mL) and stirred for 30 min. The desired product was the insoluble material, and was collected by filtration, washed with ether and dried. The yield of the title product 33 was 1.6 g (64%).

4-{[N-(6-{[Bis(methylethyl)amino](2-cyanoethoxy)phosphinooxy}hexyl)carbamoyl]methyl}-2-oxo-2H-chromen-7-yl 2,2-dimethylpropanoate (34a)

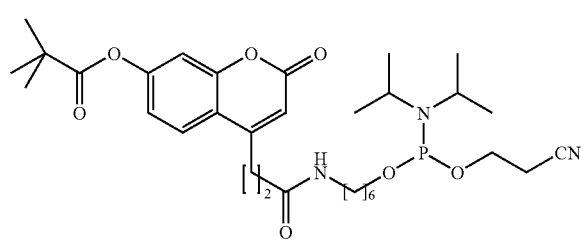

To a solution of 33a (0.6 g, 1.5 mmol) in 10 mL of anhydrous CH$_2$Cl$_2$ was added triethylamine (0.4 mL) followed by 2-cyanoethyl diisopropylchlorophosphoramidite (0.35 mL, 1.6 mmol). The solution was kept at room temperature for 1 h and treated with 0.1 mL of MeOH. The solvent was evaporated and the residue was partitioned between ethyl acetate and saturated NaHCO$_3$. The organic phase was washed with saturated NaCl, dried over Na$_2$SO$_4$ and concentrated. The crude product was chromatographed on silica eluting with 5% triethylamine in ethyl acetate. Concentration of the pure product fractions and drying under vacuum afforded 0.59 g (65%) of 34a as a colorless, viscous oil.

Example 9

This example illustrates the preparation of a resorufin phosphoramidite reagent, according to the general methods of Reaction Scheme 9 to provide 8-(3-{[bis(methylethyl)amino](2-cyanoethoxy)phosphinooxy}propyl)-7-oxophenoxazin-3-yl 2,2-dimethylpropanoate (37a).

7-Hydroxy-2-(3-hydroxypropyl)phenoxazin-3-one (35a)

A suspension of 4-nitrosorecorcinol (4.5 g, 32.4 mmol), 4-(3-hydroxypropyl)benzene-1,3-diol (Forchiassin, M.; Russo, C., *J. Heterocyc. Chem.* 20:493-494 (1983)) (4.0 g, 23.8 mmol) and $MnO_2$ (2.5 g, 17.6 mmol) in 50 mL of MeOH was cooled to ~0° C. (ice bath). To this suspension was added dropwise 2.5 mL of conc. $H_2SO_4$ and the reaction was stirred at room temperature for 5 h. The precipitated red resazurin compound was collected by filtration, washed with methanol and dried. The yield was 5.5 g. This product was not homogeneous, it was contaminated with resorufin compound and manganese salts.

The crude resazurin compound was suspended in a mixture of 200 mL of water and 50 mL of conc. $NH_4OH$. Zinc dust (2.0 g) was added and the suspension was stirred for 20 min. The resultant purple mixture was filtered, the filtrate was vigorously stirred on air to oxidize the leuco resorufin, the product of partial over reduction. The reaction was acidified with acetic acid, the brown solid formed was collected by filtration washed with water and dried. The yield was 2.1 g. The material contained ~50% of 2,3,4-trihydro-2H-pyrano[3,2-b]phenoxazin-9-one, product of intramolecular cyclization which had been carried over from the first step. The rest of the material was the desired title compound 35.

8-(3-hydroxypropyl)-7-oxophenoxazin-3-yl 2,2-dimethylpropanoate (36b)

A suspension of 35a (2.0 g) in 50 mL of pyridine was treated with 4,4'-dimethoxytriphenylmethyl chloride (5.0 g, 14.8 mmol) and stirred for 5 h. The mixture was filtered to remove some insoluble material and the filtrate was treated with trimethylacetic anhydride (2 mL). The solution was stirred for 15 h and MeOH (2 mL) was added to quench excess anhydride. After being stirred for 3 h, the reaction mixture was concentrated under vacuum. Residual pyridine was removed by co-evaporation with triethylamine and xylene. The resultant crude product 36a was chromatographed on silica eluting with 50% ethyl acetate/hexane.

The DMT derivative was dissolved in 100 mL of 10% $MeOH/CH_2Cl_2$ and treated with 0.5 mL of trifluoroacetic acid. After 1 h, triethylamine (2 mL) was added and the solution was concentrated. Chromatography on silica (ethyl acetate) and drying afforded 0.38 g of the desired product as an orange solid.

8-(3-{[bis(methylethyl)amino](2-cyanoethoxy)phosphinooxy}propyl)-7-oxophenoxazin-3-yl 2,2-dimethylpropanoate (37a)

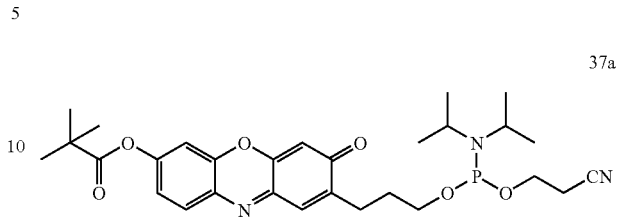

37a 36b (0.38 g, 1.1 mmol) was dissolved in 6 mL of anhydrous $CH_2Cl_2$. Triethylamine (1.5 mL) was added followed by 2-cyanoethyl diisopropylchlorophosphoramidite (0.29 mL, 1.3 mmol). The solution was kept at room temperature for 30 min, MeOH (0.1 mL) was added and the reaction was concentrated under vacuum. The residue obtained was partitioned between ethyl acetate and $NaHCO_3$. The organic phase was washed with saturated NaCl, dried over $Na_2SO_4$ and concentrated to afford the crude amidite. It was dissolved in 2 mL of ether and added dropwise to ~50 mL of hexane. The resultant orange solid was collected by filtration, washed with hexane and dried. The yield was 0.4 g.

Example 10

This example illustrates the preparation of a PPT phosphoramidite reagent according to the methods outlined in Reaction Scheme 10 to provide 3-{[(methylethyl)amino][2-(4-{3-butyl-7-[(4-methyphenyl)-carbonyl]-2,4,6,8-tetraoxo-1-((4-methylphenyl)carbonyl)(1,3,5,7,9,10-hexahydro-pyrimidino[5,4'-5,6]pyridino[2,3-d]pyrimidin-10-yl)}-phenyl)ethoxy]-phosphinooxy}propanenitrile (PPT) 44

3-n-Butyl-6-[4-(2-hydroxyethyl)aminophenyl]uracil 40

A mixture of 6-chloro-3-n-butyluracil (10.4 g, 51.3 mmol), 2-(4-aminophenyl)ethanol (10.0 g, 72.9 mmol) and ethyldiisopropylamine (18 ml, 0.1 mol) was heated with stirring under argon on a 150° oil bath for 1 hr 20 min. The mixture was cooled to room temperature, diluted with 50 ml of water, treated with 10 ml of acetic acid and stirred for crystallization overnight. A precipitated solid was filtered, washed with 2% acetic acid, dried on filter and dissolved in 100 ml of hot 96% ethanol. To the solution 100 ml of hot water was added followed by 1.0 g of charcoal. The mixture was filtered hot and crystallized on ice. Yellow solid was collected by filtration and dried in vacuum to yield 10.7 g of 40, mp 207-208° C. $^1H$ NMR (DMSO-$d_6$) δ 0.88 (t, 3H, J=7.3 Hz, $CH_3$), 1.25 (m, 2H, $CH_2$), 1.46 (m, 2H, $CH_2$), 2.70 (t, 2H, J=6.8 Hz, $CH_2$), 3.60 (dd, 2H, J=11.8, 6.8 Hz, $CH_2$), 3.68 (t, 2H, J=7.3 Hz, $CH_2$), 4.62 (t, 1H, J=5.3 Hz, OH), 4.73 (d, 1H, J=1.8 Hz, 5-H), 7.10 (d, 2H, J=8.4 Hz, ArH), 7.23 (d, 2H, J=8.4 Hz, ArH), 7.10 (s, 1H, NH), 10.37 (s, 1H, NH).

3-n-Butyl-10-[(2-hydroxyethyl)phenyl]pyrido[2,3-d;6,5-d']dipyrimidine-2,4,6,8-(3H,7H,9H,10H)-tetrone 41

A solution of 40 (6.6 g, 20 mmol) and 5-formyl-2,4,6-trichloropyrimidine (5.85 g, 27.7 mmol) in 80 ml of dry DMF was stirred at RT for 8 hr and slowly diluted with 80 ml of water. The solution produced a solid upon refrigeration for 2 days. The product was isolated by filtration, washed with cold 50% ethanol (50 ml) and 25% ethanol (50 ml) and dried in vacuum to yield 8.16 g (96%) 41 as a colorless solid, mp 205-215° C. (decomp). $^1$H NMR (DMSO-$d_6$) δ 0.88 (t, 3H, J=7.2 Hz, $CH_3$), 1.27 (m, 2H, $CH_2$), 1.48 (m, 2H, $CH_2$), 2.81-2.90 (m, 2H, $CH_2$), 3.71-3.85 (m, 4H, $CH_2$), 4.50 (br. s, 5H, OH, NH, $H_2O$), 7.26 (d, 2H, J=8.4 Hz, ArH), 7.44 (d, 2H, J=8.4 Hz, ArH), 8.62 (s, 1H, 5-H).

3-n-Butyl-5,10-dihydro-10[(2-hydroxyethyl)phenyl] pyrido[2,3-d;6,5-d']dipyrimidine-2,4,6,8-(1H,3H,7H, 9H,10H)-tetrone 42

To a suspension 41 (7.91 g, 18.7 mmol) in 300 ml of 25% aq. $NH_3$ was added $Na_2S_2O_4$ (13.8 g, 85%, 67 mmol) and slowly heated to 60° with stirring. The mixture was stirred at 60° for 40 min, diluted with water (100 ml) and stirred for additional 1 hr at the same temperature. A clear solution formed. The solution was partially evaporated to one half of its original volume, cooled with ice and neutralized with 50 ml of acetic acid to pH 5 to form a precipitate. The mixture was kept in refrigerator for complete crystallization, filtered and washed with cold water. The solid was dried in vacuum to yield 7.32 g (92%) of 42 as a white solid, mp 182-210° C. (decomp). $^1$H NMR (DMSO-$d_6$) δ 0.86 (t, 3H, J=7.3 Hz, $CH_3$), 1.23 (m, 2H, $CH_2$), 1.42 (m, 2H, $CH_2$), 2.80 (t, 2H, J=6.6 Hz, $CH_2$), 3.14 (s, 2H, 5-$CH_2$), 3.68 (m, 4H, $ArCH_2CH_2$), 4.64 (t, 1H, OH), 725 (d, 2H, J=8.3 Hz, ArH), 7.33 (d, 2H, J=8.3 Hz, ArH), 7.73 (br. s, 3H, NH).

44

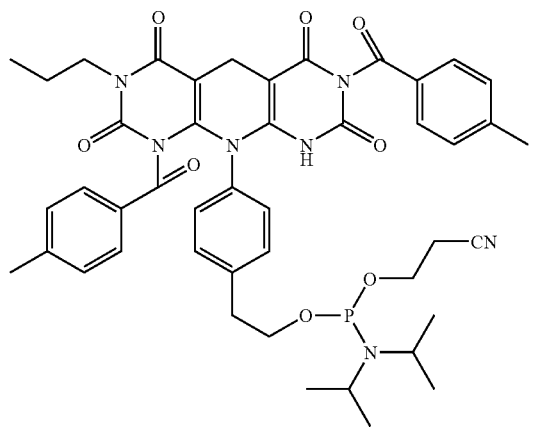

PPT 44

Solid 42 (1.2 g, 2.82 mmol) was evaporated with pyridine (10 ml), suspended in pyridine (13 ml), treated with $Me_3SiCl$ (2.2 ml, 17.3 mmol) and stirred under argon at ambient temperature for 30 min. The reaction mixture was cooled with ice and treated slowly with toluoyl chloride (5 ml, 28.8 mmol). Stirring was continued at room temperature for 2 hr, and the solvent evaporated. The residue was treated with acetic acid (10 ml) followed by addition of water (10 ml). Precipitated oil was extracted with hexanes (3×50 ml), and the residue that was insoluble in hexanes was evaporated with water. The residue was suspended in 96% ethanol (10 ml) and filtered to recover 0.3 g of the starting material. The mother liquor was diluted with water to precipitate bis-toluoyl derivative as an oil. The oil was dried in vacuum to give 0.96 g (52%) of 43 as a solid foam. This compound without further purification was converted into phosphoramidite by the following procedure.

The solid was evaporated with acetonitrile, dissolved in 25 ml of dichloromethane, treated with diisopropylammonium tetrazolide (0.54 g, 3.13 mmol) followed by 2-cyanoethyl tetraisopropylphosphorodiamidite (0.88 g, 2.9 mmol). The reaction mixture was stirred under argon for 1 hr, treated with methanol (1 ml), taken into EtOAc (100 ml), washed with sat. NaCl solution and dried over $Na_2SO_4$. The solution was evaporated, purified by HPLC on silica gel column using a gradient system 0-50% B; $CH_2Cl_2$-hexanes-$NEt_3$ (15:30:1) (A); EtOAc (B); detected at 320 nm. The main fraction was evaporated giving a colorless foam, 0.79 g (33%) of AG1 phosphoramidite 44. $^1$H NMR ($CDCl_3$) δ 0.92 (t, 3H, J=7.3 Hz, $CH_3$), 1.07-1.42 (m, 14H, 4×$CH_3$(i-Pr), $CH_2$ (Bu)), 1.50-1.65 (m, 2H, $CH_2$ (Bu)), 2.35-2.60 (m, 2H, $CH_2CN$), 2.40 (s, 3H, $CH_3Ar$), 2.46 (s, 3H, $CH_3Ar$), 2.95-3.13 (m, 4H, 2×CH (i-Pr), $CH_2$ (Bu)), 3.45-3.60 (m, 2H, $OCH_2$), 3.80-4.02 (m, 4H, $ArCH_2CH_2$), 3.82 (s, 2H, 5-$CH_2$), 7.15-7.35 (m, 8H, ArH (Tol)), 7.45 (s, 1H, NH), 7.73 (br. s, 3H, NH), 7.95 (d, 2H, J=8.0 Hz, ArH), 8.05 (d, 2H, J=8.0 Hz, ArH). $^{31}$P NMR ($CDCl_3$) δ (ppm, $H_3PO_4$) 143.2 (s).

Example 11

N-{3-[4-[(1Z)-1-aza-2-(dimethylamino)prop-1-enyl]-1-(5-{[bis(4-methoxphenyl) phenylmethoxy}methyl]-4-{[bis(methylethyl) amino](2-cyanoethyl)phophinooxy}oxolan-2-yl) pyrazolo[5,4-d]pyrimidin-3-yl]propyl}[2-({4-[(2-chloro-4-nitrophenyl)diazenyl]phenyl}ethylamino)-ethoxy]carboxamide (50) (Reaction Scheme 11)

4-Amino-1-(2-deoxy-β-D-erythro-pentofuranosyl)-3-(3-trifluoroacetimido-propyn-1-yl)pyrazolo[3,4-d] pyrimidine (46; n=1)

To a mixture of 45 (1.96 g, 5.20 mmol), CuI (103 mg, 0.54 mmol) and tetrakis[triphenylphosphine]palladium[0] (317 mg, 0.276 mmol) in 10 ml of anhydrous DMF was added anhydrous triethylamine (1.1 ml) followed by propargyl trifluoroacetimide (1.50 g, 9.88 mmol). The reaction mixture was stirred under argon for 4 h. The solvent DMF was removed by evaporation and the residual oil was purified by silica gel chromatography eluting with 7% methanol in ethyl acetate. The product fractions were pooled and evaporated affording a foam: 2.16 g (99%) yield.

4-Amino-1-(2-deoxy-β-D-erythro-pentofuranosyl)-3-(3-aminopropyl)pyrazolo[3,4-d]pyrimidine (47; n=1)

To a solution of 46 (2.10 g, 5.25 mmol) in 50 ml of ethanol, containing 0.300 mg of 5% palladium on carbon (preactivated with formic acid), was added 1.0 ml of 4 M triethylammonium formate buffer (pH 6.5). The mixture was shaken under 40 psi of hydrogen gas for 18 h. The mixture was filtered through Celite and the filtrate was evaporated affording a solid. 1.8 g (85%) yield.

The solid was stirred in 15 ml of concentrated ammonium hydroxide (sealed flask) for 12 h and then evaporated to dryness. The solid (47) was evaporated from dry acetonitrile and stored under vacuum: 1.74 g yield.

Synthesis of 48 (n=1, q=2, $R_5$=$CH_3CH_2$—, $R_5$, $R_5$=H, $R_1$=2-Cl, $R_5$=4-$NO_2$)

A solution of 47 (0.90 g, 2.92 mmol) and 7 (1.59 g, 2.92 mmol) was stirred in 5.0 ml of anhydrous dimethylformamide, containing 1.0 ml of triethylamine, at 50° C. for 1.0 h.

The solution was evaporated to dryness and the residue was purified by silica gel chromatography eluting with a gradient of 0-20% methanol in ethyl acetate. The product fractions were evaporated affording an amorphous solid: 0.74 g (37%) yield.

Synthesis of 49 (n=1, q=2, $R_5$=CH$_3$CH$_2$—, $R_5$, $R_5$=H, $R_1$=2-Cl, $R_5$=4-NO$_2$)

To a solution of 48 (0.71 g, 1.03 mmol) and N,N-dimethylacetamide dimethylacetal (1.9 ml) in 5.0 ml of dimethylacetamide was added 2.0 ml of triethylamine. The solution was stirred for 18 hrs and then evaporated to dryness affording an oil: 0.75 g (100%) yield.

Synthesis of 50 (n=1, q=2, $R_5$=CH$_3$CH$_2$—, $R_5$, $R_5$=H, $R_1$=2-Cl, $R_5$=4-NO$_2$)

acetate (2% triethylamine). The product fractions were evaporated affording a foam: 453-mg (76%) yield.

Example 12

Synthesis of Fluorogenic Oligodeoxynucleotide Probes

The 3'- DPI$_3$ probes were prepared by automated DNA synthesis from a DPI$_3$-modified glass support using methods described earlier (Lukhtanov et al. *Biorg. Chem.*, 7: 564-567 (1996)). Oligonucleotide synthesis was performed on an ABI 394 synthesizer according to the protocol supplied by the manufacturer except that 0.015 M (instead of the standard 0.1 M) iodine solution was utilized in the oxidation step to avoid iodination of the CDPI$_3$ moiety. To prevent extension during PCR, probes without 3'-CDPI$_3$ were prepared with the 3'-hydroxyhexyl phosphate as previously described (Gamper et al. *Biochem.* 36: 14816-14826 (1997)). The quencher phos-

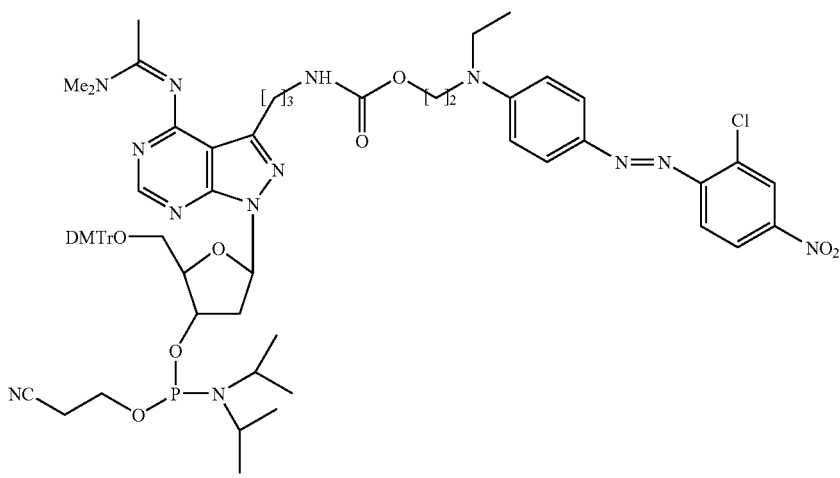

50

Dimethoxytrityl chloride (0.42 g) was added to a solution of 49 (0.75 g, 1.03 mmol) in 10 ml of dry pyridine. The solution was stirred for 4.0 hr under argon and then poured into 200 ml of 5% sodium bicarbonate solution. The product was extracted with 300 ml of ethyl acetate. The extract was dried over sodium sulfate and evaporated. The residue was purified by silica gel chromatography eluting with 10% methanol in ethyl acetate (1% triethylamine). The product fractions were evaporated affording a foam: 556 mg (57%) yield.

To a solution of the 5'-dimethoxytrityl derivative (540 mg, 0.567 mmol) in 15 ml of anhydrous methylene chloride, containing 0.30 ml of diisopropylethylamine, was added 2-cyanoethyl N,N-diisopropylchlorophosphoramidite (0.25 ml). After stirring for 30 minutes under argon at 25° C. the solution was treated with 1.0 ml of methanol and diluted with 200 ml of ethyl acetate. The solution was washed with 200 ml of 5% sodium bicarbonate solution and dried over sodium sulfate and evaporated. The crude product was purified by silica gel chromatography eluting with 5% methanol in ethyl phoramidites were added to the CPG and standard β-cyanoethylphosphoramidites and reagents (Glen Research, Sterling, Va.) were used in oligonucleotide synthesis. 6-Carboxyfluorescein (6-FAM) phosphoramidite (Glen Research) was used to introduce the 5'-reporter dyes. Alternatively TAMRA-dU phosphoramidite (Glen Research), cy3 or cy5 phosphoramidite (Glen Research), resorufin phosphoramidite, coumarin phosphoramidite, or AG phosphoramidite was used to introduce the indicated 5'-fluorophore. 5'-Hexylamine phosphoramidite (Glen Research) was incorporated into certain ODNs for post-synthetic conjugation of the 3'-quencher dye tetramethyirhodamine (TAMRA). After deprotection, all oligonucleotides were reverse-phase HPLC purified and isolated as the sodium salts by butanol concentration/sodium perchlorate precipitation (Milesi et al. *Methods Enzym.* 313: 164-173 (1999)).

Example 13

Post-Synthetic Conjugation of ODNs with TAMRA

TAMRA NHS ester (Glen Research) was used to acylate the hexylamine linkers in certain ODNs according to the protocol supplied by the manufacturer. The resulting CDPI$_3$-probes with two conjugated dyes were purified by denaturing gel electrophoresis using 8% polyacrylamide. The desired bands were excised and the gel slices were incubated overnight at 37° C. in 10 mL of 100 mM Tris-HCl, 10 mM triethylammonium chloride, 1 mM EDTA (pH 7.8). The products were isolated from the extract by reverse phase HPLC, butanol concentration and sodium perchlorate precipitation. The pellets were dissolved in water and the concentrations were determined spectrophotometrically. A nearest neighbor model (Cantor et al. Biopolymers 9: 1059-1077 (1970) was applied to calculate extinction coefficients ($\epsilon_{260}$) of ODNs. For the conjugates and probes, extinction coefficients were calculated as a sum of $\epsilon_{260}$ for the ODN and the incorporated residues of DPI$_3$ (68,000 M$^{-1}$, cm$^{-1}$), 6-FAM (22,800 M$^{-1}$, cm$^{-1}$), TAMRA (34,000 M$^{-1}$, cm$^{-1}$) and quencher (11,300 M$^{-1}$, cm$^{-1}$).

Example 14

Digestion of Oligonucleotides by Snake Venon Phosphodiestaerase

Oligonucleotides were digested with snake venom phosphodiesterase (PDE) to study the fluorescence quenching potential of various quenchers. 200 nM of oligonucleotide was taken in a buffer containing 40 mM of NaCl, 20 mM of Tris (pH 8.9), 5 mM of MgCl$_2$ and 0.025% of BSA. Initial fluorescence was read on a LS50B fluorimeter (Perkin-Elmer Corporation, Foster City, Calif.) before the addition of phosphodiesterase (Pharmacia, Piscataway, N.J.) 54 units of enzyme was added to the reaction mixture and incubated at 37° C. for 16 hrs. The final fluorescence was then measured using the LS50B. The ratio of final fluorescence to the initial fluorescence represents the signal to noise ratio (S/N) of the quenchers. Independently the kinetics of digestion reactions were monitored using the LS50B to determine the time required for complete digestion of oligonucleotides.

Example 15

5' Nuclease PCR Assay

CDPI$_3$-conjugated oligonucleotides were conjugated with a fluorophore, FAM at the 5' end and various quenchers were conjugated through a linker at the 3' end by the methods discussed above. 5' nuclease assays were performed with the above oligonucleotides to determine the quenching ability of the various quenchers under investigation. Fluorescent monitoring was performed in an Idaho Technologies LC-24 Light-Cycler. Each reaction contained PCR buffer (40 mM NaCl, 20 mM Tris HCl, pH 8.9, 5 mM MgSO$_4$, 0.05% bovine serum albumin), 125 mM each dNTP, 0.5 mM each primer, 0.1 mM fluorescent CDPI$_3$ probe, 0.5 U/10 mL Taq polymerase and 0.1 ng/10 mL of synthetic DNA as template. The cycling program was 50 cycles (or as indicated) of 2 sec at 95° C., then 30 sec at the extension temperature (55-70° C.).

Example 16

This example illustrates the SNP detection of different RRM1 alleles with a non-cleavable MGB-Q-ODN-Fl conjugate.

PCR detection in human genomic DNA was conducted in an asymmetric manner with 4 µM of primer 1 (GTA CTT TCA ATT CAT GGA GCA TAC CT (SEQ ID NO:1)) and 100 nM of primer 2 ((ATG GCC TTG TAC CGA TGC TGA (SEQ ID NO:2)) complementary to the same strand as the probe). For multiplex format, both probes, labeled with different dyes and corresponding to different alleles were added simultaneously. Real time PCR was conducted in ABI Prism 7700 (PE Biosystems), or in Light Cycler (Idaho Technology) thermocycling fluorimeters. When using the ABI Prism instrument, 60 cycles of three step PCR (95° C. for 30 s, 56° C. for 30 s and 76° C. for 30 s or as indicated) after 2 min at 50° C. and 2 min at 95° C. were performed with 0.2 µM probe (MGB-Q-ATA TCT AGC GTT GA-FAM (SEQ ID NO:3)), using 0.25 U JumpStart DNA Polymerase (Sigma) and 0.125 U of AmpErase Uracil N-glycosylase (PE Biosystems), in 1×PCR buffer (20 mM Tris-HCl pH 8.7, 50 mM NaCl, 5 mM MgCl$_2$) and 10 ng of human genomic DNA in 10 µL reaction. For the PCR in the Light Cycler, Bovine Serum Albumin was added to the mixture to the final concentration of 250 µg/µL. Cycling was performed as follows: 2 min at 50° C. 1 min at 95° C., followed by 60 cycles of 1 s at 95° C., 20 s at 56° C. and 30 s at 76° C., or as indicated. The increase in fluorescent signal was registered during the annealing step of the reaction. Human genomic DNAs from a pedigree family number 66 (homozygous for RRM1 allele 1 mother; homozygous for RRM1 allele 2 father and heterozygous son) were purchased from Coriell Institute of Medical Research. Genotyping was done previously in our laboratory using Restriction Length Polymorphysm (Lynas, C., Blood 90:4235-4236(1997)) and MGB-TaqMan methods. Reading was done in different channels of ABI Prism 7700 appropriate for the dye spectra or in component view screen.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A modified base comprising a quencher moiety and having the structure:

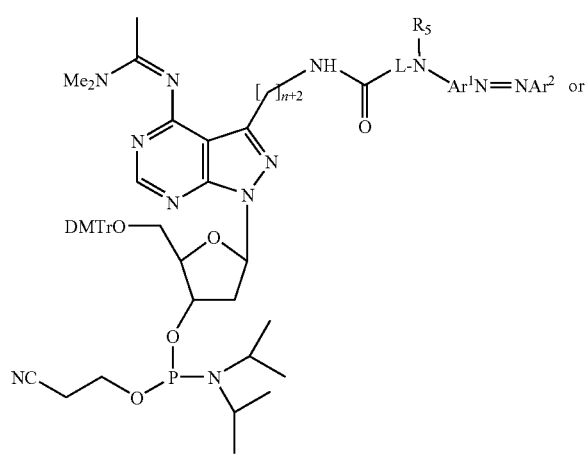 or 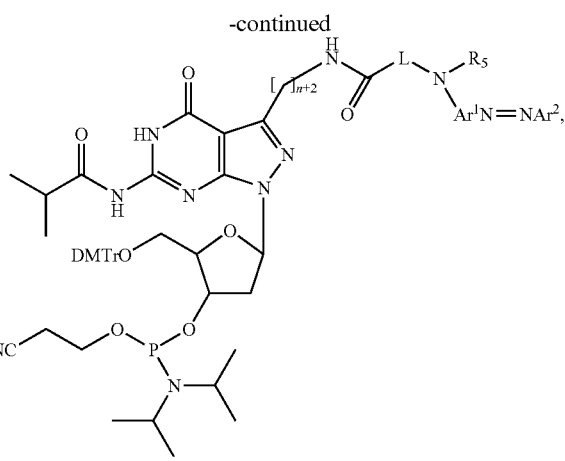

wherein

Ar$^1$ and Ar$^2$ are each independently a substituted or unsubstituted aryl group, R$_5$ is H, (C$_1$-C$_8$)alkyl, aryl, heteroalkyl, or heteroaryl;

L is a linking group having from 3 to 100 backbone atoms selected from C, N, O, S, Si and P, said linking group being cyclic, acyclic, aromatic or a combination thereof, and n is an integer from 1 to 10.

2. The modified base of claim 1 wherein one of Ar$^1$ and Ar$^2$ is a substituted aryl group.

3. The modified base of claim 1 wherein one of Ar$^1$ and Ar$^2$ is substituted with -halogen, —OR', —OC(O)R', —NR'R", —SR', —R', —CN, —NO$_2$, —CO$_2$R', —CONR'R", —C(O)R', —OC(O)NR'R", —NR"C(O)R', —NRC"C(O)$_2$R', —NR'—C(O)NR"R'", —NH—C(NH$_2$)NH, —NR'C(NH$_2$)NH, —NH—C(NH$_2$)=NR', —S(O)R', —S(O)$_2$R', —S(O)$_2$NR'R", —N3, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$) alkyl, and (unsubstituted aryl)oxy-(C$_1$-C$_4$)alkyl.

4. The modified base of claim 1 wherein one of Ar$^1$ and Ar$^2$ is directly or indirectly substituted with a substituted aryl group (Ar$^3$) where Ar$^3$ extends the resonance ability of the Ar$^1$—N=N—Ar$^2$ aromatic system and thereby increase the wavelength absorbance maximum of the compound.

5. The modified base of claim 4 wherein Ar$^3$ is substituted with -halogen, —OR', —OC(O)R', —NR'R", —SR', —R', —CN, —NO$_2$, —CO$_2$R', —CONR'R", —C(O)R', —OC(O)NR'R", —NR"C(O)R', —NRC"C(O)$_2$R', —NR'—C(O)NR"R'", —NH—C(NH$_2$)NH, —NR'C(NH$_2$)NH, —NH—C(NH$_2$)=NR', —S(O)R', —S(O)$_2$R', —S(O)$_2$NR'R", —N3, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)—(C$_1$-C$_4$)alkyl, and (unsubstituted aryl)oxy—(C$_1$-C$_4$)alkyl.

6. The modified base of claim 1 having the structure:

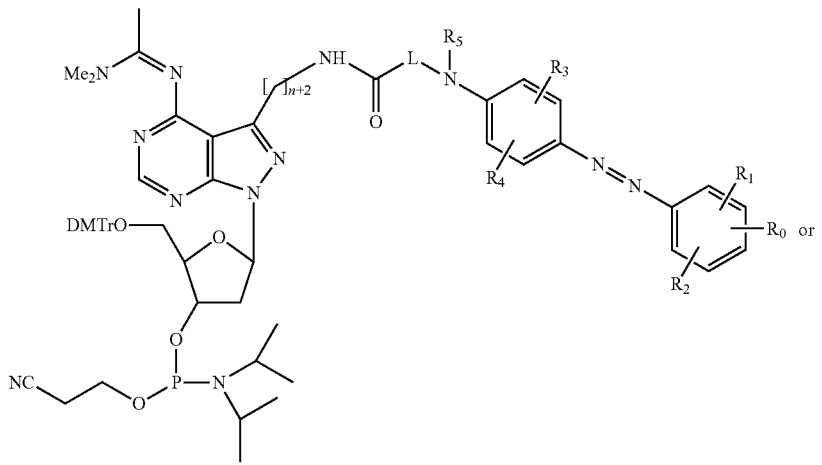

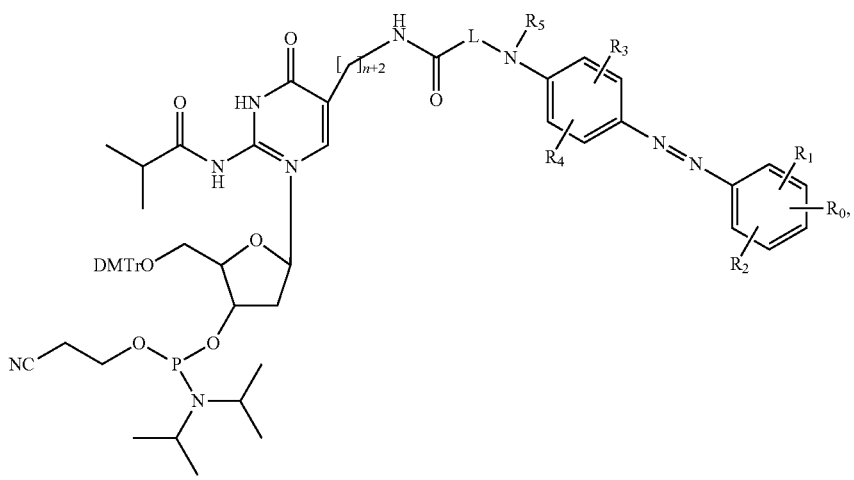

wherein
$R_0$, $_{R1}$, $R_2$, $R_3$, and $R_4$ are independently H, halogen, $NO_2$, $SO_3R$, $SO_2N(R)_2$, $C(O)OR$, $C(O)N(R)_2$, $CN$, $CNS$, $OR$, $OC(O)R$, $SR$, $CF_3$, $NHC(O)R$, $N(R)_2$, or $N(R)_3$, wherein R is independently H, $(C_1-C_8)$alkyl, aryl, or heteroaryl.
7. The modified base of claim 1 having the structure:
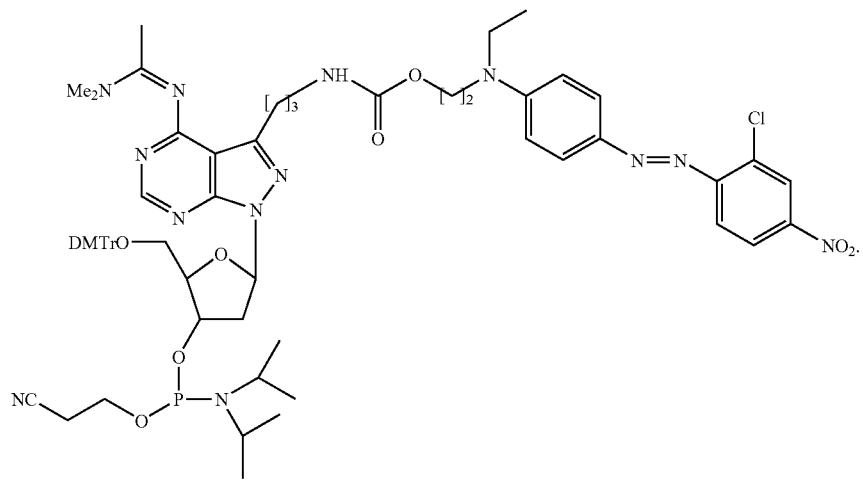
8. The modified base of claim 1 having the structure:
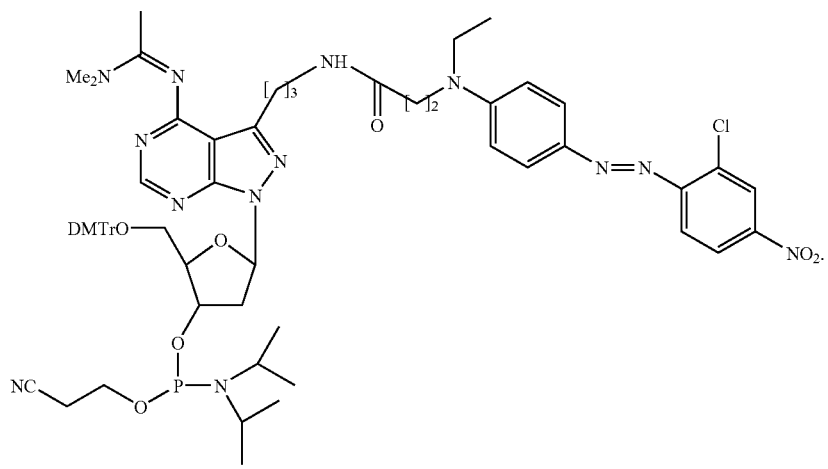

9. A method for synthesizing an oligonucleotide or oligonucleotide conjugate having one or more modified bases comprising synthesizing an oligonucleotide or oligonucleotide conjugate and incorporating into the oligonucleotide or oligonucleotide conjugate at least one modified base of claim 1.

10. A modified base comprising a quencher moiety and having the structure:

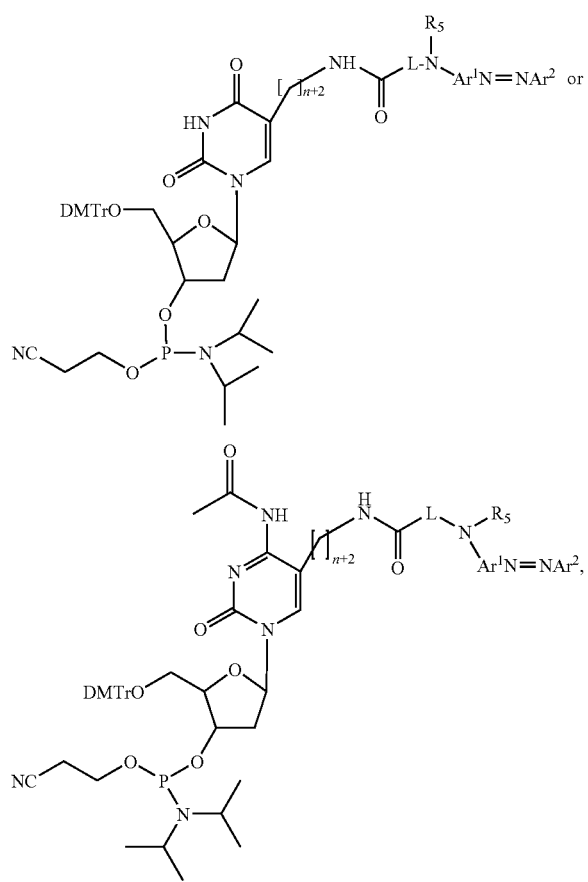

wherein $Ar^1$ and $Ar^2$ are each independently a substituted or unsubstituted aryl group, $R_5$ is H, $(C_1-C_8)$alkyl, aryl, heteroalkyl, or heteroaryl;

L is a linking group having from 3 to 100 backbone atoms selected from C, N, O, S, Si and P, said linking group being cyclic, acyclic, aromatic or a combination thereof, and n is an integer from 1 to 10.

11. The modified base of claim 10 wherein one of $Ar^1$ and $Ar^2$ is a substituted aryl group.

12. The modified base of claim 10 wherein one of $Ar^1$ and $Ar^2$ is substituted with -halogen, —OR', —OC(O)R', —NR'R", —SR', —R', —CN, —NO$_2$, —CO$_2$ R', —CONR'R", —C(O)R', —OC(O)NR'R", —NR"C(O)R', —NRC"C(O)$_2$ R', —NR'—C(O)NR"R'", —NH—C(NH$_2$)NH, —NR'C(NH$_2$)NH, —NH—C(NH$_2$)=NR', —S(O)R', —S(O)$_2$ R', —S(O)$_2$ NR'R", —N3, —CH(Ph)$_2$, perfluoro$(C_1-C_4)$alkoxy, and perfluoro$(C_1-C_4)$alkyl, in a number ranging from zero to the total number of open valences on the aromatic ring system; and where R', R" and R'" are independently selected from hydrogen, $(C_1-C_8)$alkyl and heteroalkyl, unsubstituted aryl and heteroaryl, (unsubstituted aryl)-$(C_1-C_4)$ alkyl, and (unsubstituted aryl)oxy-$(C_1-C_4)$alkyl.

13. The modified base of claim 10 wherein one of $Ar^1$ and $Ar^2$ is directly or indirectly substituted with a substituted aryl group $(Ar^3)$ where $Ar^3$ extends the resonance ability of the $Ar^1$—N=N—$Ar^2$ aromatic system and thereby increase the wavelength absorbance maximum of the compound.

14. The modified base of claim 13 wherein $Ar^3$ is substituted with -halogen, —OR', —OC(O)R', —NR'R", —SR', —R', —CN, —NO$_2$, —CO$_2$ R', —CONR'R", —C(O)R', —OC(O)NR'R", —NR"C(O)R', —NRC"C(O)$_2$ R', —NR'—C(O)NR"R'", —NH—C(NH$_2$)NH, —NR'C(NH$_2$)NH, —NH—C(NH$_2$)=NR', —S(O)R', —S(O)$_2$ R', —S(O)$_2$ NR'R", —N3, —CH(Ph)$_2$, perfluoro$(C_1-C_4)$alkoxy, and perfluoro$(C_1-C_4)$alkyl, in a number ranging from zero to the total number of open valences on the aromatic ring system; and where R', R" and R'" are independently selected from hydrogen, $(C_1-C_8)$ alkyl and heteroalkyl, unsubstituted aryl and heteroaryl, (unsubstituted aryl)-$(C_1-C_4)$alkyl, and (unsubstituted aryl)oxy-$(C_1-C_4)$alkyl.

15. A method for synthesizing an oligonucleotide or oligonucleotide conjugate having one or more modified bases comprising synthesizing an oligonucleotide or oligonucleotide conjugate and incorporating into the oligonucleotide or oligonucleotide conjugate at least one modified base of claim 10.

16. A modified base comprising a quencher moiety and having the structure:

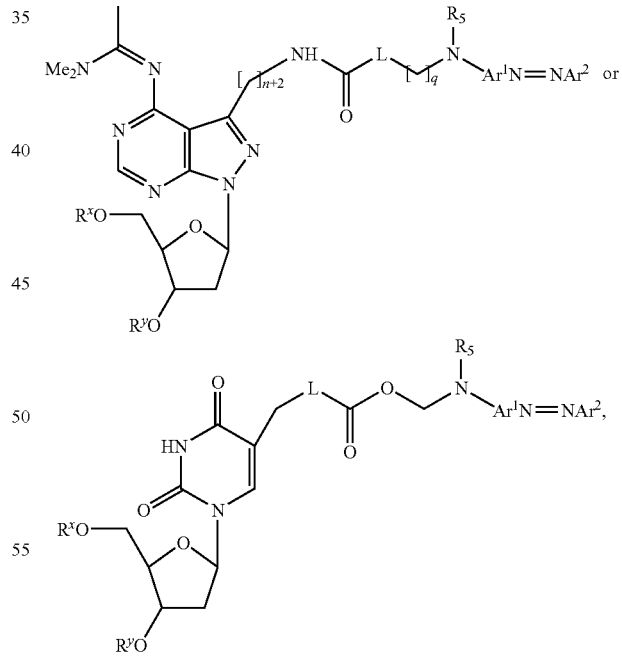

wherein $Ar^1$ and $Ar^2$ are each independently a substituted or unsubstituted aryl group, one of $R^x$ or $R^y$ is dimethoxytrityl and one of $R^x$ or $R^y$ is $P(N(iBu)_2)(CH_2CH_2CN)$, n is an integer from 1 to 10, q is an integer from 1 to 20, $R_5$ is H, $(C_1-C_8)$alkyl, aryl, heteroalkyl, or heteroaryl, and
L is a linking group having from 3 to 100 backbone atoms selected from C, N, O, S, Si and P, said linking group being cyclic, acyclic, aromatic or a combination thereof.

17. A method for synthesizing an oligonucleotide or oligonucleotide conjugate having one or more modified bases comprising synthesizing an oligonucleotide or oligonucleotide conjugate and incorporating into the oligonucleotide or oligonucleotide conjugate at least one modified base of claim 16.

* * * * *

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Primer sequence

```
<400> SEQUENCE: 1
gtactttcaa ttcatggagc atacct                                         26

<210> SEQ ID NO 2
<211> LENGTH: 21
<212> TYPE: DNA
<213> ORGANISM: Artificial Sequence
<220> FEATURE:
<223> OTHER INFORMATION: Primer sequence

<400> SEQUENCE: 2
atggccttgt accgatgctg a                                              21

<210> SEQ ID NO 3
<211> LENGTH: 14
<212> TYPE: DNA
<213> ORGANISM: Artificial Sequence
<220> FEATURE:
<223> OTHER INFORMATION: Probe labeled with MGB, quencher, and FAM
<220> FEATURE:
<221> NAME/KEY: modified_base
<222> LOCATION: (1)..(1)
<223> OTHER INFORMATION: a is conjugated to quencher and MGB
<220> FEATURE:
<221> NAME/KEY: modified_base
<222> LOCATION: (14)..(14)
<223> OTHER INFORMATION: a is conjugated to FAM

<400> SEQUENCE: 3
atatctagcg ttga                                                      14
```